(12) United States Patent
Li

(10) Patent No.: US 12,128,235 B2
(45) Date of Patent: Oct. 29, 2024

(54) CONTROLLING ELECTRICAL STIMULATION BASED ON A SENSED STIMULATION SIGNAL

(71) Applicant: Medtronic, Inc., Minneapolis, MN (US)

(72) Inventor: Jiashu Li, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 308 days.

(21) Appl. No.: 17/185,624

(22) Filed: Feb. 25, 2021

(65) Prior Publication Data

US 2021/0275817 A1 Sep. 9, 2021

Related U.S. Application Data

(60) Provisional application No. 62/986,458, filed on Mar. 6, 2020.

(51) Int. Cl.
*A61N 1/00* (2006.01)
*A61N 1/36* (2006.01)

(52) U.S. Cl.
CPC ................ *A61N 1/36139* (2013.01)

(58) Field of Classification Search
None
See application file for complete search history.

(56) References Cited

U.S. PATENT DOCUMENTS

| 5,603,726 A | 2/1997 | Schulman et al. |
| 5,800,465 A | 9/1998 | Thompson et al. |
| 5,855,594 A | 1/1999 | Olive et al. |
| 6,157,861 A | 12/2000 | Faltys et al. |

(Continued)

FOREIGN PATENT DOCUMENTS

| EP | 2396072 B1 | 3/2013 |
| EP | 3013413 A1 | 5/2016 |

(Continued)

OTHER PUBLICATIONS

"St. Jude's Prodigy Neurostimulator with Burst Technology," Medgadget, Mar. 20, 2014, 4 pp.

(Continued)

*Primary Examiner* — John R Downey
*Assistant Examiner* — Anant A Gupta
(74) *Attorney, Agent, or Firm* — Shumaker & Sieffert, P.A.

(57) ABSTRACT

This disclosure is directed to devices, systems, and techniques for controlling electrical stimulation therapy. In some examples, a medical device includes stimulation generation circuitry configured to deliver a first stimulation pulse to a patient, sensing circuitry configured to sense the first stimulation pulse, and processing circuitry. The processing circuitry is configured to determine that a value of a characteristic of the sensed first stimulation pulse exceeds a target stimulation pulse value and responsive to determining that the value of the characteristic of the sensed first stimulation pulse exceeds the target stimulation pulse value, change a first value of a parameter to a second value of the parameter that at least partially defines a second stimulation pulse deliverable by the stimulation generation circuitry after the first stimulation pulse was sensed.

27 Claims, 21 Drawing Sheets

(56) References Cited

U.S. PATENT DOCUMENTS

| | | |
|---|---|---|
| 6,205,360 B1 | 3/2001 | Carter |
| 6,289,247 B1 | 9/2001 | Faltys et al. |
| 6,314,325 B1 | 11/2001 | Fitz |
| 6,421,566 B1 | 7/2002 | Holsheimer |
| 6,505,078 B1 | 1/2003 | King et al. |
| 6,675,046 B2 | 1/2004 | Holsheimer |
| 6,850,802 B2 | 2/2005 | Holsheimer |
| 6,988,006 B2 | 1/2006 | King et al. |
| 7,076,292 B2 | 7/2006 | Forsberg |
| 7,206,640 B1 | 4/2007 | Overstreet |
| 7,333,858 B2 | 2/2008 | Killian et al. |
| 7,577,480 B2 | 8/2009 | Zeijlemaker |
| 7,616,999 B2 | 11/2009 | Overstreet et al. |
| 7,657,318 B2 | 2/2010 | King et al. |
| 7,689,289 B2 | 3/2010 | King |
| 7,742,810 B2 | 6/2010 | Moffitt et al. |
| 7,792,583 B2 | 9/2010 | Miesel et al. |
| 8,036,747 B2 | 10/2011 | Thacker et al. |
| 8,090,446 B2 | 1/2012 | Fowler et al. |
| 8,504,150 B2 | 8/2013 | Skelton |
| 8,620,441 B2 | 12/2013 | Greenberg et al. |
| 8,676,329 B2 | 3/2014 | Wacnik et al. |
| 8,694,108 B2 | 4/2014 | Alataris et al. |
| 8,708,934 B2 | 4/2014 | Skelton et al. |
| 8,712,533 B2 | 4/2014 | Alataris et al. |
| 8,712,534 B2 | 4/2014 | Wei |
| 8,751,009 B2 | 6/2014 | Wacnik |
| 8,897,888 B2 | 11/2014 | Parker et al. |
| 8,923,984 B2 | 12/2014 | Parker et al. |
| 9,002,460 B2 | 4/2015 | Parker |
| 9,072,910 B2 | 7/2015 | Parker et al. |
| 9,089,714 B2 | 7/2015 | Robinson |
| 9,089,715 B2 | 7/2015 | Parker et al. |
| 9,138,582 B2 | 9/2015 | Doan et al. |
| 9,155,892 B2 | 10/2015 | Parker et al. |
| 9,283,373 B2 | 3/2016 | Parker et al. |
| 9,302,112 B2 | 4/2016 | Bornzin et al. |
| 9,339,655 B2 | 5/2016 | Carbunaru |
| 9,364,667 B1 | 6/2016 | Dinsmoor et al. |
| 9,381,356 B2 | 7/2016 | Parker et al. |
| 9,386,934 B2 | 7/2016 | Parker et al. |
| 9,387,325 B1 | 7/2016 | Min et al. |
| 9,533,148 B2 | 1/2017 | Carcieri |
| 9,566,439 B2 | 2/2017 | Single et al. |
| 9,597,507 B2 | 3/2017 | Johanek et al. |
| 9,700,713 B2 | 7/2017 | Robinson et al. |
| 9,814,880 B2 | 11/2017 | Hershey et al. |
| 9,872,990 B2 | 1/2018 | Parker et al. |
| 9,993,646 B2 | 6/2018 | Parramon et al. |
| 10,136,832 B2 | 11/2018 | Liu et al. |
| 10,183,168 B2 | 1/2019 | Baru et al. |
| 10,569,088 B2 | 2/2020 | Dinsmoor et al. |
| 10,933,242 B2 | 3/2021 | Torgerson |
| 2004/0267333 A1 | 12/2004 | Kronberg |
| 2008/0221640 A1 | 9/2008 | Overstreet et al. |
| 2008/0300655 A1 | 12/2008 | Cholette |
| 2009/0076560 A1 | 3/2009 | Bjorling et al. |
| 2010/0198295 A1 | 8/2010 | Sheldon et al. |
| 2011/0054570 A1 | 3/2011 | Lane |
| 2011/0071589 A1 | 3/2011 | Starkebaum et al. |
| 2011/0077712 A1 | 3/2011 | Killian |
| 2011/0125223 A1 | 5/2011 | Carbunaru et al. |
| 2012/0155188 A1 | 6/2012 | Buettner et al. |
| 2013/0208390 A1 | 8/2013 | Singh et al. |
| 2013/0268021 A1 | 10/2013 | Moffitt |
| 2013/0289664 A1 | 10/2013 | Johanek |
| 2013/0289683 A1 | 10/2013 | Parker et al. |
| 2014/0005753 A1 | 1/2014 | Carbunaru |
| 2014/0025146 A1 | 1/2014 | Alataris et al. |
| 2014/0031896 A1 | 1/2014 | Alataris et al. |
| 2014/0031905 A1 | 1/2014 | Irazoqui et al. |
| 2014/0074189 A1 | 3/2014 | Moffitt |
| 2014/0142656 A1 | 5/2014 | Alataris et al. |
| 2014/0142673 A1 | 5/2014 | Carbunaru |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243924 A1 | 8/2014 | Zhu et al. |
| 2014/0243926 A1* | 8/2014 | Carcieri ............. A61N 1/36071 607/46 |
| 2014/0243931 A1 | 8/2014 | Parker et al. |
| 2014/0277282 A1* | 9/2014 | Jaax .................. A61N 1/36139 607/59 |
| 2014/0288577 A1 | 9/2014 | Robinson et al. |
| 2014/0293737 A1 | 10/2014 | Parker et al. |
| 2014/0296936 A1 | 10/2014 | Alataris et al. |
| 2014/0324143 A1 | 10/2014 | Robinson et al. |
| 2014/0371813 A1 | 12/2014 | King et al. |
| 2014/0378941 A1 | 12/2014 | Su et al. |
| 2014/0379043 A1 | 12/2014 | Howard |
| 2015/0005842 A1 | 1/2015 | Lee et al. |
| 2015/0012068 A1 | 1/2015 | Bradley et al. |
| 2015/0032181 A1 | 1/2015 | Baynham et al. |
| 2015/0057729 A1 | 2/2015 | Parker et al. |
| 2015/0127062 A1 | 5/2015 | Holley et al. |
| 2015/0179177 A1 | 6/2015 | Nagao |
| 2015/0282725 A1 | 10/2015 | Single |
| 2015/0313487 A1 | 11/2015 | Single et al. |
| 2015/0360031 A1 | 12/2015 | Bornzin et al. |
| 2015/0374999 A1 | 12/2015 | Parker et al. |
| 2016/0082252 A1 | 3/2016 | Hershey et al. |
| 2016/0121124 A1 | 5/2016 | Johanek et al. |
| 2016/0129272 A1 | 5/2016 | Hou et al. |
| 2016/0136420 A1 | 5/2016 | Brink et al. |
| 2016/0157769 A1 | 6/2016 | Min et al. |
| 2016/0158550 A1 | 6/2016 | Hou et al. |
| 2016/0166164 A1 | 6/2016 | Obradovic et al. |
| 2016/0175594 A1 | 6/2016 | Min et al. |
| 2016/0206883 A1 | 7/2016 | Bornzin et al. |
| 2016/0287126 A1 | 10/2016 | Parker et al. |
| 2016/0287182 A1 | 10/2016 | Single |
| 2016/0346534 A1 | 12/2016 | Isaacson et al. |
| 2016/0361542 A1 | 12/2016 | Kaula et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0173332 A1 | 6/2017 | Overstreet |
| 2017/0209695 A1 | 7/2017 | Solomon |
| 2017/0216587 A1 | 8/2017 | Parker |
| 2017/0216602 A1 | 8/2017 | Waataja et al. |
| 2017/0296823 A1 | 10/2017 | Hershey et al. |
| 2017/0361101 A1 | 12/2017 | Single |
| 2017/0361103 A1 | 12/2017 | Hadjiyski |
| 2018/0056073 A1 | 3/2018 | Torgerson |
| 2018/0078769 A1 | 3/2018 | Dinsmoor et al. |
| 2018/0110987 A1 | 4/2018 | Parker |
| 2018/0117335 A1 | 5/2018 | Parker et al. |
| 2018/0126169 A1 | 5/2018 | Hou et al. |
| 2018/0132760 A1 | 5/2018 | Parker |
| 2019/0099601 A1 | 4/2019 | Torgerson |
| 2019/0105496 A1 | 4/2019 | Min et al. |
| 2019/0209844 A1 | 7/2019 | Esteller et al. |
| 2019/0366094 A1 | 12/2019 | Esteller et al. |
| 2019/0388692 A1 | 12/2019 | Dinsmoor et al. |
| 2019/0388695 A1 | 12/2019 | Dinsmoor et al. |
| 2020/0171312 A1 | 6/2020 | Dinsmoor et al. |
| 2020/0171313 A1 | 6/2020 | Dinsmoor et al. |
| 2020/0188665 A1* | 6/2020 | Annetta ............... A61N 1/3603 |
| 2020/0305745 A1 | 10/2020 | Wagenbach et al. |
| 2021/0101007 A1 | 4/2021 | Hamner et al. |

FOREIGN PATENT DOCUMENTS

| | | |
|---|---|---|
| EP | 3024540 B1 | 10/2018 |
| WO | 2002009808 A1 | 2/2002 |
| WO | 2010058178 A1 | 5/2010 |
| WO | 2012155188 A1 | 11/2012 |
| WO | 2014/210373 A1 | 12/2014 |
| WO | 2015143509 A1 | 10/2015 |
| WO | 2015179177 A1 | 11/2015 |
| WO | 2015179281 A2 | 11/2015 |
| WO | 2016090420 A1 | 6/2016 |
| WO | 2016090436 A1 | 6/2016 |

(56) References Cited

FOREIGN PATENT DOCUMENTS

| WO | 2016191808 | A1 | | 12/2016 | | |
|---|---|---|---|---|---|---|
| WO | 2017100866 | A1 | | 6/2017 | | |
| WO | 2017106503 | A1 | | 6/2017 | | |
| WO | 2017173493 | A1 | | 10/2017 | | |
| WO | 2017184238 | A1 | | 10/2017 | | |
| WO | 2017219096 | A1 | | 12/2017 | | |
| WO | 2018080753 | A1 | | 5/2018 | | |
| WO | WO-2018080754 | A1 | * | 5/2018 | ........... | A61B 5/4836 |
| WO | 2018106813 | A1 | | 6/2018 | | |
| WO | 2019231794 | A1 | | 12/2019 | | |
| WO | WO-2020251899 | A1 | * | 12/2020 | ........... | A61B 5/1116 |

OTHER PUBLICATIONS

Abejon MD "Back pain coverage with spinal cord stimulation: A different treatment for each patient," International Neuromodulation Society. Jun. 10, 2015; 567, Abstract Only, 1 pp.

Abeloos MD "High density stimulation as an alternative to uncomfortable cervical tonic spinal cord stimulation: case report," International Neuromodulation Society 12th World Congress, Jun. 11-15, 2015, Abstract Only, 1 pp.

Breel et al., "High Density Stimulation: A novel programming paradigm for the treatment of chronic pain," International Neuromodulation Society (INS) 12th World Congress; Jun. 9, 2015, Abstract Only, 1 pp.

Crosby et al., "Modulation of activity and conduction in single dorsal column axons by kilohertz-frequency spinal cord stimulation," American Physiological Society, published online Oct. 19, 2016, 27 pp.

Cuellar MD PhD, et al., "Effect of high-frequency alternating current on spinal afferent nociceptive transmission," Neuromodulation: Technology at the Neural Interface; Jul.-Aug. 2013;16(4): pp. 318-327.

Cui et al., "Effect of spinal cord stimulation on tactile hypersensitivity in mononeuropathic rats is potentiated by simultaneous GABA. sub B. and adenosine receptor activation," Neuroscience Letters 247: Apr. 1998; pp. 183-186.

Cui et al., "Spinal cord stimulation attenuates augmented dorsal horn release of excitatory amino acids in mononeuropathy via a GABAergic mechanism," Pain 73, Oct. 1997, pp. 87-95.

De Ridder et al., "Burst spinal cord stimulation for limb and back pain," World neurosurgery, Nov. 2013; 80(5):642-649, e641.

De Ridder MD PhD et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak MD et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res., 1313: (2010) available online Dec. 3, 2009 pp. 53-61.

Grider DO/PhD et al., "High Frequency (1000 Hz) Stimulation Using Commercially Available Implantable Pulse Generator," North American Neuromodulation Society. Dec. 2013, Abstract Only, 2 pp.

Guan MD PhD et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.

Guan, "Spinal Cord Stimulation: Neurophysiological and Neurochemical Mechanisms of Action" Curr Pain Headache Rep DOI 10.1007s11916-014-0260-4, Mar. 8, 2012, pp. 217-225.

Holsheimer, "Computer modelling of spinal cord stimulation and its contribution to therapeutic efficacy," Spinal Cord Aug. 1998, 36: pp. 531-540.

Hubscher et al., "Convergence and cross talk in urogenital neural circuitries," J. Neurophysiol 110: 1997-2005, first published Aug. 7, 2013, 9 pp.

Hunt et al. "The molecular dynamics of pain control," Nature Reviews Neuroscience, vol. 2, Feb. 2001, pp. 83-91.

Kemler MD et al., "Spinal cord stimulation in patients with chronic reflex sympathetic dystrophy," N Engl J Med, Aug. 31, 2000; 343(9):pp. 618-624.

Kilgore PhD et al., "Reversible Nerve Conduction Block Using Kilohertz Frequency Alternating Current," Neuromodulation. Aug. 2013, pp. 242-255.

Kumar et al., "Spinal cord stimulation versus conventional medical management for neuropathic pain: a multicentre randomised controlled trial in patients with failed back surgery syndrome," Pain Jul. 2007; 132(1-2): 179-188.

Likar et al., "High density spinal cord stimulation: a multi-center experience," Abstracts, International Neuromodulation Society 12th World Congress; Jun. 11-15, 2015, 1 pp.

Maeda et al., "Increased c-fos immunoreactivity in the spinal cord and brain following spinal cord stimulation is frequency-dependent," Brain Res. Mar. 9, 2009;1259: pp. 40-50, available online Jan. 6, 2009.

Maeda et al., "Low frequencies, but not high frequencies of bi-polar spinal cord stimulation reduce cutaneous and muscle hyperalgesia induced by nerve injury," Pain; Feb. 2008; 138(1): pp. 143-152.

Maggi et al., "Effect of urethane anesthesia on the micturition reflex in capsaicin-treated rats." Journal of the Autonomic Nervous System, Jan. 1990, 30(3): 247-251.

North MD et al., "Clinical outcomes of 1 kHz subperception spinal cord stimulation (SCS): Results of a prospective randomized controlled crossover trial," Abstracts, International Neuromodulation Society, Jun. 2015, 1 pp.

North MD et al., "Spinal cord stimulation versus repeated lumbosacral spine surgery for chronic pain: a randomized, controlled trial," Neurosurgery, Jan. 2005; 56(1): 98-106; discussion 106-107.

Ranck JR. et al., "Which elements are excited in electrical stimulation of mammalian central nervous system: a review," Brain Research, Nov. 21, 1975; 98(3): pp. 417-440.

Replogle MD. et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Sato et al., "Spinal cord stimulation reduces hypersensitivity through activation of opioid receptors in a frequency-dependent manner," Eur J Pain. Apr. 2013 (4): pp. 551-561, first published Oct. 5, 2012.

Schu MD, PhD. et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.

Shechter MD et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.

Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.

Smith et al., "Successful use of high-frequency spinal cord stimulation following traditional treatment failure," Stereotact Funct Neurosurg. Apr. 1, 2015; 93(3): pp. 190-193.

Snellings et al., "Effects of stimulation site and stimulation parameters on bladder inhibition by electrical nerve stimulation," BJU International, Jul. 2012, pp. 136-143, first published Jan. 19, 2012.

Song MD Phd. et al., "Efficacy of kilohertz-frequency and conventional spinal cord stimulation in rat models of different pain conditions," Neuromodulation Jan. 2014; 17(3): pp. 226-234.

(56) References Cited

OTHER PUBLICATIONS

Sweet MD et al., "High Frequency vs. Burst Stimulation Patterns for Dorsal Column Stimulation: The Importance of Charge," American Association of Neurological Surgeons, Abstract, Apr. 4, 2014, 2 pp.

Walter et al., "Inhibiting the hyperreflexic bladder with electrical stimulation in a spinal animal model." Neurourology and Urodynamics, 1993, 12:241-253. doi:10.1002/nau.1930120306. Applicant points out in accordance with MPEP 609.04(a) that the 1993 year of publication is sufficiently earlier than the effective U.S. filing date of the present application, and any foreign priority date that the particular month of publication is not in issue.

Wille MD et al., "Altering Conventional to High Density Spinal Cord Stimulation: An Energy Dose-Response Relationship in Neuropathic Pain Therapy," Neuromodulation 2016, Aug. 2016, 9 pp.

Woock et al., "Activation and inhibition of the micturition reflex by penile afferents in the cat," Am J. Physiol Regul Intergre Comp Physiol, published Apr. 23, 2008, pp. R1880-R1889.

Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

U.S. Appl. No. 17/065,383, by Medtronic, Inc. (Inventors: Dinsmoor et al.), filed Oct. 7, 2020.

U.S. Appl. No. 17/065,282, by Medtronic, Inc. (Inventors: Dinsmoor et al), filed Oct. 7, 2020.

Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.

Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.

Youn et al., The Effect of High-Frequency Stimulation on Sensory Thresholds in Chronic Pain Patients, Stereotact Funct Neurosurg, Oct. 8, 2015, pp. 355-359.

Chakravarthy et al., "Sensing Evoked Compound Action Potentials from the Spinal Cord: Novel Preclinical and Clinical Considerations for the Pain Management Researcher and Clinician", J Pain Res., Dec. 4, 2020, pp. 3269-3279.

Kent et al., "Measurement of evoked potentials during thalamic deep brain stimulation", Brain Stimul, vol. 8, No. 1, Jan. 2015, p. 42-56.

Lo et al., "A Fully Integrated Wireless SoC for Motor Function Recovery after Spinal Cord Injury", IEEE Transactions on Biomedical Circuits and Systems, vol. 11, No. 3, Jun. 2017, pp. 497-509.

Lo et al., "Bio-Impedance Characterization Technique with Implantable Neural Stimulator Using Biphasic Current Stimulus", 36th Annual International Conference of the IEEE Engineering in Medicine and Biology Society, 2014, pp. 474-477, (Applicant points out, in accordance with MPEP 609.04(a), that the year of publication, 2014, is sufficiently earlier than the effective U.S. filing date, so that the particular month of publication is not an issue.).

* cited by examiner

CONTROLLING ELECTRICAL STIMULATION BASED ON A SENSED STIMULATION SIGNAL

This application claims the benefit of U.S. Provisional Patent Application No. 62/986,458, filed on Mar. 6, 2020, the entire content of which is incorporated herein by reference.

TECHNICAL FIELD

This disclosure generally relates to electrical stimulation therapy, and more specifically, control of electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In general, the disclosure is directed to devices, systems, and techniques for controlling electrical stimulation therapy by sensing at least one of stimulation signals or evoked compound action potentials (ECAPs). A medical device (e.g., an implantable medical device) can deliver one or more stimulation signals (e.g., one or more pulses) to the patient via one or more leads, and the medical device may sense respective stimulation signals and/or ECAPs elicited by the pulses. For example, the medical device may be configured to sense electrical signals. While sensing electrical signals, the medical device may sense one or more stimulation signals that are indicative of the delivered pulse. The medical device may also sense an ECAP from the delivered pulse if the delivered pulse causes a sufficient number of nerve fibers to depolarize. In response to determining that a characteristic of one or more stimulation signals (e.g., a voltage amplitude) have deviated from a target stimulation signal characteristic value, the medical device may adjust a value of one or more stimulation parameters that define a subsequent (e.g., a next) stimulation pulse to be delivered to the patient. For example, the medical device may increase or decrease a current amplitude of the next pulse(s) by a predetermined step size or based on a gain value representative of an amount of deviation from the target stimulation signal characteristic value. In this manner, the medical device may be configured to maintain a consistent volume of neural activation by adjusting the value of one or more stimulation parameters that at least partially define stimulation pulses.

In some examples, a medical device includes stimulation generation circuitry configured to deliver a first stimulation pulse to a patient; sensing circuitry configured to sense the first stimulation pulse; and processing circuitry configured to: determine that a value of a characteristic of the sensed first stimulation pulse exceeds a target stimulation pulse value; and responsive to determining that the value of the characteristic of the sensed first stimulation pulse exceeds the target stimulation pulse value, change a first value of a parameter to a second value of the parameter that at least partially defines a second stimulation pulse deliverable by the stimulation generation circuitry after the first stimulation pulse was sensed.

In some examples, a method includes delivering, by stimulation generation circuitry, a first stimulation pulse to a patient; sensing, by sensing circuitry, the first stimulation pulse; determining, by processing circuitry, that a value of a characteristic of the sensed first stimulation pulse exceeds a target stimulation pulse value; and responsive to determining that the value of the characteristic of the sensed first stimulation pulse exceeds the target stimulation pulse value, changing, by the processing circuitry, a first value of a parameter to a second value of the parameter that at least partially defines a second stimulation pulse deliverable by the stimulation generation circuitry after the first stimulation pulse was sensed.

In some examples, a medical device includes stimulation generation circuitry configured to deliver a first stimulation pulse to a patient; sensing circuitry configured to sense a residual phase of the first stimulation pulse; and processing circuitry configured to: determine that a value of a characteristic of the sensed residual phase of the first stimulation pulse exceeds a target residual phase value; and responsive to determining that the value of the characteristic of the sensed residual phase exceeds the target residual phase value, change a first value of a parameter to a second value of the parameter that at least partially defines a second stimulation pulse deliverable by the stimulation generation circuitry after the residual phase of the first stimulation pulse was sensed.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
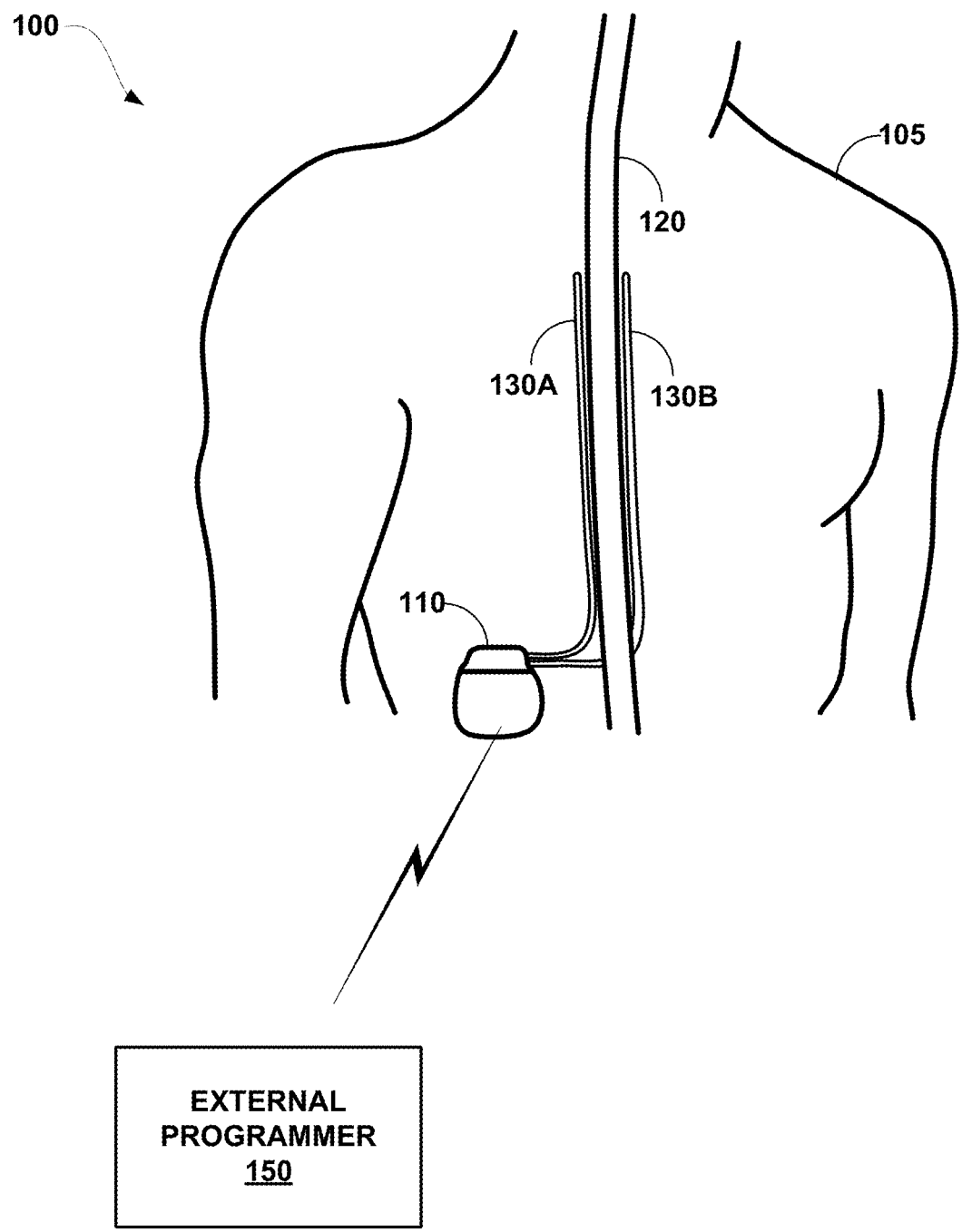
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for automatically adjusting electrical stimulation therapy delivered to a patient based on a characteristic of one or more stimulation signals sensed by a medical device in response to stimulation pulses (e.g., control pulses and/or informed pulses) delivered by the medical device and, in some examples, characteristics of evoked compound action potentials (ECAPs) detected by a medical device. Electrical stimulation therapy is typically delivered to a target tissue (e.g., one or more nerves or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, muscle disorders, etc. However, as the patient moves, the distance between the electrodes and the target tissues changes. Since neural recruitment is a function of stimulation intensity and distance between the target tissue and the electrodes, movement of the electrode closer to the target tissue may result in increased perception by the patient (e.g., possible painful sensations), and movement of the electrode further from the target tissue may result in decreased efficacy of the therapy for the patient.

ECAPs are a measure of neural recruitment because each ECAP signal represents the superposition of electrical potentials generated from axons firing in response to an electrical stimulus (e.g., a stimulation pulse). Changes in a characteristic (e.g., an amplitude of a portion of the signal, an area under one or more peaks, frequency content, and/or maximum and/or minimum peak timing) of an ECAP signal occur as a function of how many axons have been activated by the delivered stimulation pulse. A system can monitor changes in the characteristic of the ECAP signal and use that change in the characteristic to adjust one or more stimulation parameters that at least partially defines the stimulation pulses delivered to the patient. For example, the system can reduce the intensity of stimulation pulses (e.g., reduce a current amplitude and/or pulse width) in response to detecting an increase in an amplitude of an ECAP signal.

Nerve impulses may be detectable as the ECAP signal travels quickly along the nerve fiber after the delivered stimulation pulse first depolarizes the nerve. Therefore, if the stimulation pulse delivered by first electrodes has a pulse width that is too long, different electrodes configured to sense the ECAP will sense the stimulation pulse itself as a stimulation signal that obscures the lower amplitude ECAP signal. However, the ECAP signal loses fidelity as the electrical potentials propagate from the electrical stimulus because different nerve fibers propagate electrical potentials at different speeds. Therefore, sensing the ECAP at a far distance from the stimulating electrodes may avoid the stimulation signal caused by a stimulation pulse with a long pulse width, but the ECAP signal may lose fidelity needed to detect changes to the ECAP signal that occur when the electrode to target tissue distance changes or when a targeted activated fiber distribution changes or terminates before a sensing electrode location. In other words, the system may not be able to identify, at any distance from the stimulation electrodes, ECAPs from stimulation pulses configured to provide a therapy to the patient.

Although a system can use ECAP signals to detect changes to stimulation therapy, ECAP signals may not always be present or detectable. For example, the delivered stimulation pulse may have an intensity that is too low to elicit a detectable ECAP signal. For example, the stimulation pulse may be referred to as a "sub-threshold" stimulation pulse because the stimulation pulse is below at least one of a perception threshold, a motor threshold, or an ECAP detection threshold. Sub-threshold stimulation pulses may cause a therapeutic effect for the patient, but the lack of a detectable ECAP signal may prevent the system from using an ECAP signal to modulate stimulation parameter values in response to changes in the distance between electrodes and target tissue (e.g., target nerves).

A medical device may be configured to sense stimulation signals and adjust stimulation parameters based on a characteristic of one or more stimulation signals. As discussed above, ECAPs elicited by stimulation pulses delivered by the medical device might not be detectible by the medical device. Even if an ECAP signal is not detectable, the medical device may detect one or more stimulation signals caused by the stimulation pulse. The medical device may determine or adjust values of one or more parameters that at least partially define subsequent stimulation pulses based characteristic of the respective stimulation signals. More specifically, the stimulation signals detected by the medical device may include information indicative of an efficacy of a therapy delivered to the patient by the medical device. For example, the stimulation signals may include information indicative of a distance between one or more electrodes of the medical device and the target tissue. In this way, the medical device may adjust stimulation therapy according to the characteristics of one or more stimulation signals in order to maintain efficacy of the therapy and/or reduce undesirable side effects during or as a result of patient movement.

The term "stimulation signal" may be used herein to describe a signal that the medical device senses in response to a stimulation pulse delivered by the medical device. One or more sense electrodes of the medical device may detect a stimulation signal due to one or more stimulation electrodes proximate to the sense electrodes delivering a stimulation pulse. In this way, delivering a stimulation pulse may cause the medical device to sense a respective stimulation signal during a window of time substantially overlapping with the delivery of the stimulation pulse. An electrical potential of the stimulation electrodes during the window of time in which the medical device delivers the stimulation pulse may cause the sensing circuitry of the medical device to generate a sense signal which is representative of the stimulation pulse delivered during the window of time. The stimulation signal is thus representative of electrical potential changes in tissue directly caused by the delivered stimulation pulse. Conversely, an ECAP is a signal representative of physiological action (e.g., depolarizing nerve fibers) caused by the stimulation pulse. In this way, stimulation signals may be at least partially distinguished from ECAPs, since ECAPs represent electrical signals sensed by the medical device due to an excitation of target tissue of the patient in response to the delivery of a stimulation pulse. In other words, an ECAP represents a detected physiological response to a stimulation pulse, and a stimulation signal represents the direct detection of the stimulation pulse itself and associated changes in the charge in tissue.

In some examples, the medical device may deliver stimulation pulses in the form of control pulses and informed pulses. More specifically, electrical stimulation pulses are delivered in the form of informed pulses and control pulses that are at least partially interleaved with each other. Control pulses (e.g., stimulation signal test pulses) are those stimulation pulses that are configured to elicit one or both of a stimulation signal and a detectable ECAP signal. In some examples, control pulses may contribute to the therapy for a patient. In other examples, control pulses do not contribute to the therapy for the patient, e.g., non-therapeutic pulses. In this manner, control pulses may or may not be configured to elicit a therapeutic effect for the patient. Informed pulses are those stimulation pulses that are at least partially defined by one or more parameters based on the detectable stimulation signal elicited from one or more control pulses. In some examples, one or more informed pulses are at least partially defined by one or more parameters based on a respective ECAP elicited from one or more control pulses. In this manner, the informed pulses are "informed" by the ECAP signal detected from a control pulse. Informed pulses are also configured to provide a therapy to a patient, such as paresthesia that relieves pain symptoms.

As described herein, a medical device may be configured to deliver a plurality of informed pulses and/or control pulses configured to provide a therapy to the patient based on one or more parameters of ECAP signals elicited by previously delivered control pulses. The medical device, in some cases, may deliver a plurality of informed pulses, which are configured to provide or at least contribute to a therapy to the patient based on one or more parameters of ECAP signals elicited by control pulses. In some examples, the control pulses may be configured to elicit ECAP signals without contributing to the therapy of the patient. However, in other examples, the control pulses may provide therapy to the patient either alone or in combination with the informed pulses. The control pulses may be interleaved with the delivery of the informed pulses. For example, the medical device may alternate the delivery of informed pulses with control pulses such that a control pulse is delivered, and an ECAP signal is sensed from the control pulses, between consecutive informed pulses. In some examples, multiple control pulses are delivered, and respective ECAP signals sensed, between the delivery of consecutive informed pulses.

In some examples, multiple informed pulses will be delivered between consecutive control pulses. In any case, the informed pulses may be delivered according to a predetermined pulse frequency selected so that the informed pulses can produce or contribute to a therapeutic result for the patient. One or more control pulses are then delivered, and the respective ECAP signals sensed, within one or more time windows between consecutive informed pulses delivered according to the predetermined pulse frequency. The predetermined pulse frequency may be a single consistent frequency or a varied frequency that varies over time. The pulse width of the control pulses may be shorter than the pulse width of the informed pulses to enable the medical device to detect the stimulation signals and/or the ECAP signals elicited from the control pulses. Put another way, the longer pulse width of the informed pulses may prevent all phases of the resulting stimulation signals and prevent the resulting ECAP signals from being detected due to, for example, overlapping of the informed pulse with the ECAP signal and the stimulation signal. In this manner, a medical device can administer informed pulses from the medical device uninterrupted while one or both of ECAPs and stimulation signals can be sensed from control pulses delivered during times at which the informed pulses are not being delivered.

In some examples, a pulse frequency of stimulation pulses (e.g., control pulses and informed pules) delivered by the medical device may be within a range from 50 Hertz (Hz) to 70 Hz, but this is not required. In some examples, a pulse frequency of stimulation pulses (e.g., control pulses and informed pulses) delivered by the medical device may be within a range from 0.1 Hz to 100 kilohertz (KHz), The pulse frequency of the stimulation pulses may be within a range from 0.5 KHz to 5 KHz (e.g., 1 KHz) and/or within a range from 5 KHz to 15 KHz (e.g., 10 KHz), as examples. In some examples, when a frequency of control pulses and informed pulses increases, a maximum pulse width of control pulses which do not obscure respective control pulses decreases.

The medical device may, in some cases, determine whether a characteristic of a stimulation signal detected in response to a stimulation pulse (e.g., a control pulse) is within a range from a first threshold characteristic value to a second threshold characteristic value. The first threshold characteristic value and the second threshold characteristic value which define the range may, in some cases, depend on a posture of the patient and a magnitude of the stimulation pulse which provokes the stimulation signal sensed by the medical device. The medical device may determine the posture of the patient using an accelerometer signal. In this way, the medical device may determine one or more parameters of stimulation delivered to the patient based on whether the characteristic of the stimulation signal is within the respective range of stimulation signal characteristic values, where the range is determined based on the posture of the patient and the magnitude of the stimulation pulses (e.g., voltage magnitude, current magnitude).

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

The techniques of this disclosure may provide one or more advantages. For example, a medical device may control stimulation based on one or more stimulation signals when an ECAP is not elicited by the delivered pulse or the ECAP is otherwise not detectable. In this way, the medical device may determine a value for one or more parameters that define stimulation pulses based on a characteristic value of the one or more stimulation signals detected from previous stimulation pulse. In one example, the value for one or more parameters of the stimulation pulses may be determined from a characteristic of a third phase or residual phase of the stimulation signal (e.g., one of the stimulation signals) detected from a stimulation pulse. The third phase may occur within the final third of the stimulation signal, and the third phase may be referred to as a residual phase because it represents ionic rebalancing of any residual charge resulting from the stimulation pulse that was delivered. In this way, the medical device may be configured to determine therapy based on one or more stimulation signals when an ECAP is not present or is otherwise not detectible by the medical device. Additionally, the medical device may adjust stimulation parameters for subsequent pulses based on a characteristic value of a stimulation signal and a characteristic of an ECAP elicited by the same pulse that caused the stimulation signal. In this manner, the stimulation signal may improve the quality of feedback signals available for controlling stimulation even if the ECAP signal is detectable.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. This electrical stimulation may be delivered in the form of stimulation pulses. In some examples, IMD 110 may be configured to generate and deliver stimulation pulses to include control pulses configured to elicit ECAP signals and/or cause IMD 110 to sense stimulation signals. The control pulses may or may not contribute to therapy in some examples. In some examples, IMD 110 may, in addition to control pulses, deliver informed pulses that contribute to the therapy for the patient, but which do not elicit detectable ECAPs or cause IMD 110 to detect every phase of responsive stimulation signals. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a leads 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, leads 130 may include a lead extension or other segments that may aid in implantation or positioning of leads 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses (e.g., control pulses and/or informed pulses) are typically predetermined parameter values determined prior to delivery of the stimulation pulses (e.g., set according to a stimulation program). However, in some examples, system 100 changes one or more parameter values automatically based on one or more factors or based on user input.

A test stimulation program may define stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each test stimulation program are configured to evoke a compound action potential from nerves. In some examples, the test stimulation program defines when the control pulses are to be delivered to the patient based on the frequency and/or pulse width of the informed pulses when informed pulse are also delivered. In some examples, the stimulation defined by each test stimulation program are not intended to provide or contribute to therapy for the patient. In other examples, the stimulation defined by each test stimulation program may contribute to therapy when the control pulses elicit one or both of detectable ECAP signals and detect responsive stimulation signals. In this manner, the test stimulation program may define stimulation parameters the same or similar to the stimulation parameters of therapy stimulation programs.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, leads 130 includes one or more sensors configured to allow IMD 110 to monitor one or more parameters of patient 105, such as patient activity, pressure, temperature, or other characteristics. The one or more sensors may be provided in addition to, or in place of, therapy delivery by leads 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

In some examples where relevant phases of stimulation signals cannot be detected from the types of pulses intended to be delivered to provide therapy to the patient, control pulses and informed pulses may be delivered. For example, IMD 110 is configured to deliver control stimulation to patient 105 via a combination of electrodes of leads 130, alone or in combination with an electrode carried by or defined by an outer housing of IMD 110. The tissue targeted by the control stimulation may be the same tissue targeted by the electrical stimulation therapy, but IMD 110 may deliver control stimulation pulses via the same, at least some of the same, or different electrodes. Since control stimulation pulses are delivered in an interleaved manner with informed pulses, a clinician and/or user may select any desired electrode combination for informed pulses. Like the electrical stimulation therapy, the control stimulation may be in the form of electrical stimulation pulses or continuous waveforms.

In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. In other examples, a control stimulation pulse may include a tri-phasic pulse or pulse having more than three phases. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. In some cases, the control pulses may elicit an ECAP signal from the tissue, and IMD 110 may sense the ECAP signal via two or more electrodes on leads 130. In some examples, control pulses might not elicit ECAPs that are detectible by IMD 110, however IMD 110 may detect stimulation signals responsive to the control pulses. The control pulses may include information that is useful for determining parameters of one or more stimulation delivered to patient 105. In cases where the control stimulation pulses are applied to spinal cord 120, the signal may be sensed by IMD 110 from spinal cord 120.

IMD 110 may deliver control stimulation to a target stimulation site within patient 105 via the electrodes of leads 130 according to one or more test stimulation programs. The one or more test stimulation programs may be stored in a storage device of IMD 110. Each test program of the one or more test stimulation programs includes values for one or more parameters that define an aspect of the control stimulation delivered by IMD 110 according to that program, such as current or voltage amplitude, pulse width, pulse frequency, electrode combination, and, in some examples, timing based on informed pulses to be delivered to patient 105. In some examples, IMD 110 delivers control stimulation to patient 105 according to multiple test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy (e.g., informed pulses) and control stimulation (e.g., control pulses). For example, external programmer 150 may transmit therapy stimulation programs, test stimulation programs, stimulation parameter adjustments, therapy stimulation program selections, test program selections, user input, or other information to control the operation of IMD 110, e.g., by wireless telemetry or wired connection. As described herein, stimulation delivered to the patient may include control pulses, and, in some examples, stimulation may include control pulses and informed pulses.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

Efficacy of electrical stimulation therapy may, in some cases, be indicated by one or more characteristics (e.g. an amplitude of or between one or more peaks or an area under the curve of one or more peaks) of an action potential that is evoked by a stimulation pulse delivered by IMD 110 (i.e., a characteristic of the ECAP signal). Additionally, or alternatively, efficacy of electrical stimulation therapy may be indicated by one or more characteristics (e.g., a voltage magnitude) of a stimulation signal that is sensed in response to the stimulation pulse delivered by IMD 110. The stimulation signal may be indicative of the detection of the delivered stimulation pulse and related signals instead of action potentials evoked by the delivered stimulation pulse.

In one or more cases where stimulation pulses elicit detectible ECAPs, electrical stimulation therapy delivery by leads 130 of IMD 110 may cause neurons within the target tissue to evoke a compound action potential that travels up and down the target tissue (e.g., nerve fibers), eventually arriving at sensing electrodes of IMD 110. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

In one or more cases where a stimulation pulse causes IMD 110 to sense one or more respective stimulation signals, one or more characteristics of the respective stimulation signal may indicate an efficacy of the electrical stimulation delivered to patient 105 by IMD 110. For example, it may be beneficial for a voltage magnitude of the stimulation signal to be at a target stimulation signal value. In one example, the target stimulation signal value may be a target range from a first threshold magnitude value to a second threshold magnitude value. If the voltage magnitude of the stimulation signal is less than the first threshold magnitude value, the electrical stimulation might not be as effective at treating pain perceived by patient 105 as compared with scenarios in which the voltage magnitude of the stimulation signal is within the target range. On the other hand, if the voltage magnitude of the stimulation signal is greater than the second threshold magnitude value, the electrical stimulation might be inducing an uncomfortable (e.g., unwanted or painful) sensation perceived by patient 105 as compared with examples in which the voltage magnitude of the stimulation signal is within the target range. In some examples, IMD 110 may control the voltage magnitude of the stimulation signal to be within a target range by changing and/or setting one or more parameters of subsequent stimulation pulses (e.g., control pulses and/or informed pulses) delivered to patient 105 in response to measuring the voltage magnitude of one or more detected stimulation signals.

A target stimulation signal value (e.g., a target range or a target value) for characteristic values of the stimulation signals may, in some cases, be different depending on one or more conditions. In some examples, the target range may include an upper-bound value, a lower-bound value, a target characteristic value between the lower-bound value and the upper-bound value, or a target characteristic value plus and/or minus a tolerance value. In some examples, the upper-bound and the lower-bound of a target range of a characteristic of a stimulation signal may depend on an amplitude of the stimulation pulse which causes IMD 110 to sense the stimulation signal. For example, a first stimulation pulse including a first parameter value may cause IMD 110 to sense a first stimulation signal and a second stimulation pulse including a second parameter value may cause IMD 110 to sense a second stimulation signal, where the second parameter value is greater than the second parameter value. In at least some such cases, IMD 110 may compare a characteristic of the first stimulation signal to a first target range of characteristic values and IMD 110 may compare a characteristic of the second stimulation signal to a second target range of characteristic values, where the upper-bound value of the second target range is greater than the upper-bound value of the first target range and where the lower-bound value of the second target range is greater than the lower-bound value of the first target range. In this way, the target range of characteristic values corresponding to a characteristic of a stimulation signal may generally increase as the parameter of the stimulation pulse (e.g., an amplitude of the pulse or an area under the pulse) which causes IMD 110 to sense the stimulation signal increases.

Additionally, or alternatively, the target stimulation signal value (e.g., the target range) of characteristic values of the stimulation signals may depend on a posture of patient 105. For example, IMD 110 may include an accelerometer (not illustrated in FIG. 1) which is configured to generate an accelerometer signal. IMD 110 may be configured to determine, based on the accelerometer signal, a posture of patient 105. The determined posture may be a posture of a set of postures including a standing posture, a seated posture, a supine posture, a prone posture, and a side-lying posture, as examples. IMD 110 may be configured to select the target range of characteristic values of a stimulation signal based on the determined posture of patient 105. As discussed above, in some examples, the IMD 110 may be configured to select the target stimulation signal value of the stimulation signal based on a magnitude of the stimulation pulse which causes IMD 110 to sense the stimulation signal in addition to selecting the target range of characteristic values based on the posture of patient 105. In fact, the target range of characteristic values for a particular stimulation signal may be defined by one or more "transfer functions," where each posture of the set of postures being associated with a respective transfer function.

As described herein, a transfer function may define a relationship between a magnitude of a stimulation pulse which causes IMD 110 to sense a stimulation signal and a target stimulation signal value of the stimulation signal. Each posture of patient 105 may be associated with a transfer function which defines the respective relationship between stimulation magnitude and the target stimulation signal value of the stimulation signal. In some examples, one or more transfer functions that are each associated with a respective posture may represent a linear function, meaning that such transfer functions define a linear relationship between the magnitude of a stimulation pulse and the target range of characteristic values of the stimulation signal resulting from the stimulation pulse. However, this does not need to be the case. Transfer functions may represent any one or combination of functions including linear functions, quadratic functions, exponential functions, piecewise functions, power functions, polynomial functions, rational functions, logarithmic functions, and sinusoidal functions.

In some examples, a standing posture is associated with a first transfer function including a first slope, a sitting posture is associated with a second transfer function including a second slope, and a supine posture is associated with a third transfer function including a third slope. In some examples, the first transfer function, the second transfer function may each represent functions where a target range of characteristic values of one or more stimulation signals are plotted against a magnitude of a stimulation pulse which causes IMD 110 to sense the respective stimulation signal, where the target range of characteristic values are plotted on a y-axis of a graph, and the stimulation magnitude is plotted on an x-axis of the graph. In at least some such examples, the first slope of the first transfer function is greater than the second slope of the second transfer function, and the second slope of the second transfer function is greater than the third slope of the third transfer function. Consequently, at times when patient 105 is occupying a supine posture, the target stimulation signal value (e.g., a target range of characteristic values) is more sensitive to changes in stimulation amplitude as compared with times when patient 105 is standing or sitting.

Since the first transfer function, the second transfer function, and the third transfer function each have different slopes, IMD 110 may change the target stimulation signal value (e.g., the target range of characteristic values) based on detecting a change in the posture of patient 105. For example, in response to IMD 110 determining that patient 105 is standing, IMD 110 may select a first target range including a first lower-bound value and a first upper-bound value. If stimulation magnitude is held constant and in response to IMD 110 determining that patient 105 is sitting, IMD 110 may select a second target range including a second lower-bound value and a second upper-bound value. Additionally, if stimulation magnitude is held constant and in response to IMD 110 determining that patient 105 is occupying a supine posture, IMD 110 may select a third target range including a third lower-bound value and a third upper-bound value. In some examples, the third upper-bound value may be greater than the second upper-bound value and the second upper-bound value may be greater than the first upper-bound value. Additionally, the third lower-bound value may be greater than the second lower-bound value and the second lower-bound value may be greater than the first lower-bound value.

In the example of FIG. 1, IMD 110 is described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of a stimulation signal to external programmer 150. External programmer 150 may compare a characteristic value of the stimulation signal to the respective target range of characteristic values, and in response to the comparison, external programmer 150 may instruct IMD 110 to adjust one or more parameters that define the electrical stimulation pulses delivered to patient 105.

In some examples, stimulation generation circuitry of IMD 110 may be configured to deliver at least one stimulation pulse between a time in which the stimulation generation circuitry delivers a first stimulation pulse and a time in which the stimulation generation circuitry delivers a second stimulation pulse which is based on a stimulation signal responsive to the first stimulation pulse. In some examples, stimulation generation circuitry of IMD 110 may be configured to deliver the second stimulation pulse consecutive to the first stimulation pulse.

In the example techniques described in this disclosure, the control stimulation parameters and the target stimulation signal value (e.g., a target range of characteristic values) of the stimulation signals may be initially set at the clinic but may be set and/or adjusted at home by patient 105. Once a target stimulation signal value (e.g., a target range of characteristic values) are set, the example techniques allow for automatic adjustment of parameters of the stimulation pulses in order to maintain consistent volume of neural activation and consistent perception of therapy for patient 105 when the electrode-to-neuron distance changes. The ability to change the stimulation parameter values may also allow the therapy to have long term efficacy, with the ability to keep the intensity of the stimulation (e.g., as indicated by the detected stimulation signals) consistent by comparing the measured characteristic values of the stimulation signals to the target range of characteristic values. IMD 110 may perform these changes without intervention by a physician or patient 105.

Figure 2:
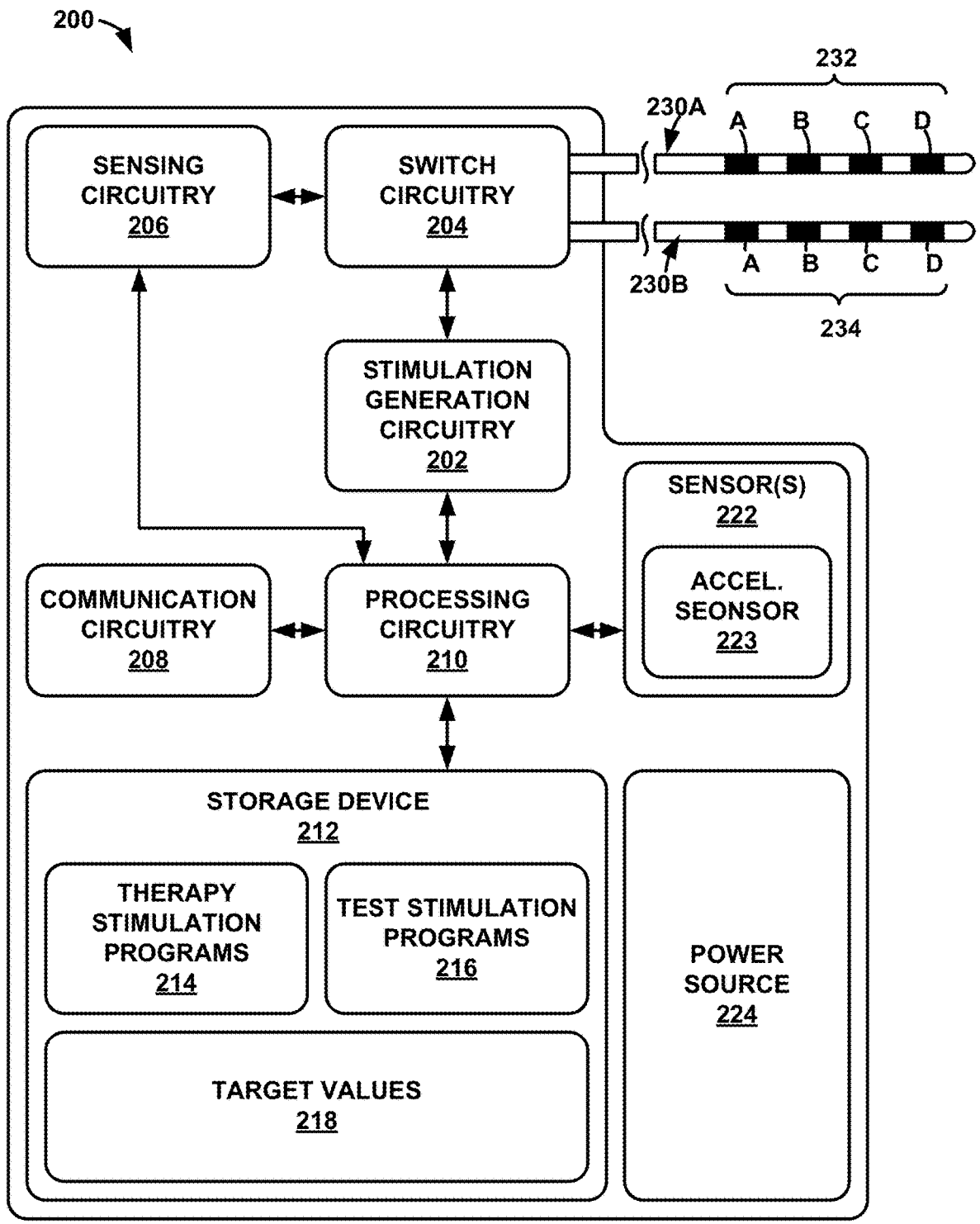
FIG. 2 is a block diagram illustrating an example configuration of components of the IMD of FIG. 1, in accordance with one or more techniques of this disclosure.

FIG. 2 is a block diagram illustrating an example configuration of components of IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, communication circuitry 208, processing circuitry 210, storage device 212, sensor(s) 222, and power source 224. As seen in FIG. 2, sensor(s) 222 include acceleration sensor 223.

In the example shown in FIG. 2, storage device 212 stores therapy stimulation programs 214 and test stimulation programs 216 in separate memories within storage device 212 or separate areas within storage device 212. Each stored therapy stimulation program of therapy stimulation programs 214 defines values for a set of electrical stimulation parameters (e.g., a stimulation parameter set), such as a stimulation electrode combination, electrode polarity, current or voltage amplitude, pulse width, pulse rate, and pulse shape. Each stored test stimulation programs 216 defines values for a set of electrical stimulation parameters (e.g., a control stimulation parameter set), such as a stimulation electrode combination, electrode polarity, current or voltage amplitude, pulse width, pulse rate, and pulse shape. Test stimulation programs 216 may also have additional information such as instructions regarding when to deliver control pulses based on the pulse width and/or frequency of the informed pulses defined in therapy stimulation programs 214. In examples in which control pulses are provided to the patient without the need for informed pulses, a separate test stimulation program may not be needed. Instead, the test stimulation program for therapy that only includes control pulses may define the same control pulses as the corresponding therapy stimulation program for those control pulses.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as ECAPs. Additionally, or alternatively, sensing circuitry 206 may sense one or more stimulation pulses delivered to patient 105 via electrodes 232, 234. In some examples, sensing circuitry 206 detects electrical signals, such as stimulation signals and/or ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Communication circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via communication circuitry 208. Updates to the therapy stimulation programs 214 and test stimulation programs 216 may be stored within storage device 212. Communication circuitry 208 in IMD 200, as well as communication circuits in other devices and systems described herein, such as the external programmer, may accomplish communication by radiofrequency (RF) communication techniques. In addition, communication circuitry 208 may communicate with an external medical device programmer (not shown in FIG. 2) via proximal inductive interaction of IMD 200 with the external programmer. The external programmer may be one example of external programmer 150 of FIG. 1. Accordingly, communication circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to therapy stimulation programs 214 and test stimulation programs 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques.

In some examples, one or more of electrodes 232 and 234 are suitable for sensing one or more ECAPs. For instance, electrodes 232 and 234 may sense the voltage amplitude of a portion of the ECAP signals, where the sensed voltage amplitude is a characteristic of the ECAP signal.

In some examples, one or more of electrodes 232 and 234 are suitable for sensing stimulation signals. For instance, electrodes 232 and 234 may sense the voltage amplitude of a portion of the stimulation signals, where the sensed voltage amplitude is a characteristic of the stimulation signals. In some examples, one or more of electrodes 232 and 234 may sense a stimulation signal in response to one or more of electrodes 232 and 234 delivering a stimulation pulse to target tissue of patient 105. In some examples, the one or more of electrodes 232 and 234 which sense the stimulation signal are not the same as the one or more of electrodes 232 and 234 which deliver the stimulation pulse.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store therapy stimulation programs 214, test stimulation programs 216, and target values 218.

In some examples, stimulation generation circuitry 202 may be configured to deliver electrical stimulation therapy to patient 105. In some examples, the electrical stimulation therapy may include a plurality of informed pulses. Additionally, stimulation generation circuitry 202 may be configured to deliver a plurality of control pulses, where the plurality of control pulses is interleaved with at least some informed pulses of the plurality of informed pulses. Stimulation generation circuitry may deliver the plurality of informed pulses and the plurality of control pulses to target tissue (e.g., spinal cord 120) of patient 105 via electrodes 232, 234 of leads 230. By delivering such informed pulses and control pulses, stimulation generation circuitry 202 may cause IMD 200 to sense stimulation signals that are indicative of the delivered pulses Additionally, or alternatively, stimulation generation circuitry 202 may deliver control pulses that evoke detectable responsive ECAPs in the target tissue, the responsive ECAPs propagating through the target tissue before arriving back at electrodes 232, 234. Stimulation signals or ECAPs caused by or elicited by informed pulses may not be detectable by IMD 200. In some examples, a different combination of electrodes 232, 234 may sense responsive ECAPs and/or responsive stimulation signals than a combination of electrodes 232, 234 that delivers informed pulses and a combination of electrodes 232, 234 that delivers control pulses. Sensing circuitry 206 may be configured to detect the responsive ECAPs and/or the responsive stimulation signals via electrodes 232, 234 and leads 230. In other examples, stimulation generation circuitry 202 may be configured to deliver a plurality of control pulses, without any informed pulses, when control pulses also provide or contribute to a therapeutic effect for the patient.

Processing circuitry 210 may, in some cases, direct sensing circuitry 206 to continuously monitor for ECAPs and stimulation signals. In other cases, processing circuitry 210 may direct sensing circuitry 206 to monitor for ECAPs and stimulation signals based on signals from sensor(s) 222. For example, processing circuitry 210 may activate sensing circuitry 206 based on an activity level of patient 105 exceeding an activity level threshold (e.g., acceleration sensor 223 rises above a threshold). Activating and deactivating sensing circuitry 206 may, in some examples, extend a battery life of power source 224.

Processing circuitry 210 may determine whether electrical stimulation therapy delivered to target tissue of patient 105 via electrodes 232, 234 elicits enough detectible ECAPs for processing circuitry 210 to determine therapy based on one or more characteristics of the respective detectible ECAPs. It may be beneficial for processing circuitry 210 to determine therapy based on characteristics of detectible ECAPs rather than characteristics of detectible stimulation signals, if possible. However, if not enough responsive ECAPs are detectible by sensing circuitry 206, it may be beneficial for processing circuitry 210 to determine therapy based on one or more characteristics of respective stimulation signals, which are often still detectible even when some or all of elicited ECAPs are not detectible in response to a stimulation pulse. In addition, sensing circuitry 206 may still detect stimulation signals when the delivered stimulation pulses were insufficient to elicit a detectable ECAP signal (e.g., when the stimulation pulses are configured to be sub-threshold pulses).

In one example, to determine if the electrical stimulation therapy elicits enough detectible ECAPs, processing circuitry 210 is configured to perform a test to determine whether the plurality of pulses of the electrical stimulation therapy elicit greater than a threshold ratio of detectible ECAPs. For example, to perform the test, processing circuitry 210 may identify a set of ECAPs elicited by a sequence of consecutive pulses of the plurality of pulses. Subsequently, processing circuitry 210 may calculate a ratio of the set of ECAPs to the sequence of consecutive pulses. For example, processing circuitry 210 may first determine a number of ECAPs of the set of ECAPs and a number of pulses of the sequence of consecutive pulses, and then calculate a ratio of the number of ECAPs to the number of pulses.

There may be cases in which a particular one or more stimulation pulses of the sequence of consecutive pulses might not elicit ECAPs that are detectible by sensing circuitry 206, but another one or more stimulation pulses of the sequence of consecutive pulses do elicit ECAPs that are detectible by sensing circuitry 206. In such cases, processing circuitry 210 may be configured to determine therapy based on one or more characteristics of the detectible ECAPs rather than determine therapy based on one or more characteristics of detectible stimulation signals. In some examples, processing circuitry 210 may determine whether the ratio of detectible ECAPs to stimulation pulses is greater than the threshold ratio. In one or more cases where the ratio is greater than the threshold ratio, processing circuitry 210 may determine therapy based on characteristics of the detectible ECAPs. In one or more cases where the ratio is not greater than the threshold ratio, processing circuitry 210 may determine therapy based on characteristics of the detectible stimulation signals.

In some examples, responsive to determining that a plurality of pulses elicit greater than a threshold ratio of detectible ECAPs, processing circuitry 210 is configured to set, based on one or more characteristics of an ECAP, one or more parameters which at least partially define the one or more pulses deliverable by stimulation generation circuitry 202 after a stimulation pulse which elicits the respective ECAP. In some examples, responsive to determining that a plurality of pulses do not elicit greater than a threshold ratio of detectible ECAPs, processing circuitry 210 is configured to set, based on one or more characteristics of a stimulation signal, one or more parameters which at least partially define the one or more pulses deliverable by stimulation generation circuitry 202 after a stimulation pulse which elicits the respective stimulation signal. In some examples, processing circuitry 210 may set one or more parameters which at least partially define the one or more pulses deliverable by stimulation generation circuitry 202 based on a combination of characteristics of one or more detectable ECAPs and characteristics of one or more detectible stimulation signals.

Stimulation generation circuitry 202 may be configured to deliver one or more stimulation pulses, at least one of which may cause sensing circuitry 206 to sense a stimulation signal in response to the delivery of the respective pulse. In some examples, to sense a stimulation signal, sensing circuitry 206 may detect, via any one or combination of electrodes 232, 234, one or more electrical signals which are generated by stimulation generation circuitry 202 and delivered to patient 105 via any one or combination of electrodes 232, 234. In some examples, stimulation signals may include information which is useful for determining one or more parameters of upcoming therapy pulses generated by stimulation generation circuitry 202. For example, information included by a stimulation signal may include one or more characteristics which indicate an efficacy of therapy delivered to patient 105 via electrodes 232, 234. In some cases, the one or more characteristics may reflect a separation between one or more of electrodes 232, 234 and target tissue of patient 105 (e.g., spinal cord 120). Such a distance between electrodes 232, 234 and spinal cord 120 may be relevant to determining therapy since a smaller intensity (e.g., amplitude and/or pulse length) of therapy pulses is required to stimulate a nerve if electrodes 232, 234 move closer to spinal cord 120 and vice versa.

Processing circuitry 210 may be configured to compare a characteristic value of a stimulation signal to a target stimulation signal value and adjust a stimulation parameter value based on the comparison. For example, processing circuitry may be configured to determine whether a characteristic value of a stimulation signal is within a range from a first threshold characteristic value to a second threshold characteristic value. In some examples, the characteristic value may include an amplitude of the stimulation signal, an amplitude of a portion of the stimulation signal, a slope of a portion of the stimulation signal, an area under a curve of at least a portion of the stimulation signal, or any combination thereof. In this way, sensing circuitry 206 may be configured to determine whether an amplitude of a portion of the stimulation signal is within a range from a first threshold amplitude value for the portion of the stimulation signal to a second threshold amplitude value for the portion of the stimulation signal, for example, but this is not required. The characteristic value may represent any measurable characteristic of a stimulation signal.

Responsive to determining that the characteristic value of the stimulation signal is not within a range from a first threshold characteristic value to a second threshold characteristic value, processing circuitry 210 may change one or more parameters which at least partially define one or more pulses deliverable by the stimulation generation circuitry after the stimulation signal as compared with the one or more parameters which at least partially define one or more pulses deliverable by the stimulation generation circuitry before the stimulation signal. In some examples, processing circuitry 210 may determine that the characteristic value is lower than the first threshold characteristic value.

In response to the characteristic value being lower than the first threshold characteristic value, processing circuitry 210 may be configured to increase (e.g., increment) one or more parameters which at least partially define one or more pulses deliverable by stimulation generation circuitry 202 after the stimulation signal (e.g., increase one or more parameters which define pulses of therapy stimulation programs 214 and/or test stimulation programs 216). In some examples, processing circuitry 210 may increase the one or more parameters proportional to an amount that the characteristic value is lower than the first threshold characteristic value. In some examples, processing circuitry 210 may increase the one or more parameters by a predetermined amount no matter the amount that the characteristic value is lower than the first threshold characteristic value. In some examples, processing circuitry 210 may increase the one or more parameters according to a function, where an input to the function is the characteristic value of the stimulation signal.

In response to the characteristic value being greater than the second threshold characteristic value, processing circuitry 210 may be configured to decrease (e.g., decrement) one or more parameters which at least partially define one or more pulses deliverable by stimulation generation circuitry 202 after the stimulation signal (e.g., decrease one or more parameters which define pulses of therapy stimulation programs 214 and/or test stimulation programs 216). In some examples, processing circuitry 210 may decrease the one or more parameters proportional to an amount that the characteristic value is greater than the second threshold characteristic value. In some examples, processing circuitry 210 may decrease the one or more parameters by a predetermined amount no matter the amount that the characteristic value is greater than the second threshold characteristic value. In some examples, processing circuitry 210 may decrease the one or more parameters according to a function, where an input to the function is the characteristic value of the stimulation signal.

Processing circuitry 210 may maintain one or more parameters of which at least partially define one or more pulses deliverable by stimulation generation circuitry 202 after a respective stimulation signal responsive to determining that a value of a characteristic of the stimulation signal is within a range from a first threshold characteristic value to a second threshold characteristic value. For example, if the characteristic of the stimulation signal is within the range, this may indicate that the one or more parameters which at least partially define one or more pulses deliverable by stimulation generation circuitry 202 are within a desired range.

A characteristic value of a stimulation signal may, in some cases, depend on one or more parameters of the delivered pulse (e.g., pulse amplitude, pulse duration, area under a curve of the pulse, pulse shape, pulse slope, or any combination thereof) from which sensing circuitry 206 detects one or more stimulation signal. For example, determining therapy based on a stimulation signal may, in some cases, depend on an amplitude of the pulse which causes sensing circuitry 206 to detect the stimulation signal. This is because sensing circuitry 206 senses stimulation signals by detecting electrical signals indicative of stimulation pulses delivered by electrodes 232, 234. In this way, it may be expected that a first stimulation pulse having a first amplitude will cause sensing circuitry 206 to detect a stimulation signal having an amplitude within a first range of amplitude values. Additionally, it may be expected that a second stimulation pulse having a second amplitude will cause sensing circuitry 206 to detect a stimulation signal having an amplitude within a second range of amplitude values. If the first amplitude of the first stimulation pulse is lower than the second amplitude of the second stimulation pulse, a lower-bound of the first range may be lower than a lower-bound of the second range and an upper-bound of the first range may be lower than an upper-bound of the second range. In some examples, a range of target amplitude values for a stimulation signal may be linearly related to an amplitude of a stimulation pulse which causes sensing circuitry 206 to detect the stimulation signal. Storage device 212 may store target values 218 which include a set of target ranges and other target values, where each target range and target value of target values 218 corresponds to a respective stimulation pulse amplitude value of a set of stimulation pulse amplitude values.

Determining therapy based on one or more stimulation signals may, in some cases, depend on a posture of patient 105. For example, processing circuitry 210 may be configured to determine a posture of patient 105 based on an acceleration signal generated by acceleration sensor 223. In some examples, the accelerometer signal includes a vertical component, a lateral component, and a frontal component corresponding to a vertical axis, a lateral axis, and a frontal axis, respectively. In this way, the accelerometer signal represents a three-dimensional measurement of acceleration. It may be beneficial for processing circuitry 210 to analyze one or more of the vertical axis, the lateral axis, and the frontal axis in order to determine a posture of patient 105.

In some examples, acceleration sensor 223 is configured to generate an accelerometer signal. Processing circuitry 210 is configured to identify, based on the accelerometer signal, a posture of a set of postures which patient 105 is occupying. The set of postures may include, for example, a standing posture, a sitting posture, a supine posture, a prone posture, a side-lying posture, or any combination thereof. In some examples, expected parameter values of the accelerometer signal corresponding to each posture of the set of postures are stored in storage device 212. Subsequently, processing circuitry 210 may select, based on the identified posture, a target stimulation signal value (e.g., a target range of characteristic values) for a stimulation signal sensed by IMD 200 in response to a delivery of a corresponding stimulation pulses. For example, if stimulation generation circuitry 202 generates a stimulation pulse having a stimulation amplitude and delivers the stimulation pulse to target tissue of patient 105 via one or a combination of electrodes 232, 234, processing circuitry 210 may select, based on a posture of patient 105 during the delivery of the stimulation pulse, a target range for a characteristic of the resulting stimulation signal sensed by sensing circuitry 106. Subsequently, processing circuitry 210 may determine whether to change one or more parameters of therapy stimulation programs 314 and/or test stimulation programs 216 based on whether the characteristic value is within the target range of characteristic values selected based on the posture of patient 105.

In some examples, processing circuitry 210 is configured to identify, based on the accelerometer signal, a posture of a set of postures which patient 105 is occupying while a stimulation pulse is delivered and identify an amplitude of the stimulation pulse. Subsequently, processing circuitry 210 may select a target range of characteristic values for a characteristic of a stimulation signal sensed by sensing circuitry 206 in response to the delivery of the stimulation pulse based on both of the posture of patient 105 and the amplitude of the stimulation pulse. For example, target values 218 may include a respective transfer function corresponding to each posture of the set of postures. Each transfer function represents a relationship (e.g., a linear relationship) between the amplitude of a stimulation pulse and the target stimulation signal value (e.g., a target range of characteristic values) for a stimulation signal sensed by IMD 200 in response to the delivery of the stimulation pulse. As such, processing circuitry 210 may, when evaluating whether to change one or more parameters of upcoming stimulation pulses, first select a transfer function corresponding to a present stimulation pulse and subsequently select a target range of characteristics based on the amplitude of the present stimulation pulse, but this is not required. Processing circuitry 210 may first analyze the amplitude of the stimulation pulse and subsequently determine the posture of patient 105, in some cases.

In some examples, processing circuitry 210 is configured to determine, based on the accelerometer signal generated by acceleration sensor 223, a transition from a first posture to a second posture of the set of postures. Responsive to determining the transition from the first posture to the second posture, processing circuitry 210 is configured to update the target stimulation signal value (e.g., the target range of characteristic values) for a respective sensed stimulation signal from a first target stimulation signal value to a second target stimulation signal value. In some examples, the detected change in posture may trigger the transition from a first target range to a second target range, but this is not required. In some cases, processing circuitry 102 may monitor the posture of patient 105 and the amplitude of stimulation pulses generated by stimulation generation circuitry 202 in real time or near real-time. Accordingly, processing circuitry 210 may set the range of target characteristic values for responsive stimulation signals in real time or near real-time.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
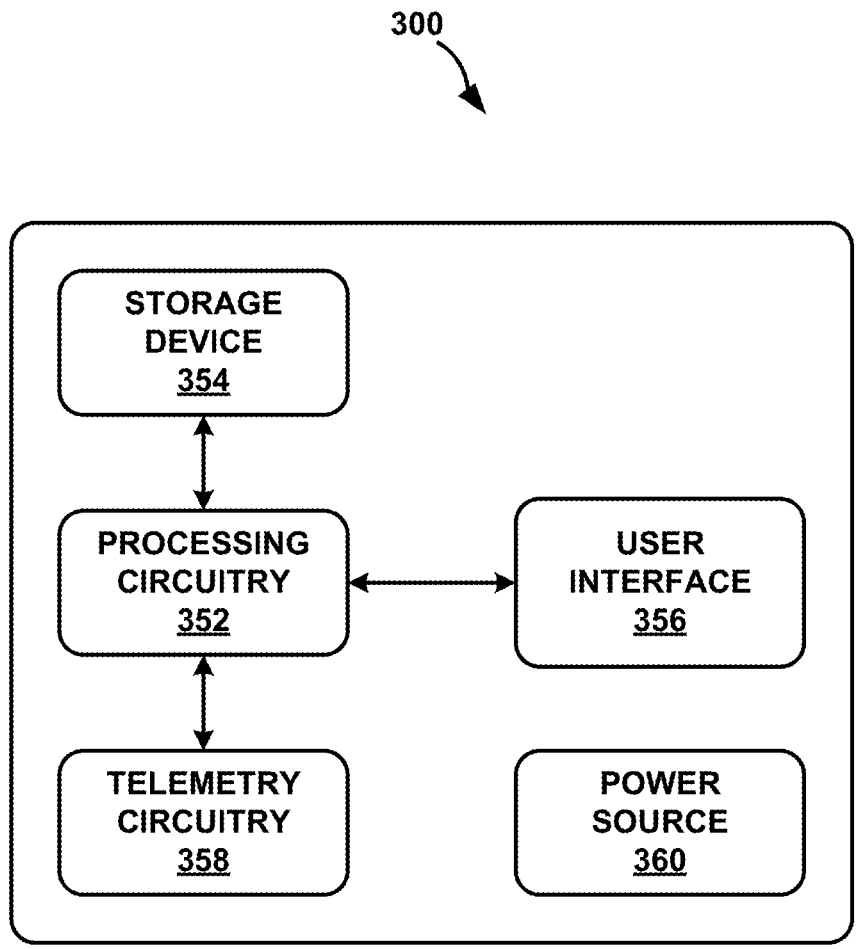
FIG. 3 is a block diagram illustrating an example configuration of components of the external programmer of FIG. 1, in accordance with one or more techniques of this disclosure.

FIG. 3 is a block diagram illustrating an example configuration of components of external programmer 300, in accordance with one or more techniques of this disclosure. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode movement pattern, or receive a user input and send a corresponding command to IMD 200, or instructions for any other functionality. In addition, storage device 354 may include a plurality of programs, where each program includes a parameter set that defines stimulation pulses, such as control pulses and/or informed pulses. Storage device 354 may also store data received from a medical device (e.g., IMD 110). For example, storage device 354 may store stimulation signal and/or ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified patient behaviors, sensed patient parameter values, patient behavior criteria, or any other such information. User interface 356 may also receive user input via user interface 356. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

According to the techniques of the disclosure, user interface 356 of external programmer 300 receives an indication from a clinician instructing a processor of the medical device to update one or more therapy stimulation programs or to update one or more test stimulation programs. Updating therapy stimulation programs and test stimulation programs may include changing one or more parameters of the stimulation pulses delivered by the medical device according to the programs, such as amplitude, pulse width, frequency, and pulse shape of the informed pulses and/or control pulses. User interface 356 may also receive instructions from the clinician commanding any electrical stimulation, including control pulses and/or informed pulses to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

Figure 4:
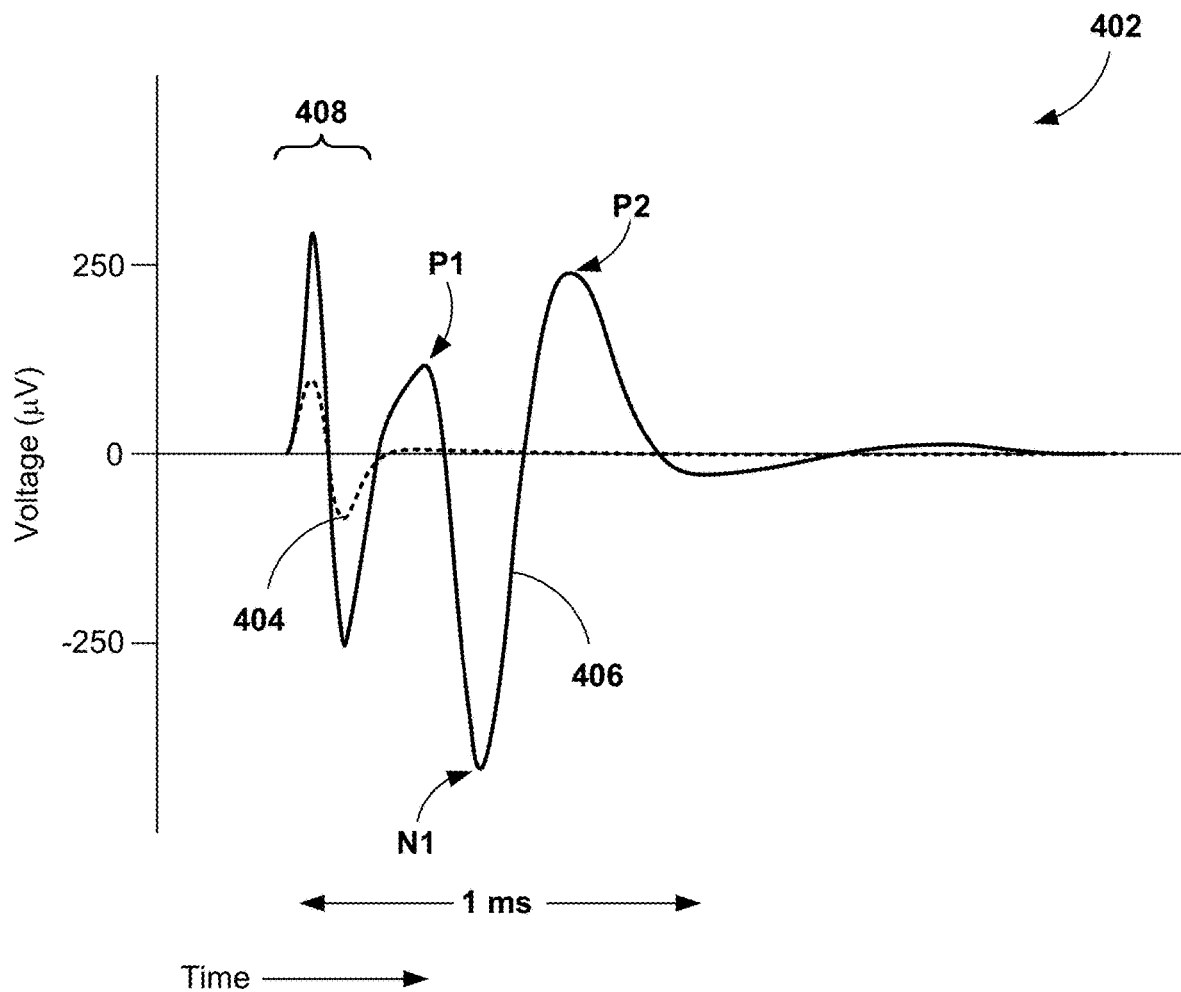
FIG. 4 is a graph 402 of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from stimulation pulses (e.g., a control pulse) that were delivered from a guarded cathode, where the stimulation pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse, or a stimulation pulse which results in no detectable ECAP. It is noted that monophasic, tri-phasic, or pulses with another quantity of phases may be in other examples.

Peaks 408 of ECAP signal 404 are detected and represent stimulation signals of the delivered stimulation pulse. However, no propagating signal is detected after the stimulation signal in ECAP signal 404 because the stimulation pulse had an intensity (e.g., an amplitude and/or pulse width) that was "sub-threshold" or below a detection threshold (e.g., a sub-detection threshold) and/or below a propagation threshold (e.g., a sub-propagation threshold).

In contrast to ECAP signal 404, ECAP signal 406 represents the voltage amplitude detected from a supra-detection stimulation threshold stimulation pulse. Peaks 408 of ECAP signal 406 are detected and represent stimulation signals of the delivered stimulation pulse. After peaks 408, ECAP signal 406 also includes peaks P1, N1, and P2, which are three typical peaks representative of propagating action potentials from an ECAP. The example duration of the stimulation signal and peaks P1, N1, and P2 is approximately 1 millisecond (ms).

When detecting the ECAP of ECAP signal 406, different characteristics may be identified. For example, the characteristic of the ECAP may be the amplitude between N1 and P2. This N1-P2 amplitude may be easily detectable even if the stimulation signal impinges on P1, a relatively large signal, and the N1-P2 amplitude may be minimally affected by electronic drift in the signal. In other examples, the characteristic of the ECAP used to control subsequent stimulation pulses (e.g., control pulses and/or informed pulses) may be an amplitude of P1, N1, or P2 with respect to neutral or zero voltage. In some examples, the characteristic of the ECAP used to control subsequent stimulation pulses is a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two points in the ECAP signal, such as the slope between N1 and P2. In other examples, the characteristic of the ECAP may be the time between two points of the ECAP, such as the time between N1 and P2.

The time between when the stimulation pulse is delivered and a point in the ECAP signal may be referred to as a latency of the ECAP and may indicate the types of fibers being captured by the stimulation pulse (e.g., a control pulse). ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Latency may also refer to the time between an electrical feature is detected at one electrode and then detected again at a different electrode. This time, or latency, is inversely proportional to the conduction velocity of the nerve fibers. Other characteristics of the ECAP signal may be used in other examples.

The amplitude of the ECAP signal increases with increased amplitude of the stimulation pulse, as long as the pulse amplitude is greater than threshold such that nerves depolarize and propagate the signal. The target ECAP characteristic (e.g., the target ECAP amplitude) may be determined from the ECAP signal detected from a stimulation pulse (or a control pulse) when informed pulses are determined to deliver effective therapy to patient 105. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change therapy pulse parameter values and maintain the target ECAP characteristic value during therapy pulse delivery.

Figure 5A:
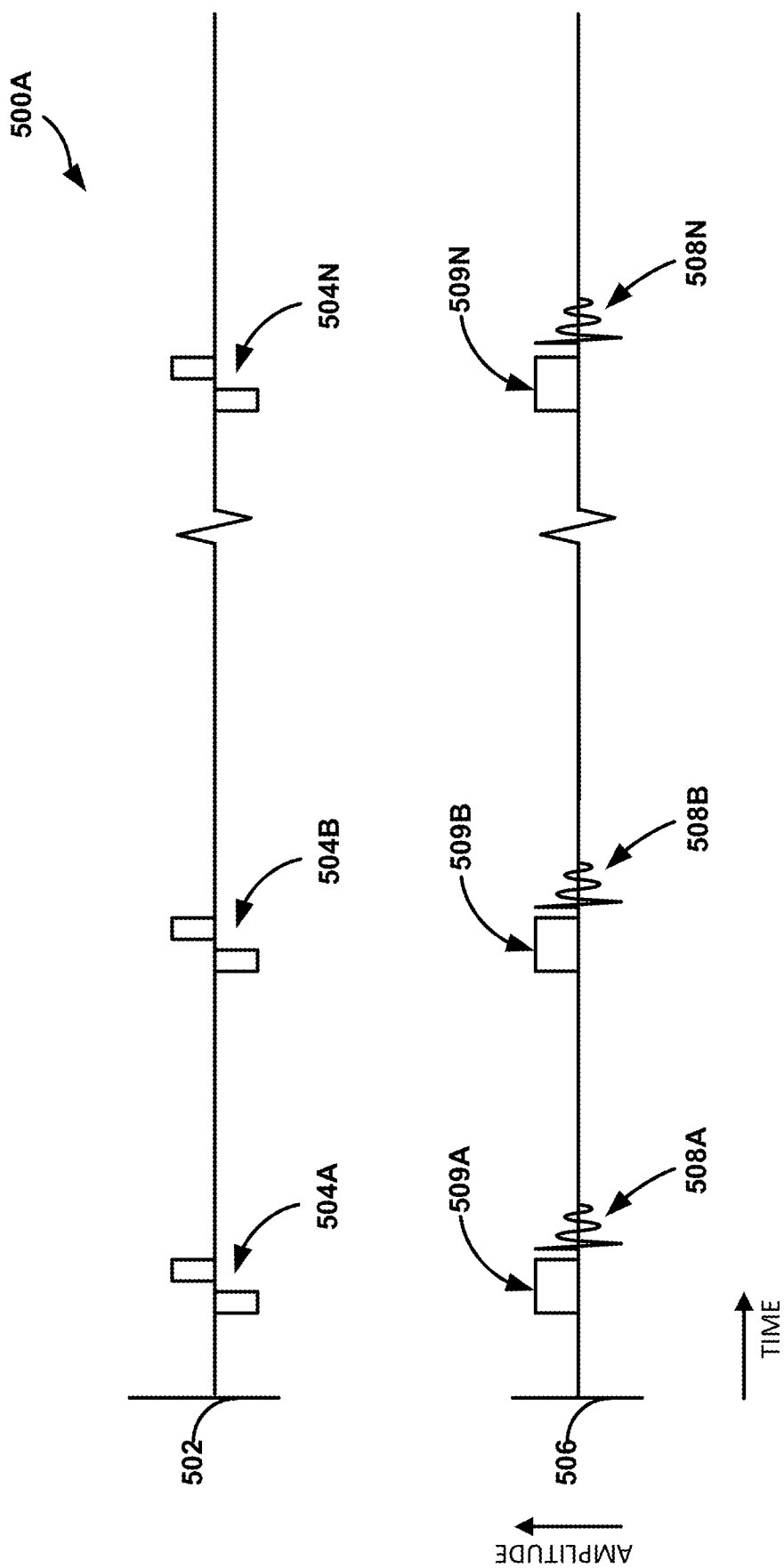
FIG. 5A is an example timing diagram illustrating an example of electrical stimulation pulses, respective stimulation signals, and respective sensed ECAPs, in accordance with one or more techniques of this disclosure.

FIG. 5A is a timing diagram 500A illustrating an example of electrical stimulation pulses, respective stimulation signals, and respective sensed ECAPs, in accordance with one or more techniques of this disclosure. For convenience, FIG. 5A is described with reference to IMD 200 of FIG. 2. As illustrated, timing diagram 500A includes first channel 502, a plurality of stimulation pulses 504A-504N (collectively "stimulation pulses 504"), second channel 506, a plurality of respective ECAPs 508A-508N (collectively "ECAPs 508"), and a plurality of stimulation signals 509A-509N (collectively "stimulation signals 509"). In some examples, stimulation pulses 504 may represent control pulses which are configured to elicit ECAPs 508 that are detectible by IMD 200, but this is not required. Stimulation pulses 504 may represent any type of pulse that is deliverable by IMD 200. In the example of FIG. 5A, IMD 200 can deliver therapy with control pulses instead of, or without, informed pulses.

First channel 502 is a time/voltage (and/or current) graph indicating the voltage (or current) of at least one electrode of electrodes 232, 234. In one example, the stimulation electrodes of first channel 502 may be located on the opposite side of the lead as the sensing electrodes of second channel 506. Stimulation pulses 504 may be electrical pulses delivered to the spinal cord of the patient by at least one of electrodes 232, 234, and stimulation pulses 504 may be balanced biphasic square pulses with an interphase interval. In other words, each of stimulation pulses 504 are shown with a negative phase and a positive phase separated by an interphase interval. For example, a stimulation pulse 504 may have a negative voltage for the same amount of time and amplitude that it has a positive voltage. It is noted that the negative voltage phase may be before or after the positive voltage phase. Stimulation pulses 504 may be delivered according to test stimulation programs 216 stored in storage device 212 of IMD 200, and test stimulation programs 216 may be updated according to user input via an external programmer and/or may be updated according to a signal from sensor(s) 222. In one example, stimulation pulses 504 may have a pulse width of less than approximately 300 microseconds (e.g., the total time of the positive phase, the negative phase, and the interphase interval is less than 300 microseconds). In another example, stimulation pulses 504 may have a pulse width of approximately 100 us for each phase of the bi-phasic pulse. As illustrated in FIG. 5A, stimulation pulses 504 may be delivered via channel 502. Delivery of stimulation pulses 504 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 506 is a time/voltage (and/or current) graph indicating the voltage (or current) of at least one electrode of electrodes 232, 234. In one example, the electrodes of second channel 506 may be located on the opposite side of the lead as the electrodes of first channel 502. ECAPs 508 may be sensed at electrodes 232, 234 from the spinal cord of the patient in response to stimulation pulses 504. ECAPs 508 are electrical signals which may propagate along a nerve away from the origination of stimulation pulses 504. In one example, ECAPs 508 are sensed by different electrodes than the electrodes used to deliver stimulation pulses 504. As illustrated in FIG. 5A, ECAPs 508 may be recorded on second channel 506.

Stimulation signals 509A, 509B, and 509N may be sensed by leads 230 and sensing circuitry 206 and may be sensed during the same period of time as the delivery of stimulation pulses 504. Since the stimulation signals may have a greater amplitude and intensity than ECAPs 508, any ECAPs arriving at IMD 200 during the occurrence of stimulation signals 509 might not be adequately sensed by sensing circuitry 206 of IMD 200. However, ECAPs 508 may be sufficiently sensed by sensing circuitry 206 because each ECAP 508, or at least a portion of ECAP 508 used as feedback for stimulation pulses 504, falls after the completion of each a stimulation pulse 504. As illustrated in FIG. 5A, stimulation signals 509 and ECAPs 508 may be recorded on channel 506. In some examples, ECAPs 508 may not follow respective stimulation signals 509 when ECAPs are not elicited by stimulation pulses 504 or the amplitude of ECAPs is too low to be detected (e.g., below the detection threshold).

Figure 5B:
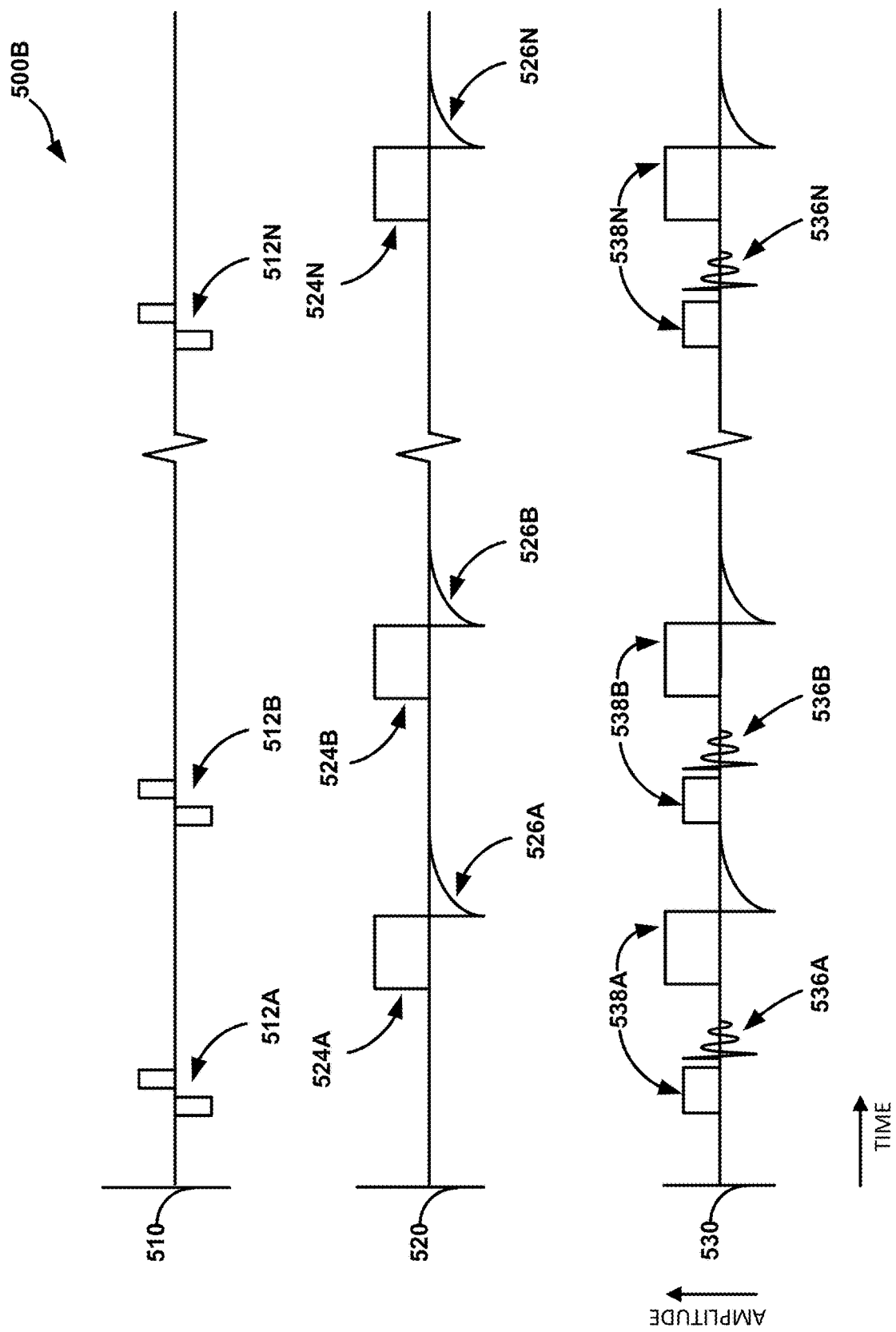
FIG. 5B is another example timing diagram illustrating an example of electrical stimulation pulses, respective stimulation signals, and respective sensed ECAPs, in accordance with one or more techniques of this disclosure.

FIG. 5B is a timing diagram 500B illustrating one example of electrical stimulation pulses, respective stimulation signals, and respective sensed ECAPs, in accordance with one or more techniques of this disclosure. For convenience, FIG. 5B is described with reference to IMD 200 of FIG. 2. As illustrated, timing diagram 500B includes first channel 510, a plurality of control pulses 512A-512N (collectively "control pulses 512"), second channel 520, a plurality of informed pulses 524A-524N (collectively "informed pulses 524") including passive recharge phases 526A-526N (collectively "passive recharge phases 526"), third channel 530, a plurality of respective ECAPs 536A-536N (collectively "ECAPs 536"), and a plurality of stimulation signals 538A-538N (collectively "stimulation signals 538").

First channel 510 is a time/voltage (and/or current) graph indicating the voltage (or current) of at least one electrode of electrodes 232, 234. In one example, the stimulation electrodes of first channel 510 may be located on the opposite side of the lead as the sensing electrodes of third channel 530. Control pulses 512 may be electrical pulses delivered to the spinal cord of the patient by at least one of electrodes 232, 234, and control pulses 512 may be balanced biphasic square pulses with an interphase interval. In other words, each of control pulses 512 are shown with a negative phase and a positive phase separated by an interphase interval. For example, a control pulse 512 may have a negative voltage for the same amount of time that it has a positive voltage. It is noted that the negative voltage phase may be before or after the positive voltage phase. Control pulses 512 may be delivered according to test stimulation programs 216 stored in storage device 212 of IMD 200, and test stimulation programs 216 may be updated according to user input via an external programmer and/or may be updated according to a signal from sensor(s) 222. In one example, control pulses 512 may have a pulse width of less than approximately 300 microseconds (e.g., the total time of the positive phase, the negative phase, and the interphase interval is less than 300 microseconds). In another example, control pulses 512 may have a pulse width of approximately 100 us for each phase of the bi-phasic pulse. As illustrated in FIG. 5B, control pulses 512 may be delivered via first channel 510. Delivery of control pulses 512 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 520 is a time/voltage (and/or current) graph indicating the voltage (or current) of at least one electrode of electrodes 232, 234 for the informed pulses. In one example, the electrodes of second channel 520 may partially or fully share common electrodes with the electrodes of first channel 510 and third channel 530. Informed pulses 524 may also be delivered by the same leads 230 that are configured to deliver control pulses 512. Informed pulses 524 may be interleaved with control pulses 512, such that the two types of pulses are not delivered during overlapping periods of time. However, informed pulses 524 may or may not be delivered by exactly the same electrodes that deliver control pulses 512. Informed pulses 524 may be monophasic pulses with pulse widths of greater than approximately 300 us and less than approximately 1000 μs. In fact, informed pulses 524 may be configured to have longer pulse widths than control pulses 512. As illustrated in FIG. 5B, informed pulses 524 may be delivered on second channel 520.

Informed pulses 524 may be configured for passive recharge. For example, each informed pulse 524 may be followed by a passive recharge phase 526 to equalize charge on the stimulation electrodes. Unlike a pulse configured for active recharge, where remaining charge on the tissue following a stimulation pulse is instantly removed from the tissue by an opposite applied charge, passive recharge allows tissue to naturally discharge to some reference voltage (e.g., ground or a rail voltage) following the termination of the therapy pulse. In some examples, the electrodes of the medical device may be grounded at the medical device body. In this case, following the termination of informed pulse 524, the charge on the tissue surrounding the electrodes may dissipate to the medical device, creating a rapid decay of the remaining charge at the tissue following the termination of the pulse. This rapid decay is illustrated in passive recharge phases 526. Passive recharge phase 526 may have a duration in addition to the pulse width of the preceding informed pulse 524. In other examples (not pictured in FIG. 5B), informed pulses 524 may be bi-phasic pulses having a positive and negative phase (and, in some examples, an interphase interval between each phase) which may be referred to as pulses including active recharge. An informed pulse that is a bi-phasic pulse may or may not have a following passive recharge phase.

Third channel 530 is a time/voltage (and/or current) graph indicating the voltage (or current) of at least one electrode of electrodes 232, 234. In one example, the electrodes of third channel 530 may be located on the opposite side of the lead as the electrodes of first channel 510. ECAPs 536 may be sensed at electrodes 232, 234 from the spinal cord of the patient in response to control pulses 512. ECAPs 536 are electrical signals which may propagate along a nerve away from the origination of control pulses 512. In one example, ECAPs 536 are sensed by different electrodes than the electrodes used to deliver control pulses 512. As illustrated in FIG. 5B, ECAPs 536 may be recorded on third channel 530.

Stimulation signals 538A, 538B, and 538N may be sensed by leads 230 and may be sensed during the same period of time as the delivery of control pulses 512 and informed pulses 524. Since the stimulation signals may have a greater amplitude and intensity than ECAPs 536, any ECAPs arriving at IMD 200 during the occurrence of stimulation signals 538 may not be adequately sensed by sensing circuitry 206 of IMD 200. However, ECAPS 536 may be sufficiently sensed by sensing circuitry 206 because each ECAP 536 falls after the completion of each a control pulse 512 and before the delivery of the next informed pulse 524. As illustrated in FIG. 5B, stimulation signals 538 and ECAPs 536 may be recorded on channel 530.

Figure 6A:
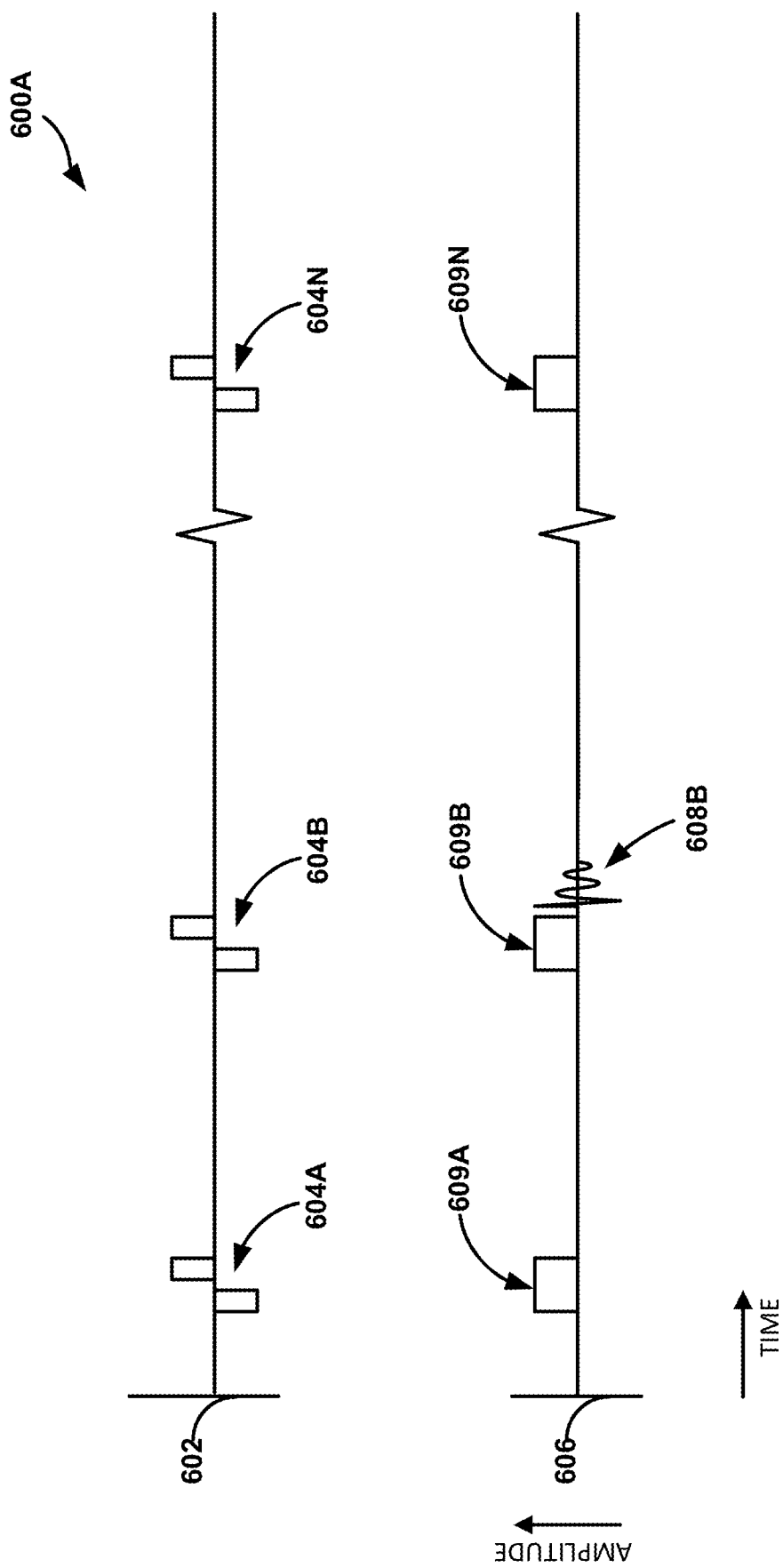
FIG. 6A is another example timing diagram illustrating an example of electrical stimulation pulses, respective stimulation signals, and respective sensed ECAPs, in accordance with one or more techniques of this disclosure.

FIG. 6A is a timing diagram 600A illustrating an example of electrical stimulation pulses, respective stimulation signals, and respective sensed ECAPs, in accordance with one or more techniques of this disclosure. For convenience, FIG. 6A is described with reference to IMD 200 of FIG. 2. As illustrated, timing diagram 600A includes first channel 602, a plurality of stimulation pulses 604A-604N (collectively "stimulation pulses 604"), second channel 606, a plurality of respective ECAPs 608A-608N (collectively "ECAPs 608"), and a plurality of stimulation signals 609A-609N (collectively "stimulation signals 609"). In some examples, stimulation pulses 604 may represent control pulses which are configured to elicit ECAPs 608 that are detectible by IMD 200, but this is not required. Stimulation pulses 604 may represent any type of pulse that is deliverable by IMD 200. In the example of FIG. 6A, IMD 200 can deliver therapy with control pulses instead of, or without, informed pulses.

Timing diagram 600A of FIG. 6A may be substantially the same as timing diagram 500A FIG. 5A except that stimulation pulse 604A and stimulation pulse 604N do not evoke an ECAP that is detectible by IMD 200. Although stimulation pulse 604B emits ECAP 608B, which is detectible by IMD 200, it may be the case that IMD 200 does not sense enough detectible ECAPs for therapy determination in the example of FIG. 6A. As such, IMD 200 may determine one or more characteristics of stimulation signals 609 in order to determine one or more parameters of upcoming stimulation pulses following stimulation pulse 604N. For example, IMD 200 may determine an amplitude of at least a portion of each stimulation signal of stimulation signals 609 and determine the one or more parameters of the upcoming stimulation pulses based on the determined amplitudes. Although stimulation signals 609 are illustrated as square pulses, stimulation signals 609 may include other shapes and/or waveforms, in some examples. In some examples, each stimulation signal of stimulation signals 509 may include two or more phases. Processing circuitry 210 of IMD 200 may analyze the two or more phases of stimulation signals 509 in order to determine therapy.

Figure 6B:
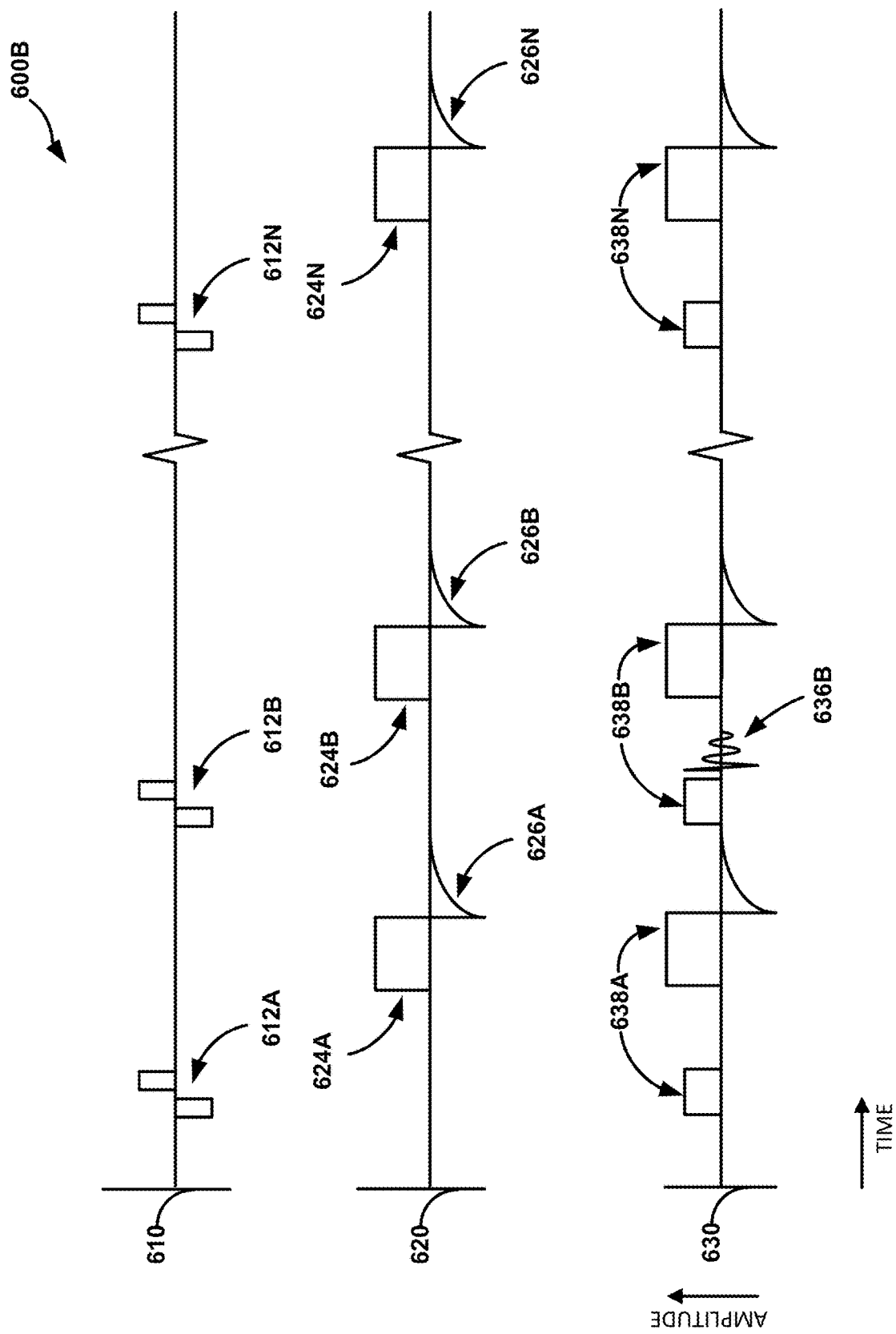
FIG. 6B is another example timing diagram illustrating one example of electrical stimulation pulses, respective stimulation signals, and respective sensed ECAPs, in accordance with one or more techniques of this disclosure.

FIG. 6B is a timing diagram 600B illustrating one example of electrical stimulation pulses, respective stimulation signals, and respective sensed ECAPs, in accordance with one or more techniques of this disclosure. For convenience, FIG. 6B is described with reference to IMD 200 of FIG. 2. As illustrated, timing diagram 600B includes first channel 610, a plurality of control pulses 612A-612N (collectively "control pulses 612"), second channel 620, a plurality of informed pulses 624A-624N (collectively "informed pulses 624") including passive recharge phases 626A-626N (collectively "passive recharge phases 626"), third channel 630, a plurality of respective ECAPs 636A-636N (collectively "ECAPs 636"), and a plurality of stimulation signals 638A-638N (collectively "stimulation signals 638").

Timing diagram 600B of FIG. 6B may be substantially the same as timing diagram 500B FIG. 5B except that control pulse 612A and control pulse 612N do not evoke an ECAP that is detectible by IMD 200. Although control pulse 612B emits ECAP 636B, which is detectible by IMD 200, it may be the case that IMD 200 does not sense enough detectible ECAPs for therapy determination in the example of FIG. 6B. As such, IMD 200 may determine one or more characteristics of stimulation signals 638 in order to determine one or more parameters of upcoming stimulation pulses following control pulse 612N. For example, IMD 200 may determine an amplitude of at least a portion of each stimulation signal of stimulation signals 638 and determine the one or more parameters of the upcoming stimulation pulses based on the determined amplitudes. Although stimulation signals 638 are illustrated as square pulses, stimulation signals 639 may include other shapes and/or waveforms, in some examples. In some examples, each stimulation signal of stimulation signals 638 may include two or more phases. Processing circuitry 210 of IMD 200 may analyze the two or more phases of stimulation signals 638 in order to determine therapy.

Figure 7:
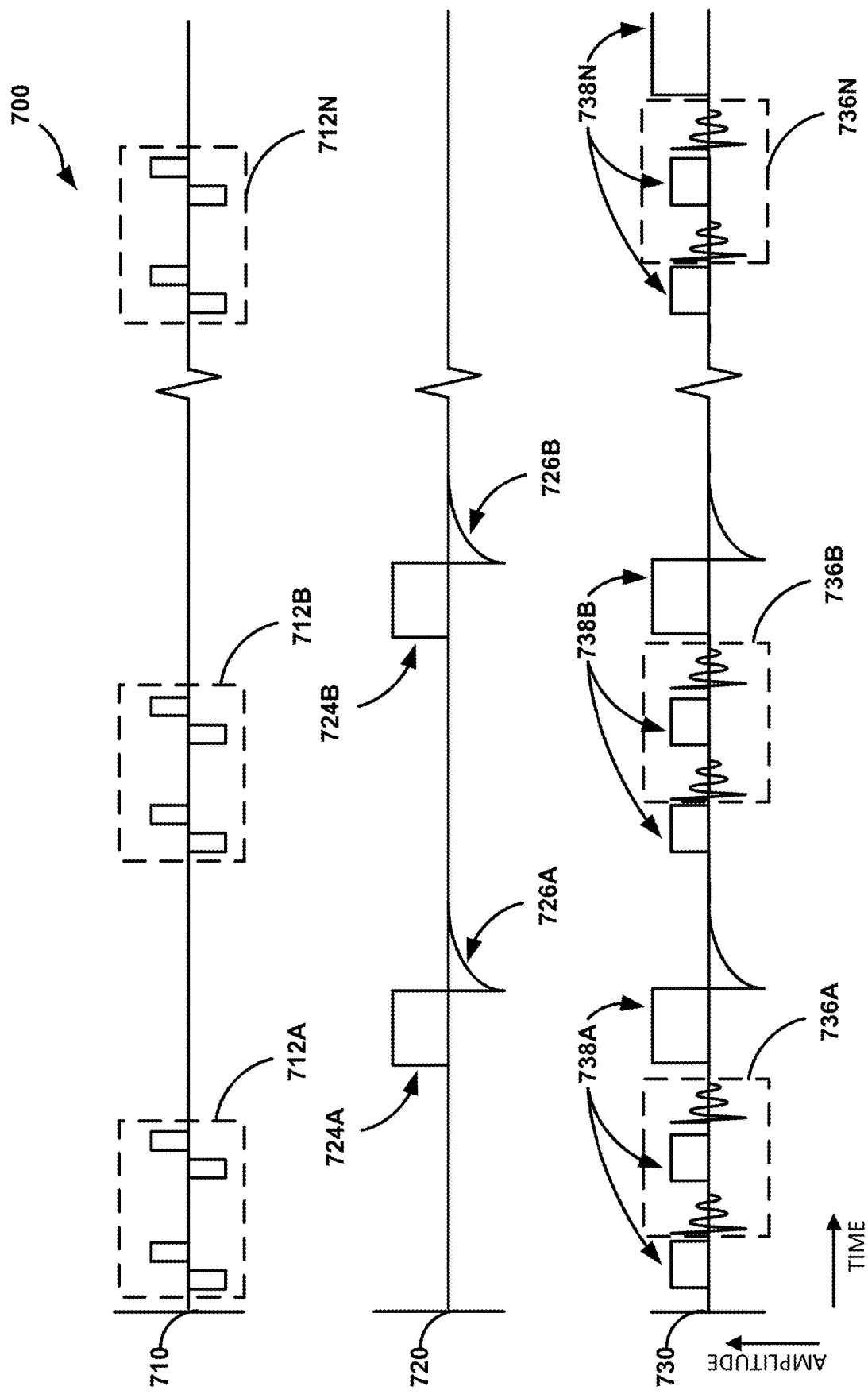
FIG. 7 is another example timing diagram illustrating an example of electrical stimulation pulses, respective stimulation signals, and respective ECAPs, in accordance with one or more techniques of this disclosure.

FIG. 7 is a timing diagram 700 illustrating another example of electrical stimulation pulses, respective stimulation signals, and respective ECAPs, in accordance with one or more techniques of this disclosure. For convenience, FIG. 7 is described with reference to IMD 200 of FIG. 2. As illustrated, timing diagram 700 includes first channel 710, a plurality of control pulses 712A-712N (collectively "control pulses 712"), second channel 720, a plurality of informed pulses 724A-724B (collectively "informed pulses 724") including passive recharge phases 726A-726B (collectively "passive recharge phases 726"), third channel 730, a plurality of respective ECAPs 736A-736N (collectively "ECAPs 736"), and a plurality of stimulation interference signals 738A-738N (collectively "stimulation interference signals 738"). FIG. 7 may be substantially similar to FIG. 5B, except for the differences detailed below.

Two or more (e.g. two) control pulses 712 may be delivered during each time event (e.g., window) of a plurality of time events, and each time event represents a time between two consecutive informed pulses 724. For example, during each time event, a first control pulse may be directly followed by a first respective ECAP, and subsequent to the completion of the first respective ECAP, a second control pulse may be directly followed by a second respective ECAP. Informed pulses may commence following the second respective ECAP. In other examples not illustrated here, three or more control pulses 712 may be delivered, and respective ECAP signals sensed, during each time event of the plurality of time events.

Figure 8:
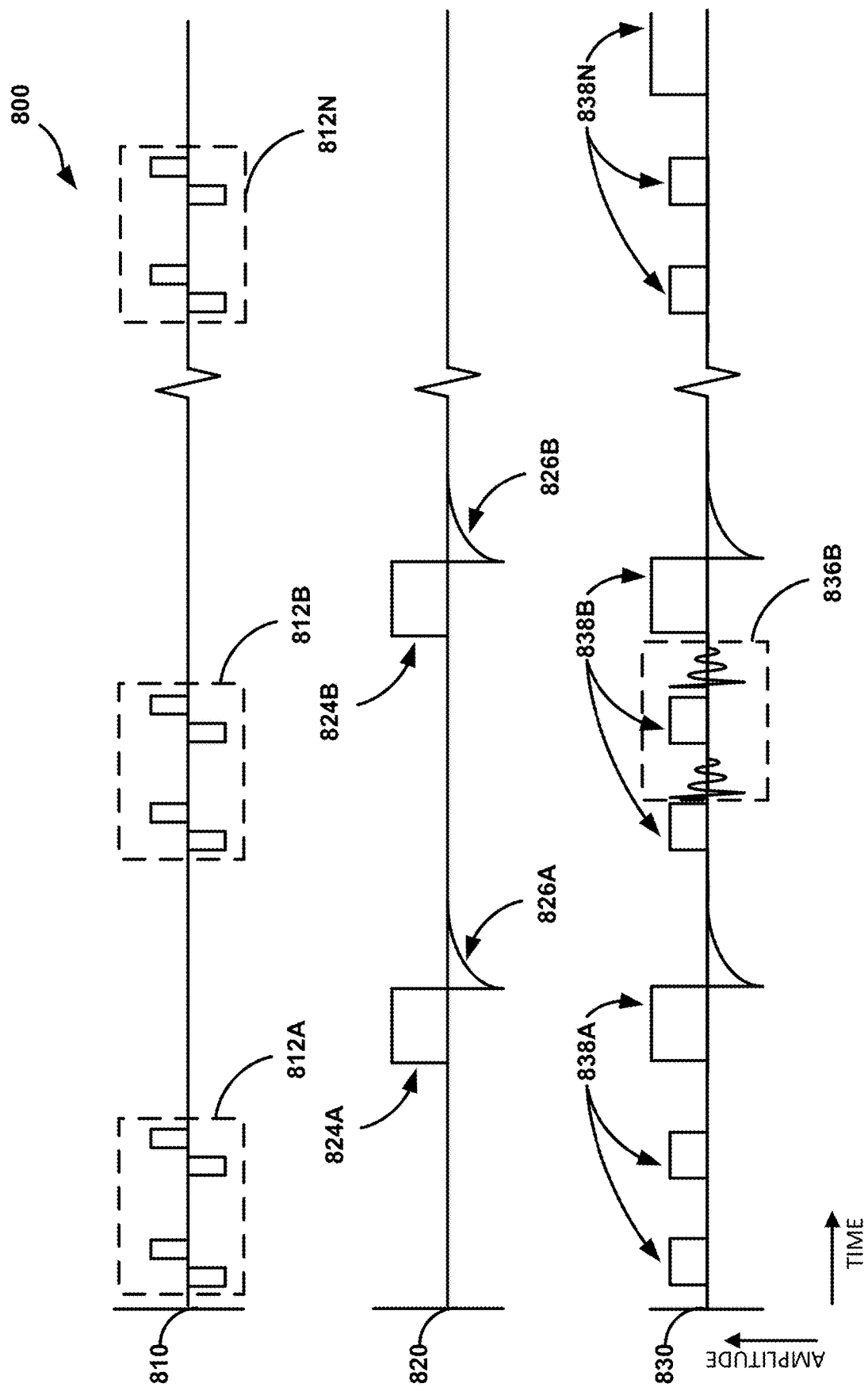
FIG. 8 is another example timing diagram illustrating an example of electrical stimulation pulses, respective stimulation signals, and respective ECAPs, in accordance with one or more techniques of this disclosure.

FIG. 8 is a timing diagram 800 illustrating another example of electrical stimulation pulses, respective stimulation signals, and respective ECAPs, in accordance with one or more techniques of this disclosure. For convenience, FIG. 8 is described with reference to IMD 200 of FIG. 2. As illustrated, timing diagram 800 includes first channel 810, a plurality of control pulses 812A-812N (collectively "control pulses 812"), second channel 820, a plurality of informed pulses 824A-824B (collectively "informed pulses 824") including passive recharge phases 826A-826B (collectively "passive recharge phases 826"), third channel 830, respective ECAPs 836B (collectively "ECAPs 836"), and a plurality of stimulation interference signals 838A-838N (collectively "stimulation interference signals 838"). Timing diagram 800 of FIG. 8 may be substantially the same as timing diagram 700 FIG. 7 except that control pulses 812A and control pulses 812N do not evoke ECAPs that are detectible by IMD 200. Although control pulses 812B emit ECAPs 836B, which are detectible by IMD 200, it may be the case that IMD 200 does not sense enough detectible ECAPs for therapy determination in the example of FIG. 8.

As such, IMD 200 may determine one or more characteristics of stimulation signals 838 in order to determine one or more parameters of upcoming stimulation pulses following control pulses 812N.

Figure 9:
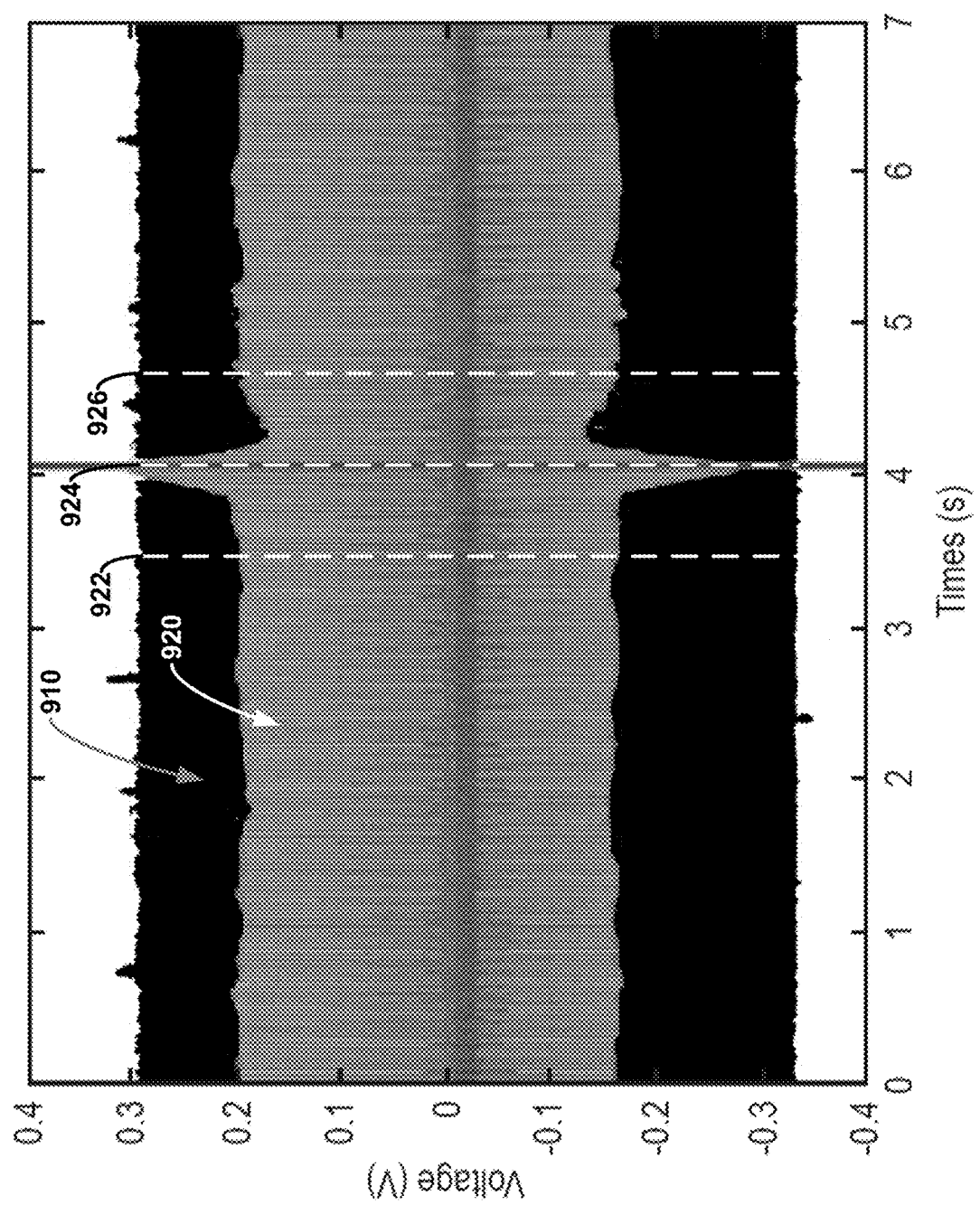
FIG. 9 is a graph illustrating a stimulation pulse amplitude plot and a stimulation signal amplitude plot, in accordance with one or more techniques of this disclosure.

FIG. 9 is a graph 900 illustrating a stimulation pulse amplitude plot 910 and a stimulation signal amplitude plot 920, in accordance with one or more techniques of this disclosure. Additionally, graph 900 indicates a first time 922, a second time 924, and a third time 926. FIG. 9 is described with reference to IMD 200 of FIG. 2.

Stimulation pulse amplitude plot 910 may represent a plot of respective amplitudes of a set of consecutive stimulation pulses delivered by IMD 200. As seen, if FIG. 9, each stimulation pulse of the set of stimulation pulses may include a substantially similar amplitude. Stimulation signal amplitude plot 920, however, indicates a patient event occurring between first time 922 and third time 926 where the amplitudes of responsive stimulation signals increases sharply before settling at a baseline value at third time 926. In some examples, the patient event may represent a cough, a sneeze, a posture movement, or another action. In any case, the patient event may represent an occurrence between first time 922 and third time 926 in which a distance between one or more of electrodes 232, 234 of IMD 200 and target tissue (e.g., spinal cord 120) of patient 105 decreases as compared with a baseline distance. The distance between the one or more of electrodes 232, 234 of IMD 200 and the target tissue may return to the baseline distance at third time 926. Second time 924 may indicate a time in which a peak in stimulation signal amplitude occurs.

In some examples, it may be beneficial for processing circuitry 210 to set one or more parameters of stimulation pulses delivered by IMD 200 based on detecting the patient event between first time 922 and third event 926. In some examples, although not illustrated in FIG. 9, processing circuitry 210 may decrease an amplitude of one or more therapy pulses delivered by IMD 200 between first time 922 and third time 926 in order to decrease a probability that patient 105 will experience pain or discomfort induced by the stimulation pulses during the patient event. Put another way, the increased amplitudes of stimulation signals in plot 920 indicate that the risk of increased nerve activation and possible discomfort increases due to a likely change in distance between electrodes and nerve fibers.

Figure 10:
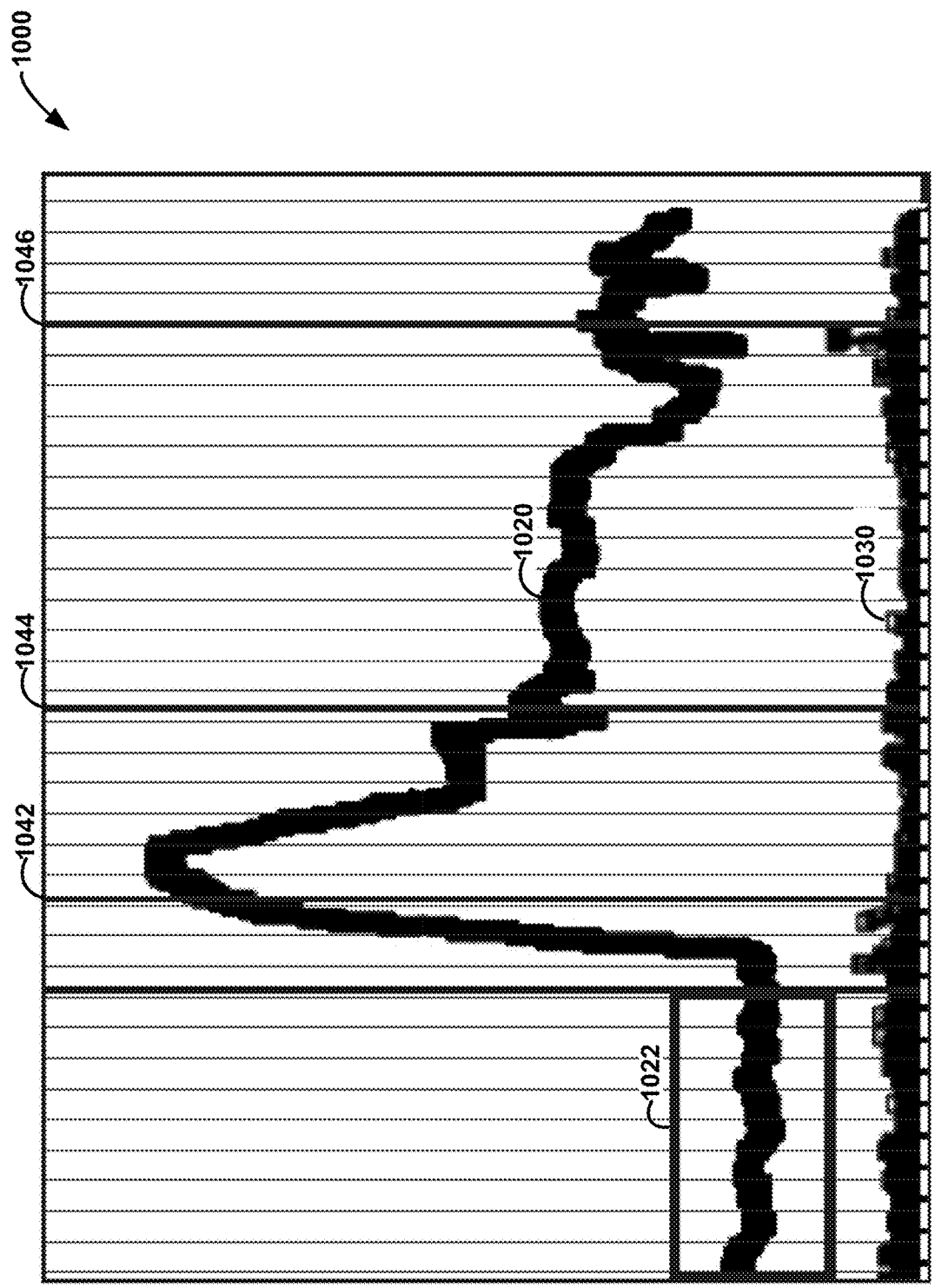
FIG. 10 is a graph illustrating a stimulation signal amplitude plot and an ECAP amplitude plot, in accordance with one or more techniques of this disclosure.

FIG. 10 is a graph 1000 illustrating a stimulation signal amplitude plot 1020 and an ECAP amplitude plot 1030, in accordance with one or more techniques of this disclosure. Additionally, graph 1000 includes a region 1022, a first time 1042, a second time 1044, and a third time 1046. FIG. 10 is described with reference to IMD 200 of FIG. 2. In some examples, a first patient event may occur between first time 1042 and second time 1044, a second patient event may occur between second time 1044 and third time 1046, and a third patient event may occur after third time 1046. In some examples, processing circuitry 210 may detect one or more signals signal which represent stimulation signal amplitude plot 1020 and one or more signals which represent ECAP amplitude plot 1030. In some examples, processing circuitry 210 may identify the first patient event, the second patient event, and the third patient event based on one or both of the stimulation signal amplitude plot 1020 and the ECAP amplitude plot 1030. As seen in FIG. 10, the amplitude of stimulation signals is generally greater than the amplitude of ECAPs. For this reason, it may be beneficial to determine patient events using the amplitude of stimulation signals which are sensed by IMD 200 in response to delivered stimulation pulses in addition, or as an alternative to, ECAP signals.

Region 1022 may represent a period of time in which patient 105 is sitting still and both of the stimulation signal amplitude plot 1020 and the ECAP amplitude plot 1030 are stable. An amplitude of stimulation pulses delivered by IMD 200 is kept stable throughout the duration of graph 1000. Each of the first patient event, the second patient event, and the third patient event may represent an aggressor event (e.g., a cough, a sneeze, or a body stretch) which causes a distance between one or more of electrodes 232, 234 moves closer to spinal cord 120, causing stimulation pulses to induce a stronger, and sometimes uncomfortable, sensation in patient 105. As such, it may be beneficial to adjust stimulation in response to detecting an aggressor event such as the first patient event.

Figure 11:
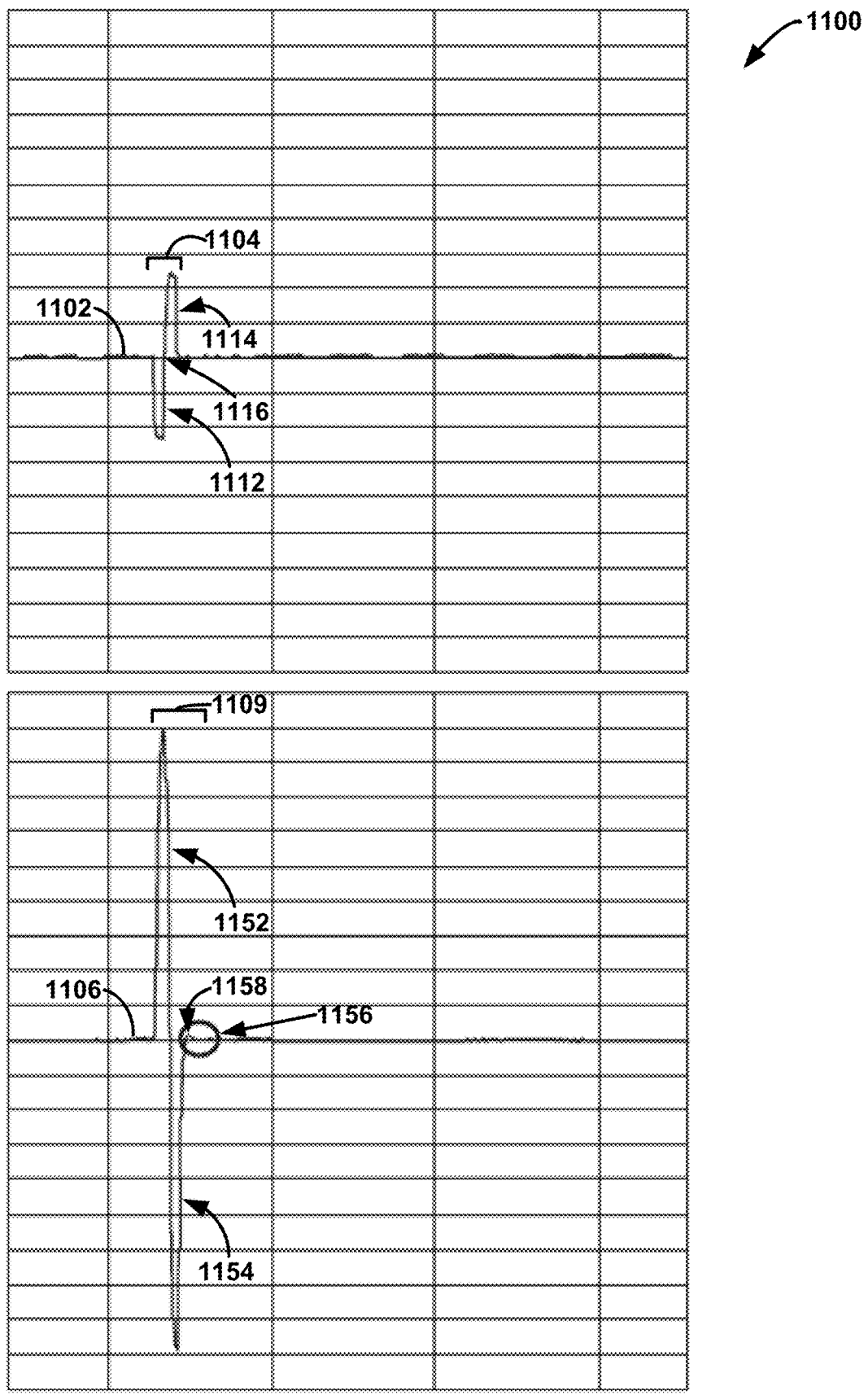
FIG. 11 is a timing diagram illustrating an example of an electrical stimulation pulse and a respective stimulation signal, in accordance with one or more techniques of this disclosure.

FIG. 11 is a timing diagram 1100 illustrating an example of an electrical stimulation pulse 1104 and a respective stimulation signal 1109, in accordance with one or more techniques of this disclosure. For convenience, FIG. 11 is described with reference to IMD 200 of FIG. 2. As illustrated, timing diagram 1100 includes stimulation signal 1102 and a sense signal 1106. In some examples, stimulation signal 1102 includes electrical stimulation pulse 1104 and sense signal includes stimulation signal 1109. Stimulation signal 1109 includes a first phase 1152, a second phase 1154, and a third phase 1156. Third phase 1156 includes a third phase peak 1158. The first phase 1152 and second phase 1154 may also include a respective phase peak.

As seen in FIG. 11, electrical stimulation pulse 1104 may represent a balanced, bi-phasic square pulse that employs an active recharge phase. In other examples not illustrated in FIG. 11, electrical stimulation pulse 1104 may represent a monophasic pulse that employs a passive recharge phase or an imbalanced bi-phasic pulse that employs a passive recharge phase. Electrical stimulation pulse 1104 includes a negative phase 1112 and a positive phase 1114. In examples where electrical stimulation pulse 1104 represents a balanced, bi-phasic square pulse, negative phase 1112 and positive phase 1114 may include approximately the same magnitude and approximately the same duration. In some examples, electrical stimulation pulse 1104 may include an interphase interval 1116 between negative phase 1112 and positive phase 1114 to promote propagation of a nerve impulse in response to negative phase 1112 of the bi-phasic pulse. As discussed herein, pulses have different numbers of phases, such as a monophasic or tri-phasic pulse may be employed in other examples.

Stimulation generation circuitry 202 may generate electrical stimulation pulse 1104 based on one of therapy stimulation programs 214 or test stimulation programs 216 and deliver electrical stimulation pulse 1104 to target tissue of patient 105 via any one or combination of electrodes 232, 234. Since the one or combination of electrodes 232, 234 (e.g., "stimulation electrodes") which deliver electrical stimulation pulse 1104 to the target tissue may be located to proximate to a one or combination of electrodes 232, 234 (e.g., "sensing electrodes") which are configured to sense electrical signals, the sensing electrodes may detect one or more electrical signals emitted by the stimulation electrodes as electrical stimulation pulse 1104. Sensing circuitry 206 may detect these one or more electrical signals as stimulation signal 1109. In this way, sensing circuitry 106 may detect stimulation signal 1109 as a direct result of stimulation generation circuitry 202 delivering electrical stimulation pulse 1104 to the target tissue.

Sensing circuitry 206 may sense the first phase 1152 of stimulation signal 1109 in response to stimulation generation circuitry 202 delivering the negative phase 1112 of electrical stimulation pulse 1104. Additionally, sensing circuitry 206 may sense the second phase 1154 of stimulation signal 1109 in response to stimulation generation circuitry 202 delivering the positive phase 1114 of electrical stimulation pulse 1104. As seen in FIG. 11, the first phase 1152 is a positive phase and the second phase 1154 is a negative phase. In this way, sensing circuitry 206 may sense a positive stimulation signal phase in response to stimulation generation circuitry 202 delivering a negative stimulation pulse phase and sensing circuitry 206 may sense a negative stimulation signal phase in response to stimulation generation circuitry 202 delivering a positive stimulation pulse phase, but this is not required. In some examples not illustrated in FIG. 11, sensing circuitry 206 may sense a positive stimulation signal phase in response to stimulation generation circuitry 202 delivering a positive stimulation pulse phase and sensing circuitry 206 may sense a negative stimulation signal phase in response to stimulation generation circuitry 202 delivering a negative stimulation pulse phase.

In some examples, processing circuitry 210 may determine one or more parameters (e.g., voltage amplitude, current amplitude, pulse duration, pulse shape, or any combination thereof) of upcoming stimulation pulses for generation by stimulation generation circuitry 202 based on one or both of the first phase 1152 and the second phase 1154 of stimulation signal 1109. Additionally, or alternatively, processing circuitry 210 may determine the one or more parameters of upcoming stimulation pulses for generation by stimulation generation circuitry 202 based on one or more characteristics of third phase 1156 (e.g., an amplitude of peak 1158). Third phase 1156 may be referred to as a residual phase in some examples and occurs after second phase 1154. More specifically, third phase 1156 begins after stimulation signal 1109 returns to zero at the conclusion of second phase 1154. As illustrated, peak 1158 occurs shortly after the conclusion of second phase 1154. In some examples, a magnitude of peak 1158 of third phase 1156 may be more affected by a posture of patient 105 as compared with a magnitude of first phase 1152 and a magnitude of second phase 1154. As such, when using the magnitude of peak 1158 to determine therapy, it may be beneficial for processing circuitry 210 to determine a posture of patient 105 based on the acceleration signal generated by acceleration sensor 223. It is noted that the third phase 1156 may or may not be detectable when an ECAP signal is detectable after stimulation signal 1109.

Figure 12:
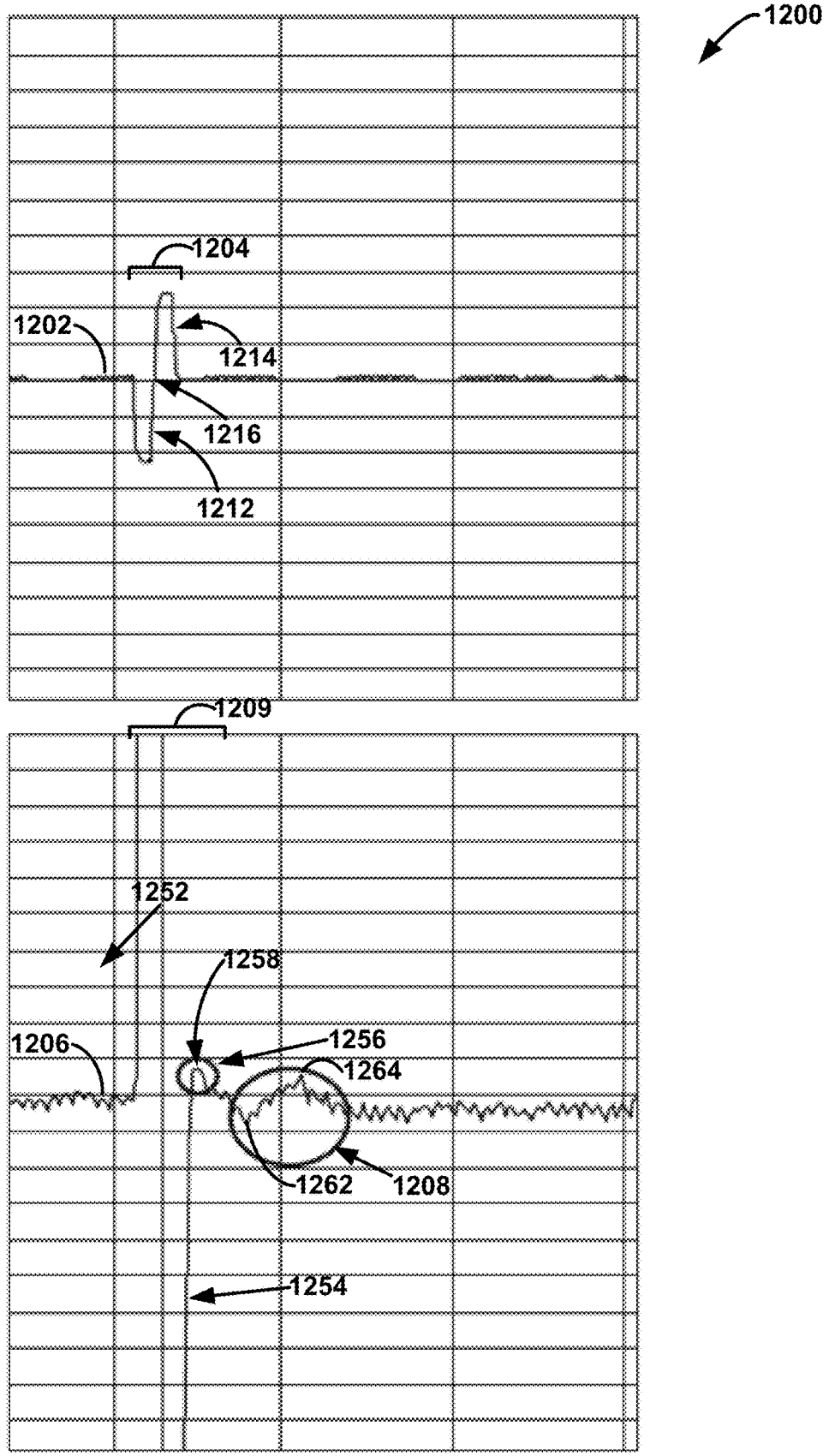
FIG. 12 is a timing diagram illustrating an example of an electrical stimulation pulse, a respective ECAP, and a respective stimulation signal, in accordance with one or more techniques of this disclosure.

FIG. 12 is a timing diagram 1200 illustrating an example of an electrical stimulation pulse 1104, a respective ECAP 1208, and a respective stimulation signal 1209, in accordance with one or more techniques of this disclosure. For convenience, FIG. 12 is described with reference to IMD 200 of FIG. 2. As illustrated, timing diagram 1200 includes stimulation signal 1202 and a sense signal 1206. In some examples, stimulation signal 1202 includes electrical stimulation pulse 1204 and sense signal 1206 includes ECAP 1208 and stimulation signal 1209. Stimulation signal 1209 includes a first phase 1252, a second phase 1254, and a third phase 1256. Third phase 1256 includes a third phase peak 1258. Third phase 1256 may be referred to as a residual phase in some cases and may represent an ionic rebalancing occurring on one or more of electrodes 232, 234 of IMD 200. Although the third phase 1256 may not represent actively delivered charge from IMD 200, third phase 1256 may still be associated with the first and second phase because the residual charge present in the tissue is due to the pulse that was just delivered. Timing diagram 1200 of FIG. 12 may be substantially the same as timing diagram 1100 of FIG. 11 except that sense signal 1206 includes ECAP 1208 in addition to third phase 1256 of stimulation signal 1209. ECAP 1208 includes N1 peak 1262 and P2 peak 1264. As described herein, IMD 200 may adjust one or more parameter values for subsequent stimulation pulses based on characteristics of stimulation signal 1209 and/or ECAP 1208.

Figure 13:
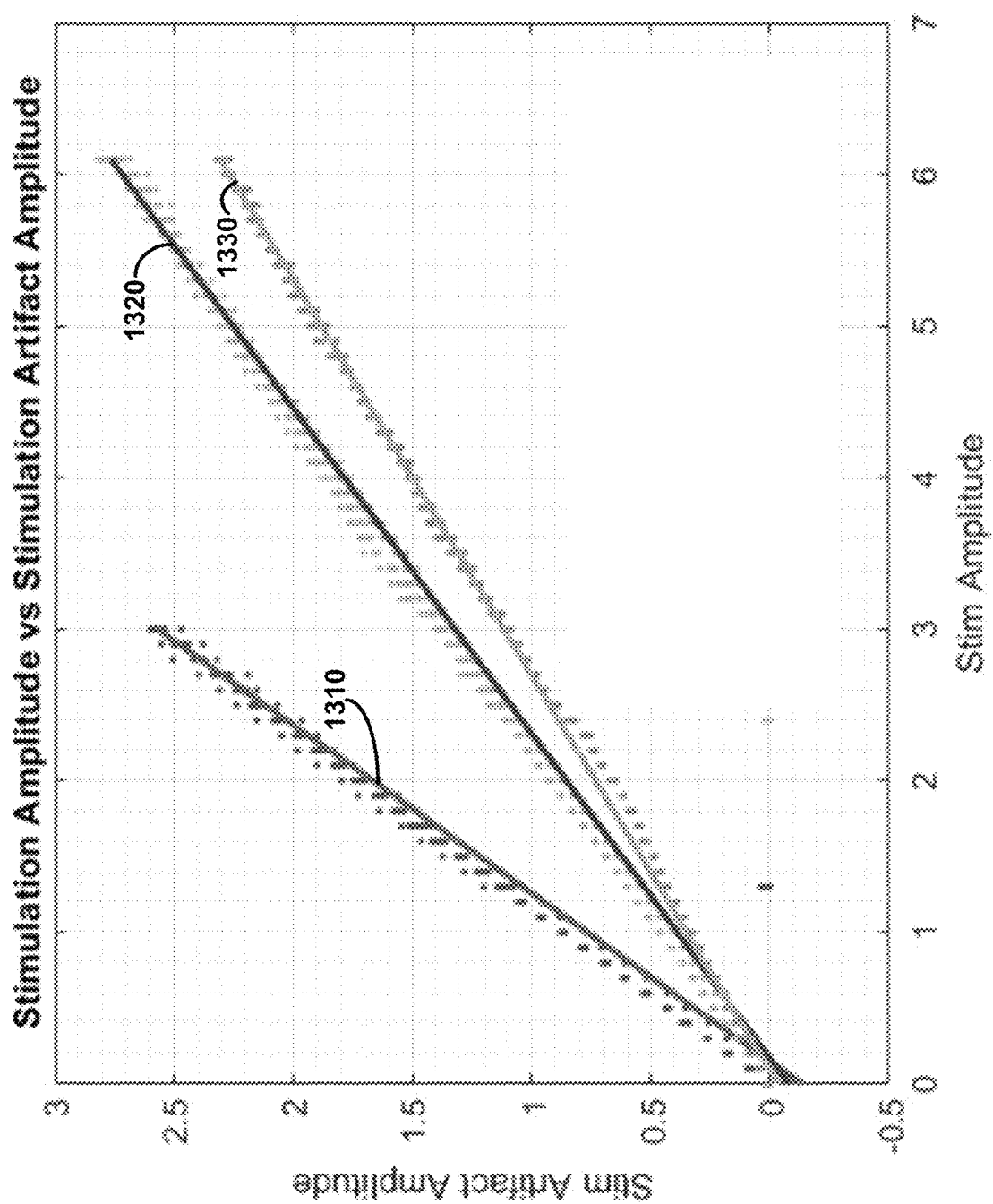
FIG. 13 is a graph illustrating a first transfer function corresponding to a first posture, a second transfer function corresponding to a second posture, and a third transfer function corresponding to a third posture, in accordance with one or more techniques of this disclosure.

FIG. 13 is a graph illustrating a first transfer function 1310 corresponding to a first posture, a second transfer function 1320 corresponding to a second posture, and a third transfer function 1330 corresponding to a third posture, in accordance with one or more techniques of this disclosure. As described herein, a "transfer function" may represent a curve which establishes a relationship between a first parameter and a second parameter. In the case of FIG. 13, a transfer function represents a relationship between an amplitude of a stimulation pulse and an expected amplitude of a portion of a stimulation signal that is detected by sensing circuitry 206 in response to delivering the stimulation pulse. In some examples, each transfer function may be used to determine a gain or multiplier that IMD 200 applies to detected stimulation signal amplitudes in order increase or decrease parameter values an appropriate amount (e.g., smaller changes for larger slopes of a transfer function and larger changes for smaller slopes of a transfer function).

First transfer function 1310 may represent a relationship between stimulation pulse amplitude and an expected stimulation signal amplitude while patient 105 is occupying a supine posture. Second transfer function 1320 may represent a relationship between stimulation pulse amplitude and an expected stimulation signal amplitude while patient 105 is occupying a seated posture. Third transfer function 1330 may represent a relationship between stimulation pulse amplitude and an expected stimulation signal amplitude while patient 105 is occupying a standing posture. A prone posture may provide another transfer function that may be different or similar to transfer function 1330 of the standing posture. As seen in FIG. 13, the relationship between stimulation amplitude and expected stimulation signal amplitude is "steeper" for first transfer function 1310 as compared with second transfer function 1320. In this way, an increase in stimulation amplitude may cause a first increase in expected stimulation signal amplitude according to first transfer function 1310 and a second increase in expected stimulation signal amplitude according to second transfer function 1320, where the first increase is greater than the second increase. Additionally, the relationship between stimulation amplitude and expected stimulation signal amplitude is steeper for second transfer function 1320 as compared with third transfer function 1330.

As discussed in more detail below, processing circuitry 210 of IMD 200 may select, based on a determined posture of patient 105, a transfer function for identifying an expected amplitude for a stimulation signal sensed by IMD 200 in response to a delivery of a stimulation pulse. The selected transfer function may include first transfer function 1310, second transfer function 1320, third transfer function 1330, or another transfer function not illustrated in FIG. 13. A set of transfer functions each corresponding top a respective patient posture may be stored by storage device 212 of IMD 200. Subsequent to selecting a transfer function, processing circuitry may determine the expected amplitude of the stimulation signal based on an amplitude of the respective stimulation pulse. In some examples, processing circuitry 210 may determine whether to change one or more parameters of upcoming stimulation pulses based on whether a measured amplitude of a stimulation signal falls outside a range of amplitude values, where the range includes the expected amplitude of the stimulation signal.

In some examples, IMD 200 may determine first transfer function 1310, second transfer function 1320, and third transfer function 1330 based on characteristics of one or more stimulation signals sensed by IMD 200. For example, IMD 200 may calculate first transfer function 1310 based on respective amplitude values of a set of stimulation signals detected by IMD 200 while patient 105 is occupying the supine posture. Additionally, IMD 200 may calculate second transfer function 1320 based on respective amplitude values of a set of stimulation signals detected by IMD 200 while patient 105 is occupying the seated posture, and IMD 200 may calculate third transfer function 1330 based on respective amplitude values of a set of stimulation signals detected by IMD 200 while patient 105 is occupying the standing posture. Additionally, or alternatively, IMD 200 may determine first transfer function 1310, second transfer function 1320, and third transfer function 1330 based on characteristics of stimulation signals detected in other patients.

Figure 14:
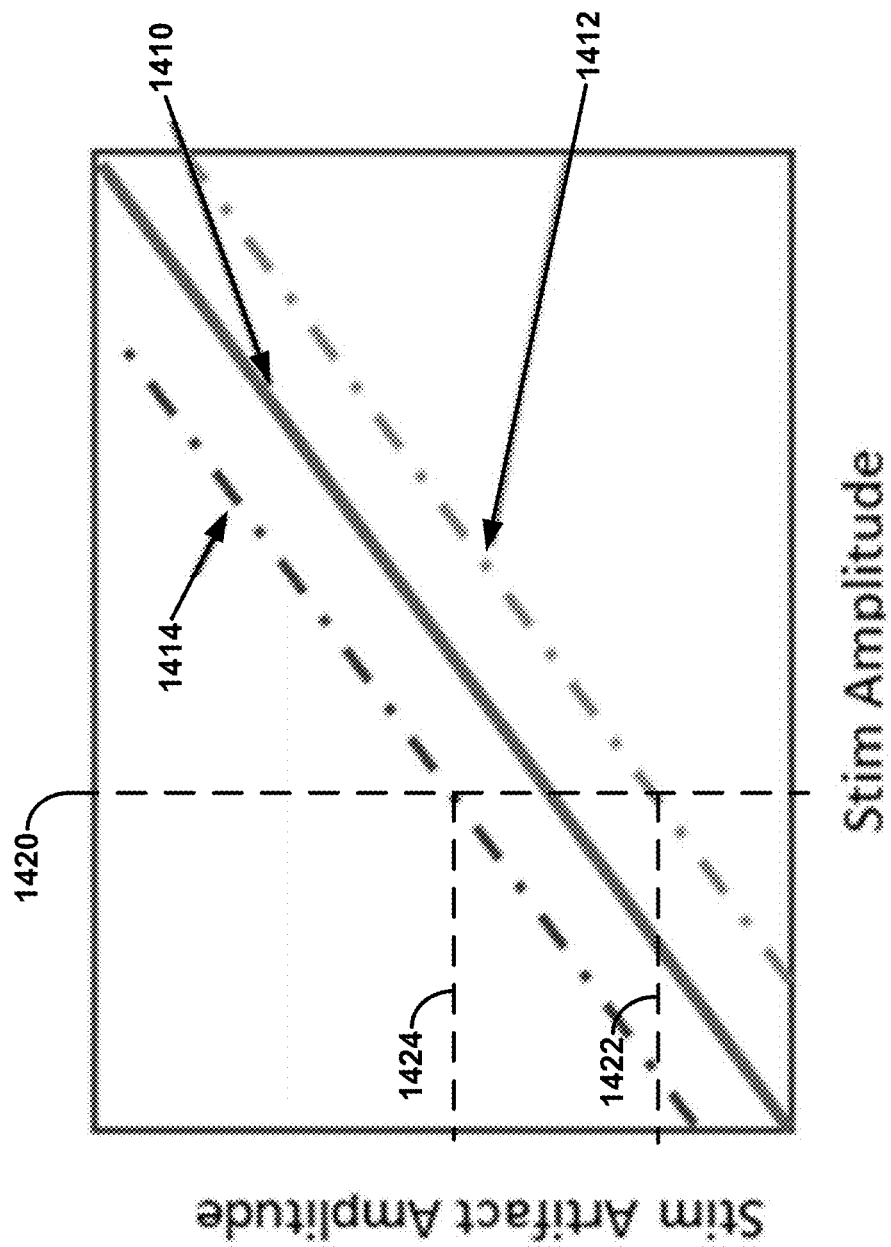
FIG. 14 is a graph illustrating a target range of amplitude values for a stimulation signal in relation to a transfer function corresponding to a respective patient posture, in accordance with one or more techniques of this disclosure.

FIG. 14 is a graph illustrating a target range of amplitude values for a stimulation signal in relation to a transfer function 1410 corresponding to a respective patient posture, in accordance with one or more techniques of this disclosure. In some examples, transfer function 1410 may represent first transfer function 1310, second transfer function 1320, third transfer function 1330, or another transfer function not illustrated in FIG. 13. In some examples, a lower boundary function 1412 and an upper boundary function 1414 may define an expected range of stimulation signal amplitudes based on an amplitude of the respective stimulation pulse delivered by stimulation generation circuitry 202. For example, stimulation pulse amplitude 1420 may correspond to a range of expected stimulation signal amplitude values ranging from lower-bound target stimulation signal amplitude 1422 to upper-bound target stimulation signal amplitude 1424.

Using an acceleration signal generated by acceleration sensor 223 of IMD 200, processing circuitry 210 may determine a posture of patient 105. Additionally, in some cases, processing circuitry 210 may acquire an amplitude of a stimulation pulse and select a transfer function associated with the determined patient posture in order to compute a target estimated stimulation signal amplitude. In some examples, the upper boundary function 1414 and the lower boundary function 1412 may be established based on information representing user input received from external programmer 150. In some examples, the upper and lower boundary functions 1414 and 1412 may be determined as a tolerance from the target value of transfer function 1410. However, upper and lower boundary functions 1414 and 1412 may deviate from transfer function 1410 by unequal amounts in other examples.

A stimulation pulse delivered by IMD 200 while patient 105 is occupying a given posture may have a stimulation pulse amplitude. If the responsive stimulation signal amplitude is above the upper-bound target stimulation signal amplitude, processing circuitry 210 may decrease a stimulation pulse amplitude of future stimulation pulses until a responsive stimulation signal includes an amplitude within the target range of stimulation signal amplitudes. If the responsive stimulation signal amplitude is lower than the lower-bound target stimulation signal amplitude, processing circuitry 210 may increase a stimulation pulse amplitude of future stimulation pulses until a responsive stimulation signal includes an amplitude within the target range of stimulation signal amplitudes. If the amplitude of a stimulation signal is within the target range of amplitudes, processing circuitry 210 may hold the amplitude of stimulation pulses constant. In some examples in which processing circuitry 210 detects a shift in posture of patient 105, processing circuitry 210 may accordingly adjust an amplitude of subsequent stimulation pulses.

As described above, processing circuitry 210 may be configured to set, based on one or more characteristics of a stimulation signal, one or more parameters (e.g., pulse amplitude, pulse duration, and pulse shape) of stimulation pulses following the respective stimulation signal. One way in which processing circuitry 210 may set the one or more parameters of the stimulation pulses includes adjusting an amplitude of a set of stimulation pulses following the respective stimulation signal by a predetermined amplitude value. For example, processing circuitry 210 may determine, based on the acceleration signal generated by the acceleration sensor 223, a posture of the patient and determine an amplitude of a stimulation pulse delivered by IMD 200. Processing circuitry 210 may select a transfer function from storage device 212 based on the determined posture, and determine a target range of amplitudes for a stimulation signal corresponding to the stimulation pulse based on the amplitude of the stimulation pulse and the selected transfer function.

In some examples, IMD 200 may change an amplitude of stimulation pulses delivered by IMD 200 based on determining that an amplitude of a stimulation signal is outside of a target range of stimulation signal amplitudes. For example, if an amplitude of a stimulation signal is above an upper bound of the target range of stimulation signal amplitudes, processing circuitry 210 may decrement an amplitude of stimulation pulses until processing circuitry 210 identifies a stimulation signal having an amplitude within the target range of stimulation signal amplitudes. Additionally, or alternatively, if an amplitude of a stimulation signal is below a lower bound of the target range of stimulation signal amplitudes, processing circuitry 210 may increment an amplitude of stimulation pulses until processing circuitry 210 identifies a stimulation signal having an amplitude within the target range of stimulation signal amplitudes. Responsive to identifying a stimulation signal having an amplitude within the target range of stimulation signal amplitudes following a period in which stimulation signal amplitudes are outside of the target range, processing circuitry 210 may restore an amplitude of stimulation pulses delivered by processing circuitry 210 to a baseline value.

In some examples, processing circuitry 210 may determine whether an amplitude of the stimulation signal sensed by IMD 200 in response to the stimulation pulse is within the target range of amplitudes. If the amplitude of the stimulation signal is greater than an upper-bound of target range, processing circuitry 210 may set an amplitude of one or more stimulation pulses following the stimulation signal to a first fall back amplitude. For example, an amplitude transition of consecutive stimulation signals from within the target range to being greater than an upper-bound of the target range may trigger processing circuitry 210 to transition an amplitude of stimulation pulses from a target stimulation pulse amplitude to the first fall back amplitude. In some examples, the first fall back amplitude is lower than the target stimulation pulse amplitude. For example, processing circuitry 210 may calculate the first fall back amplitude using the following equation 1.

$$\text{first fall back amplitude} = \text{target stimulation pulse amplitude} - [x] \qquad (1)$$

The value "[x]" may be saved by storage device 212 of IMD 200. In some examples, processing circuitry 210 may save the value "[x]" to storage device 212 based on information received by IMD 200 via communication circuitry 208. In some examples, processing circuitry 210 may adjust the target stimulation pulse amplitude like based on information indicative of a user input to an external device (e.g., external programmer 150), and processing circuitry 210 may automatically calculate the first fall back amplitude based on equation 1. In some examples, processing circuitry 210 may maintain an amplitude of stimulation pulses delivered by processing circuitry 210 at the first fall back amplitude until processing circuitry 210 identifies a stimulation signal having an amplitude within the target range. In response to detecting the stimulation signal having an amplitude within the target range, processing circuitry 210 may restore the amplitude of stimulation pulses delivered by IMD 200 to the target stimulation pulse amplitude.

Additionally, in some examples, processing circuitry 210 may determine whether an amplitude of a stimulation signal is less than a lower-bound of a target range of stimulation signal amplitude values, processing circuitry 210 may set an amplitude of one or more stimulation pulses following the stimulation signal to a second fall back amplitude. For example, an amplitude transition of consecutive stimulation signals from being within the target range to being greater than an upper-bound of the target range may trigger processing circuitry 210 to transition an amplitude of stimulation pulses from a target stimulation pulse amplitude to the second fall back amplitude. In some examples, the second fall back amplitude is greater than the target stimulation pulse amplitude. For example, processing circuitry 210 may calculate the second fall back amplitude using the following equation 2.

$$\text{second fall back amplitude} = \text{target stimulation pulse amplitude} - [y] \qquad (2)$$

The value "[y]" may be saved by storage device 212 of IMD 200. In some examples, processing circuitry 210 may save the value "[y]" to storage device 212 based on information received by IMD 200 via communication circuitry 208. The value "[y]" may be a negative value. In some examples, processing circuitry 210 may adjust the target stimulation pulse amplitude like based on information indicative of a user input to an external device (e.g., external programmer 150), and processing circuitry 210 may automatically calculate the second fall back amplitude based on equation 2. In some examples, processing circuitry 210 may maintain an amplitude of stimulation pulses delivered by processing circuitry 210 at the second fall back amplitude until processing circuitry 210 identifies a stimulation signal having an amplitude within the target range. In response to detecting the stimulation signal having an amplitude within the target range, processing circuitry 210 may restore the amplitude of stimulation pulses delivered by IMD 200 to the target stimulation pulse amplitude.

Figure 15:
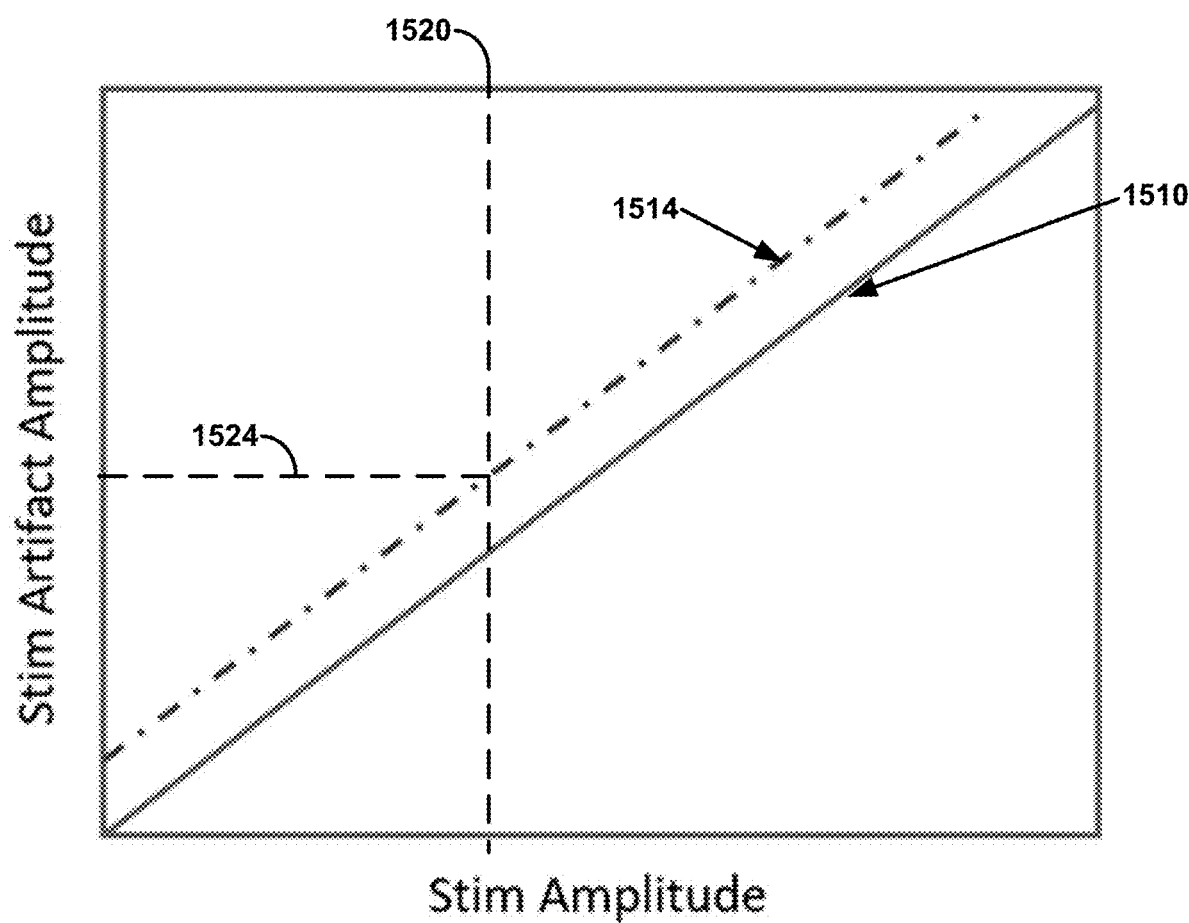
FIG. 15 is a graph illustrating target maximum values for a stimulation signal in relation to a transfer function corresponding to a respective patient posture, in accordance with one or more techniques of this disclosure.

FIG. 15 is a graph illustrating target maximum values for a stimulation signal in relation to a transfer function 1510 corresponding to a respective patient posture, in accordance with one or more techniques of this disclosure. In some examples, transfer function 1510 may represent first transfer function 1310, second transfer function 1320, third transfer function 1330, or another transfer function not illustrated in FIG. 13. In some examples, an upper boundary function 1514 may define a target maximum stimulation signal amplitude value based on an amplitude of the respective stimulation pulse delivered by stimulation generation circuitry 202. For example, stimulation pulse amplitude 1520 may correspond to a target maximum stimulation signal amplitude value 1524. In the example of FIG. 15, the target range may correspond to the values less than upper boundary function 1514.

In one example, IMD 200 delivers a stimulation pulse at stimulation pulse amplitude 1520. If a resulting stimulation signal amplitude is greater than target maximum stimulation signal amplitude value 1524, IMD 200 may decrease the stimulation amplitude of one or more subsequent stimulation pulses until a stimulation pulse causes IMD 200 to sense a stimulation signal defining a stimulation signal amplitude value that is less than a respective target maximum stimulation signal amplitude value. If the stimulation signal amplitude value is less than the respective target maximum stimulation signal amplitude value, IMD 200 may hold the stimulation amplitude until a posture of patient 105 is shifted and IMD 200 may adjust a stimulation amplitude based on identifying a new transfer function associated with the shifted posture.

In some examples, processing circuitry 210 may determine whether an amplitude of a stimulation signal sensed by IMD 200 in response to a stimulation pulse is greater than a target maximum stimulation signal amplitude value of upper boundary function 1514. If the amplitude of the stimulation signal is greater than the target maximum stimulation signal amplitude value, processing circuitry 210 may set an amplitude of one or more stimulation pulses following the stimulation signal to a fall back amplitude. For example, an amplitude transition of consecutive stimulation signals from being less than the target maximum stimulation signal amplitude value to being greater than the target maximum stimulation signal amplitude value may trigger processing circuitry 210 to decrease an amplitude of stimulation pulses from a target stimulation pulse amplitude to the fall back amplitude. In some examples, the fall back amplitude is lower than the target stimulation pulse amplitude. For example, processing circuitry 210 may calculate the fall back amplitude using the following equation 3.

$$\text{fall back amplitude} = \text{target stimulation pulse amplitude} - [z] \qquad (3)$$

The value "[z]" may be saved by storage device 212 of IMD 200. In some examples, processing circuitry 210 may save the value "[z]" to storage device 212 based on information received by IMD 200 via communication circuitry 208. In some examples, processing circuitry 210 may adjust the target stimulation pulse amplitude based on information indicative of a user input to an external device (e.g., external programmer 150), and processing circuitry 210 may automatically calculate the fall back amplitude based on equation 3. In some examples, processing circuitry 210 may maintain an amplitude of stimulation pulses delivered by processing circuitry 210 at the fall back amplitude until processing circuitry 210 identifies a stimulation signal having an amplitude between the respective stimulation signal value of transfer function 1520 and the target maximum stimulation signal amplitude value of upper boundary 1514. In response to detecting the stimulation signal having an amplitude between the respective stimulation signal value of transfer function 1520 and the target maximum stimulation signal amplitude value of upper boundary 1514, processing circuitry 210 may restore the amplitude of stimulation pulses delivered by IMD 200 to the target stimulation pulse amplitude.

Figure 16:
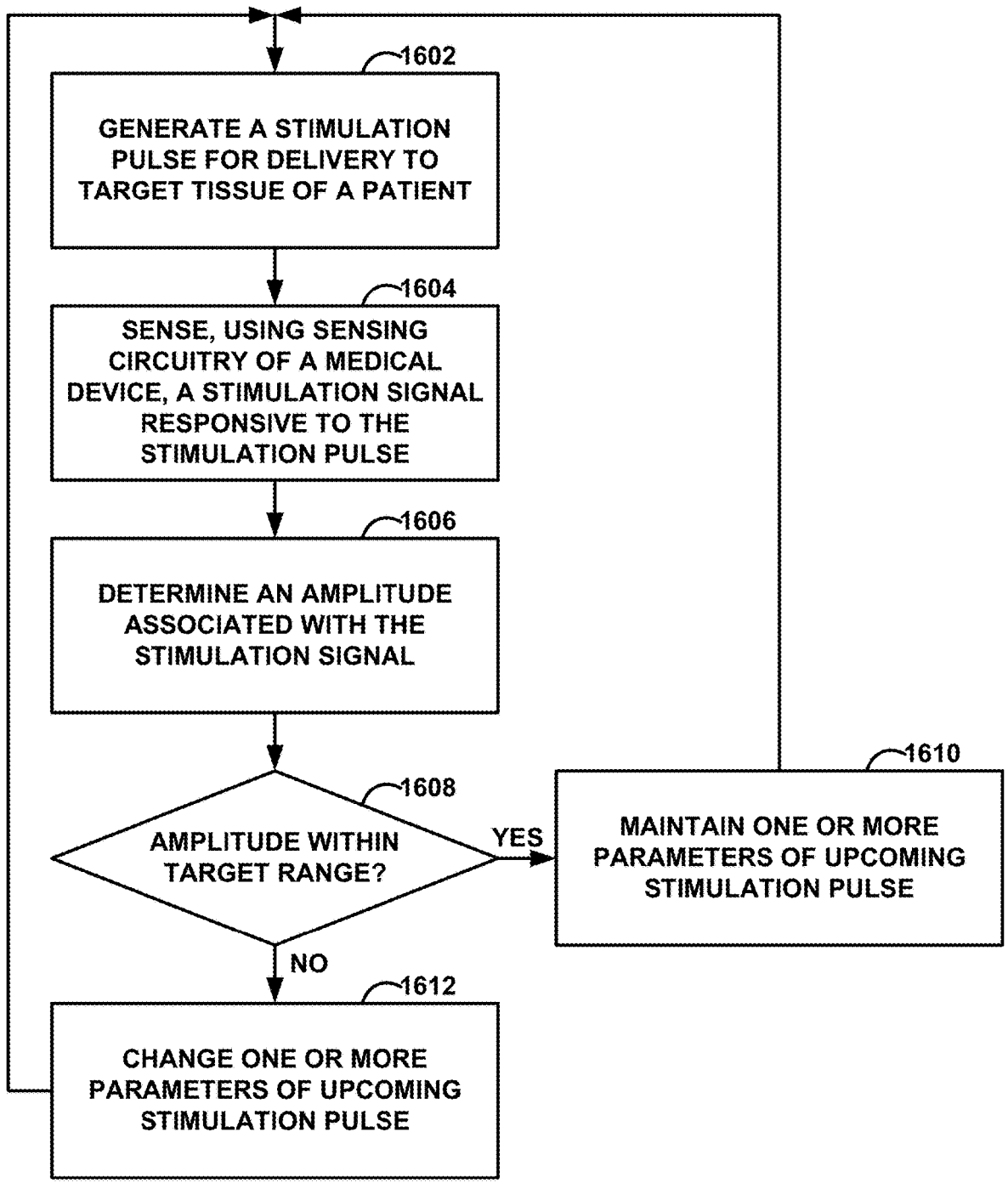
FIG. 16 is a flow diagram illustrating an example operation for controlling simulation based on one or more stimulation signals, in accordance with one or more techniques of this disclosure.

FIG. 16 is a flow diagram illustrating an example operation for controlling simulation based on one or more stimulation signals, in accordance with one or more techniques of this disclosure. FIG. 16 is described with respect to IMD 200 of FIG. 2. However, the techniques of FIG. 16 may be performed by different components of IMD 200 or by additional or alternative medical devices. The technique of FIG. 15 may be similar to the example of FIG. 14 in some examples.

Stimulation generation circuitry 202 is configured to generate a stimulation pulse for delivery to target tissue of patient 105 (1602). In some examples, stimulation generation circuitry 202 is configured to generate the stimulation pulse according to therapy stimulation programs 214 and/or test stimulation programs 216 as a one of a set of stimulation pulses. In some examples, therapy stimulation programs 214 and/or test stimulation programs 216 may include one or more parameter values which define stimulation pulses delivered by IMD 200. Sensing circuitry 206 may sense a stimulation signal responsive to the stimulation pulse delivered to the target tissue of patient 105 (1604). In some examples, the stimulation signal may include one or more phases (e.g., a first phase, a second phase, and a third phase). In some examples, a first phase of the stimulation signal may be responsive to a first phase of the stimulation pulse and a second phase of the stimulation signal may be responsive to a second phase of the stimulation pulse. In some examples, a third phase of the stimulation signal may directly follow the second phase of the stimulation signal and the third phase of the stimulation signal may include information indicative of an efficacy of electrical stimulation therapy which includes the stimulation pulse.

Processing circuitry 210 may determine an amplitude associated with the stimulation signal (1606). The amplitude may be a characteristic of the stimulation signal. In some examples, the amplitude may represent an amplitude of the third phase of the stimulation signal. In some examples, the amplitude may represent an amplitude of one or both of the first phase of the stimulation signal and the second phase of the stimulation signal. Processing circuitry 210 may determine whether the amplitude associated with the stimulation signal is within a target range of stimulation signal amplitude values (1608). In some examples, processing circuitry 210 may select the target range of stimulation signal amplitude values from target values 218 stored in storage device 212. For example, processing circuitry 210 may select the target range of stimulation signal amplitude values based on a determined posture of patient 105 and an amplitude of the stimulation pulse which causes IMD 200 to sense the stimulation signal. In response to determining that the amplitude associated with the stimulation signal is within the target range of stimulation signal amplitude values ("YES" branch of block 1608), processing circuitry 210 may maintain one or more parameters of an upcoming one or more stimulation pulses (1610) and the example operation may return to block 1602. In response to determining that the amplitude associated with the stimulation signal is not within the target range of stimulation signal amplitude values ("NO" branch of block 1608), processing circuitry 210 may change one or more parameters of an upcoming one or more stimulation pulses (1612) and the example operation may return to block 1602.

Figure 17:
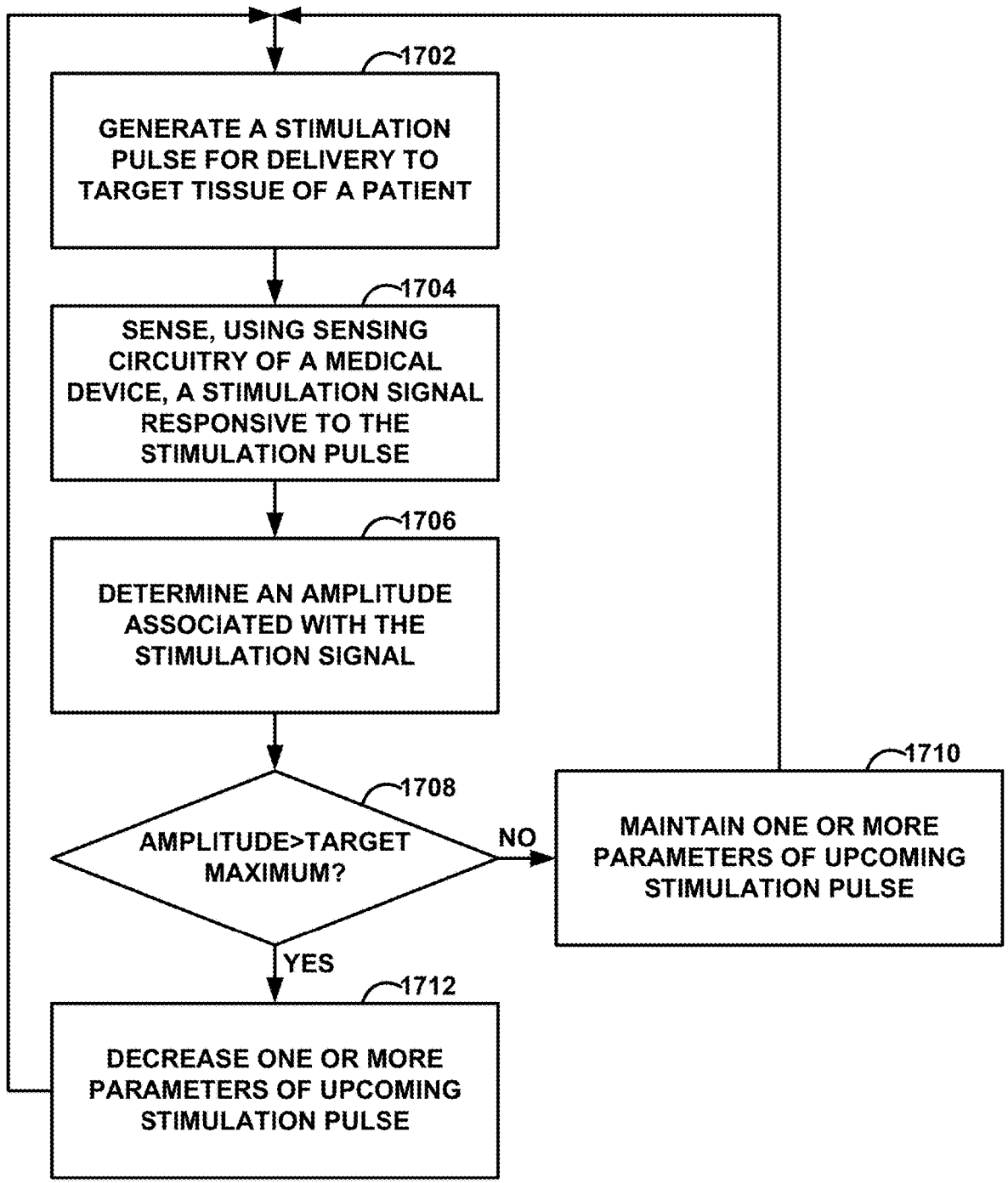
FIG. 17 is a flow diagram illustrating another example operation for controlling simulation based on one or more stimulation signals, in accordance with one or more techniques of this disclosure.

FIG. 17 is a flow diagram illustrating another example operation for controlling simulation based on one or more stimulation signals, in accordance with one or more techniques of this disclosure. FIG. 17 is described with respect to IMD 200 of FIG. 2. However, the techniques of FIG. 17 may be performed by different components of IMD 200 or by additional or alternative medical devices. The technique of FIG. 17 may be similar to the example of FIG. 15.

Stimulation generation circuitry 202 is configured to generate a stimulation pulse for delivery to target tissue of patient 105 (1702). In some examples, stimulation generation circuitry 202 is configured to generate the stimulation pulse according to therapy stimulation programs 214 and/or test stimulation programs 216 as a one of a set of stimulation pulses. In some examples, therapy stimulation programs 214 and/or test stimulation programs 216 may include one or more parameter values which define stimulation pulses delivered by IMD 200. Sensing circuitry 206 may sense a stimulation signal responsive to the stimulation pulse delivered to the target tissue of patient 105 (1704). In some examples, the stimulation signal may include one or more phases (e.g., a first phase, a second phase, and a third phase). In some examples, a first phase of the stimulation signal may be responsive to a first phase of the stimulation pulse and a second phase of the stimulation signal may be responsive to a second phase of the stimulation pulse. In some examples, a third phase of the stimulation signal may directly follow the second phase of the stimulation signal and the third phase of the stimulation signal may include information indicative of an efficacy of electrical stimulation therapy which includes the stimulation pulse.

Processing circuitry 210 may determine an amplitude associated with the stimulation signal (1706). The amplitude may be a characteristic of the stimulation signal. In some examples, the amplitude may represent an amplitude of the third phase of the stimulation signal. In some examples, the amplitude may represent an amplitude of one or both of the first phase of the stimulation signal and the second phase of the stimulation signal. Processing circuitry 210 may determine whether the amplitude associated with the stimulation signal is greater than a target maximum stimulation signal amplitude value (1708). In some examples, processing circuitry 210 may select the target maximum stimulation signal amplitude value from target values 218 stored in storage device 212. For example, processing circuitry 210 may select the target maximum stimulation signal amplitude value based on a determined posture of patient 105 and an amplitude of the stimulation pulse which causes IMD 200 to sense the stimulation signal. In response to determining that the amplitude associated with the stimulation signal is not greater than the target maximum stimulation signal amplitude value ("NO" branch of block 1708), processing circuitry 210 may maintain one or more parameters of an upcoming one or more stimulation pulses (1710) and the example operation may return to block 1702. In response to determining that the amplitude associated with the stimulation signal is greater than the target maximum stimulation signal amplitude value ("YES" branch of block 1708), processing circuitry 210 may decrease one or more parameters of an upcoming one or more stimulation pulses (1712) and the example operation may return to block 1702.

Figure 18:
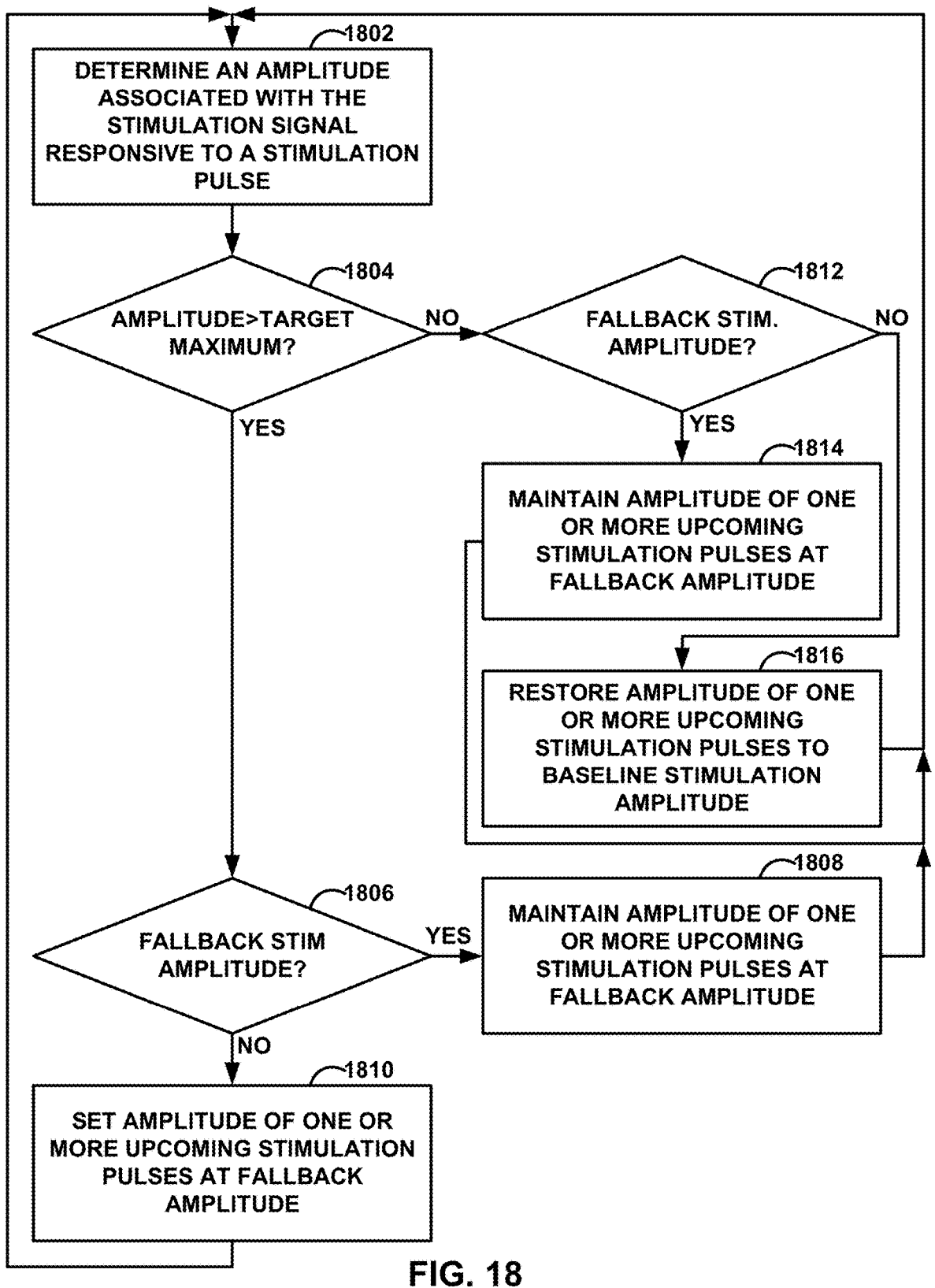
FIG. 18 is a flow diagram illustrating another example operation for controlling simulation based on one or more stimulation signals, in accordance with one or more techniques of this disclosure.

FIG. 18 is a flow diagram illustrating another example operation for controlling simulation based on one or more stimulation signals, in accordance with one or more techniques of this disclosure. FIG. 18 is described with respect to IMD 200 of FIG. 2. However, the techniques of FIG. 18 may be performed by different components of IMD 200 or by additional or alternative medical devices.

Processing circuitry 210 may determine an amplitude associated with a stimulation signal responsive to a stimulation pulse (1802) delivered by IMD 200. The amplitude may be a characteristic of the stimulation signal. In some examples, the amplitude may represent an amplitude of the third phase of the stimulation signal. In some examples, the amplitude may represent an amplitude of one or both of the first phase of the stimulation signal and the second phase of the stimulation signal. Processing circuitry 210 may determine whether the amplitude associated with the stimulation signal is greater than a target maximum stimulation signal amplitude value (1804). In some examples, processing circuitry 210 may select the target maximum stimulation signal amplitude value from target values 218 stored in storage device 212. For example, processing circuitry 210 may select the target maximum stimulation signal amplitude value based on a determined posture of patient 105 and an amplitude of the stimulation pulse which causes IMD 200 to sense the stimulation signal.

In response to determining that the amplitude associated with the stimulation signal is greater than the target maximum stimulation signal amplitude value ("YES" branch of block 1804), processing circuitry 210 may determine whether a current stimulation pulse amplitude represents a fallback stimulation pulse amplitude (1806). In some examples, the fallback stimulation amplitude may be calculated according to equation 3. If the current stimulation pulse amplitude represents the fallback stimulation pulse amplitude ("YES" branch of block 1806), processing circuitry 210 maintains an amplitude of one or more upcoming stimulation pulses at the fallback stimulation amplitude (1808) and the example operation returns to block 1802. If the current stimulation pulse amplitude does not represent the fallback stimulation pulse amplitude ("NO" branch of block 1806), processing circuitry 210 may set the amplitude of one or more upcoming stimulation pulses at the fallback stimulation amplitude (1810) and the example operation returns to block 1802.

In response to determining that the amplitude associated with the stimulation signal is not greater than the target maximum stimulation signal amplitude value ("NO" branch of block 1804), processing circuitry 210 may determine whether a current stimulation pulse amplitude represents a fallback stimulation pulse amplitude (1812). In some examples, the fallback stimulation amplitude may be calculated according to equation 3. If the current stimulation pulse amplitude represents the fallback stimulation pulse amplitude ("YES" branch of block 1812), processing circuitry 210 maintains an amplitude of one or more upcoming stimulation pulses at the fallback stimulation amplitude (1814) and the example operation returns to block 1802. If the current stimulation pulse amplitude does not represent the fallback stimulation pulse amplitude ("NO" branch of block 1812), processing circuitry 210 may restore the amplitude of one or more upcoming stimulation pulses to a baseline stimulation amplitude (1816) and the example operation returns to block 1802. In some examples, the baseline stimulation amplitude represents the target stimulation pulse amplitude of equation 3.

Figure 19:
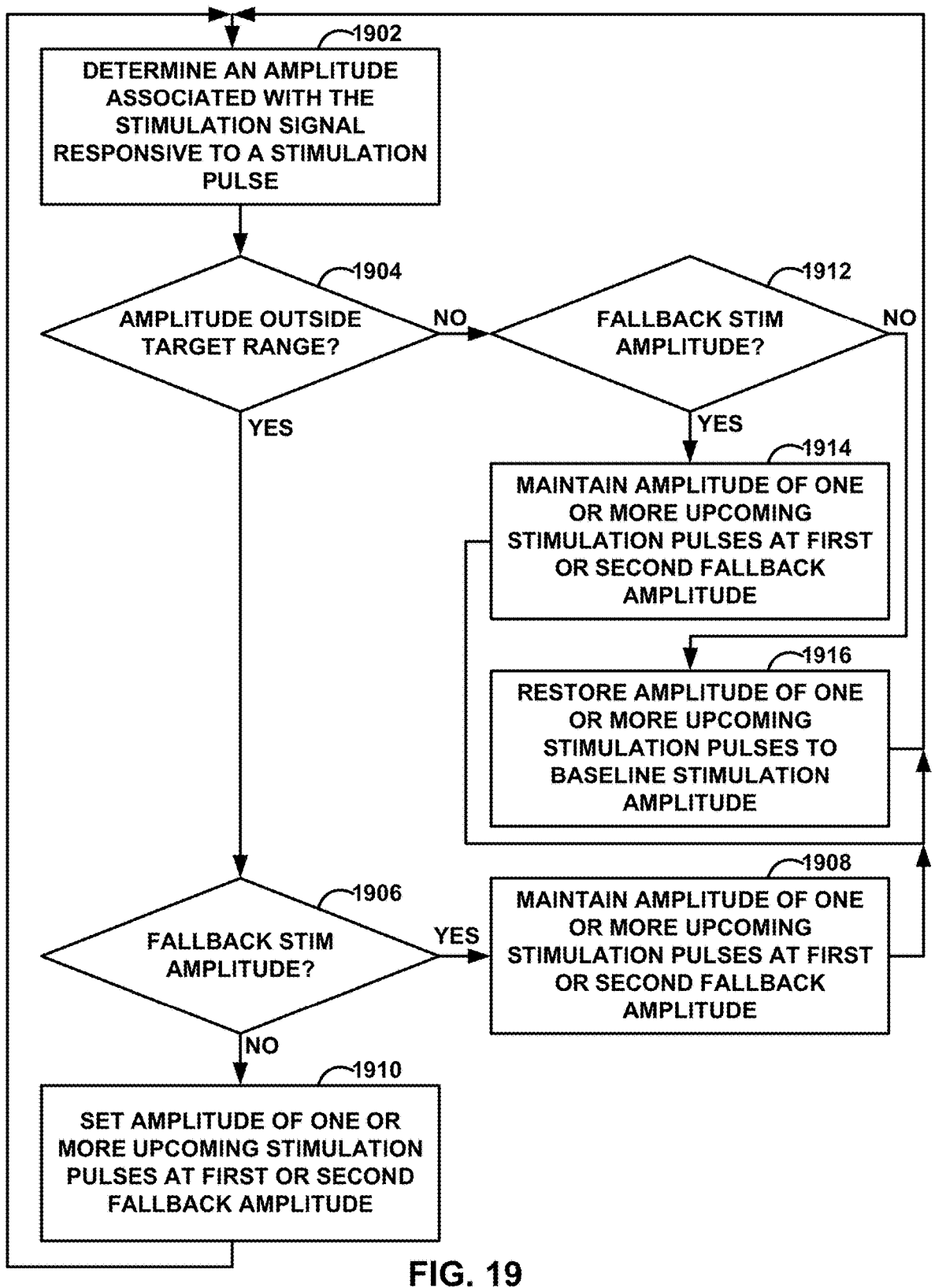
FIG. 19 is a flow diagram illustrating another example operation for controlling simulation based on one or more stimulation signals, in accordance with one or more techniques of this disclosure.

FIG. 19 is a flow diagram illustrating another example operation for controlling simulation based on one or more stimulation signals, in accordance with one or more techniques of this disclosure. FIG. 19 is described with respect to IMD 200 of FIG. 2. However, the techniques of FIG. 19 may be performed by different components of IMD 200 or by additional or alternative medical devices.

Processing circuitry 210 may determine an amplitude associated with a stimulation signal responsive to a stimulation pulse (1902) delivered by IMD 200. The amplitude may be a characteristic of the stimulation signal. In some examples, the amplitude may represent an amplitude of the third phase of the stimulation signal. In some examples, the amplitude may represent an amplitude of one or both of the first phase of the stimulation signal and the second phase of the stimulation signal. Processing circuitry 210 may determine whether the amplitude associated with the stimulation signal is outside of a target range of stimulation signal amplitude values which extends from a lower bound amplitude value to an upper bound amplitude value (1904). In some examples, processing circuitry 210 may select the target range from target values 218 stored in storage device 212. For example, processing circuitry 210 may select the target range based on a determined posture of patient 105 and an amplitude of the stimulation pulse which causes IMD 200 to sense the stimulation signal.

In response to determining that the amplitude associated with the stimulation signal is outside of the target range ("YES" branch of block 1904), processing circuitry 210 may determine whether a current stimulation pulse amplitude represents a first fallback stimulation pulse amplitude or a second fallback stimulation pulse amplitude (1906). For example, if processing circuitry 210 determines that the amplitude associated with the stimulation signal is greater than the upper bound of the target range, processing circuitry 210 may determine whether a current stimulation pulse amplitude represents the first fallback amplitude (e.g., calculated using equation 1) and if processing circuitry 210 determines that the amplitude associated with the stimulation signal is less than the lower bound of the target range, processing circuitry 210 may determine whether a current stimulation pulse amplitude represents the second fallback amplitude (e.g., calculated using equation 2).

If the current stimulation pulse amplitude represents the first fallback stimulation pulse amplitude or the second fallback stimulation pulse amplitude ("YES" branch of block 1906), processing circuitry 210 maintains an amplitude of one or more upcoming stimulation pulses at the respective first or second fallback stimulation amplitude (1908) and the example operation returns to block 1902. If the current stimulation pulse amplitude does not represent the respective first or second fallback stimulation pulse amplitude ("NO" branch of block 1906), processing circuitry 210 may set the amplitude of one or more upcoming stimulation pulses at the respective one of the first fallback stimulation amplitude or the second fallback stimulation amplitude (1910) and the example operation returns to block 1902. For example, if processing circuitry 210 determines that the amplitude associated with the stimulation signal is greater than the upper bound of the target range, processing circuitry 210 may set the amplitude of one or more upcoming stimulation pulses at the first fallback stimulation pulse amplitude and if processing circuitry 210 determines that the amplitude associated with the stimulation signal is less than the lower bound of the target range, processing circuitry 210 may set the amplitude of one or more upcoming stimulation pulses at the second fallback stimulation pulse amplitude.

In response to determining that the amplitude associated with the stimulation signal is not outside of the target range ("NO" branch of block 1904), processing circuitry 210 may determine whether a current stimulation pulse amplitude represents the first fallback stimulation pulse amplitude or the second fallback stimulation pulse amplitude (1912). If the current stimulation pulse amplitude represents the first fallback stimulation pulse amplitude or the second fallback stimulation pulse amplitude ("YES" branch of block 1912), processing circuitry 210 maintains an amplitude of one or more upcoming stimulation pulses at the respective first or second fallback stimulation amplitude (1914) and the example operation returns to block 1902. If the current stimulation pulse amplitude does not represent the first fallback stimulation pulse amplitude or the second fallback stimulation pulse amplitude ("NO" branch of block 1912), processing circuitry 210 may restore the amplitude of one or more upcoming stimulation pulses to a baseline stimulation amplitude (1916) and the example operation returns to block 1902. In some examples, the baseline stimulation amplitude represents the target stimulation pulse amplitude of equation 1 and equation 2.

The following examples are example systems, devices, and methods described herein.

Example 1: A medical device comprising: stimulation generation circuitry configured to deliver a first stimulation pulse to a patient; sensing circuitry configured to sense the first stimulation pulse; and processing circuitry configured to: determine that a value of a characteristic of the sensed first stimulation pulse exceeds a target stimulation pulse value; and responsive to determining that the value of the characteristic of the sensed first stimulation pulse exceeds the target stimulation pulse value, change a first value of a parameter to a second value of the parameter that at least partially defines a second stimulation pulse deliverable by the stimulation generation circuitry after the first stimulation pulse was sensed.

Example 2: The medical device of example 1, wherein to determine that the value of the characteristic of the sensed first stimulation pulse exceeds the target stimulation pulse value, the processing circuitry is configured to: determine that the value of the characteristic of the sensed first stimulation pulse is greater than a target maximum stimulation pulse characteristic value, and wherein to change the first value of the parameter to the second value of the parameter, the processing circuitry is configured to: decrease the first value of the parameter to the second value of the parameter, the second value of the parameter at least partially defining the second stimulation pulse.

Example 3: The medical device of example 2, wherein to decrease the first value of the parameter to the second value of the parameter that at least partially defines the second stimulation pulse, the processing circuitry is configured to: set the parameter which at least partially defines the second stimulation pulse to a fallback parameter value that at least partially defines the second stimulation pulse, wherein the processing circuitry is further configured to: sense a third stimulation pulse following the second stimulation pulse; and responsive to determining that a value of a characteristic of the sensed third stimulation pulse does not exceed the target stimulation pulse value, restore the parameter that at least partially defines a fourth stimulation pulse deliverable by the stimulation generation circuitry to the first value of the parameter.

Example 4: The medical device of any of examples 2-3, wherein the processing circuitry is further configured to: determine that the value of the characteristic of the sensed first stimulation pulse is less than a target minimum stimulation pulse characteristic value, wherein a target range of stimulation pulse characteristic values extend from the target minimum stimulation pulse characteristic value to the target maximum stimulation pulse characteristic value; and responsive to determining that the value of the characteristic of the sensed first stimulation pulse is less than the target minimum stimulation pulse characteristic value, increase the first value of the parameter to the second value of the parameter that at least partially defines the second stimulation pulse.

Example 5: The medical device of any of examples 1-4, wherein the stimulation generation circuitry is configured to deliver a plurality of stimulation pulses including the first stimulation pulse and the second stimulation pulse, and wherein the sensing circuitry is further configured to: detect a plurality of evoked compound action potentials (ECAPs), wherein each ECAP of the plurality of ECAPs is elicited by a respective pulse of the plurality of pulses, and wherein the number of ECAPs of the plurality of ECAPs is lower than a number of stimulation pulses of the plurality of stimulation pulses.

Example 6: The medical device of example 5, wherein the processing circuitry is further configured to determine whether the plurality of stimulation pulses elicit greater than a threshold ratio of detectable ECAPs per stimulation pulse.

Example 7: The medical device of example 6, wherein to determine whether the plurality of stimulation pulses elicit greater than the threshold ratio of detectable ECAPs per stimulation pulse, the processing circuitry is configured to: identify a set of ECAPs elicited by a sequence of consecutive stimulation pulses of the plurality of stimulation pulses; calculate a ratio of a number of the set of ECAPs to a number of the sequence of consecutive stimulation pulses; and determine whether the ratio is greater than the threshold ratio.

Example 8: The medical device of any of examples 6-7, wherein the processing circuitry is further configured to: responsive to determining that the plurality of stimulation pulses elicit greater than the threshold ratio of detectible ECAPs: change, based on the value of the characteristic of the sensed first stimulation pulse and a value of a characteristic of an ECAP corresponding to the first stimulation pulse, the value of the parameter that at least partially defines the second stimulation pulse.

Example 9: The medical device of any of examples 6-8, wherein the processing circuitry is further configured to: responsive to determining that the plurality of stimulation pulses does not elicit greater than the threshold ratio of detectible ECAPs: change, based on the value of the characteristic of the first stimulation pulse and not based on a value of a characteristic of an ECAP corresponding to the first stimulation pulse, the value of the parameter that at least partially defines the second stimulation pulse.

Example 10: The medical device of examples 1-9, further comprising: an accelerometer configured to generate an accelerometer signal, wherein the processing circuitry is further configured to: identify, based on the accelerometer signal, a posture of a set of postures which the patient is occupying; identify an amplitude of the first stimulation pulse; and select, based on the identified posture and the amplitude of the first stimulation pulse, the target stimulation pulse value from a set of target stimulation pulse values, wherein each target stimulation pulse value of the set of target stimulation pulse values corresponds to a respective posture of the set of postures and a respective amplitude of the first stimulation pulse.

Example 11: The medical device of examples 1-10, wherein the medical device comprises an implantable medical device, and wherein the implantable medical device comprises the stimulation generation circuitry, the sensing circuitry, and the processing circuitry.

Example 12: The medical device of any of examples 1-11, wherein the first value of the parameter at least partially defines the first stimulation pulse.

Example 13: The medical device of any of examples 1-12, wherein the first stimulation pulse represents a control pulse of a set of control pulses, wherein the second stimulation pulse represents an informed pulse of a set of informed pulses, wherein the first value of the parameter at least partially defines a pervious informed pulse of the set of informed pulses.

Example 14: The medical device of any of examples 1-13, wherein the stimulation generation circuitry is configured to deliver at least one stimulation pulse between a time in which the stimulation generation circuitry delivers the first stimulation pulse and a time in which the stimulation generation circuitry delivers the second stimulation pulse.

Example 15: The medical device of any of examples 1-14, wherein the first stimulation pulse is one of a first set of one or more stimulation pulses, wherein the second stimulation pulse is one of a second set of one or more stimulation pulses, wherein the characteristic of the sensed first stimulation pulse represents a characteristic of the sensed first set of one or more stimulation pulses, and wherein the processing circuitry is configured to calculate the characteristic of the sensed first set of one or more stimulation pulses based on respective characteristic values of each stimulation pulse of the first set of one or more stimulation pulses.

Example 16: A method comprising: delivering, by stimulation generation circuitry, a first stimulation pulse to a patient; sensing, by sensing circuitry, the first stimulation pulse; determining, by processing circuitry, that a value of a characteristic of the sensed first stimulation pulse exceeds a target stimulation pulse value; and responsive to determining that the value of the characteristic of the sensed first stimulation pulse exceeds the target stimulation pulse value, changing, by the processing circuitry, a first value of a parameter to a second value of the parameter that at least partially defines a second stimulation pulse deliverable by the stimulation generation circuitry after the first stimulation pulse was sensed.

Example 17: The method of example 16, wherein determining that the value of the characteristic of the sensed first stimulation pulse exceeds the target stimulation pulse value comprises: determining that the value of the characteristic of the sensed first stimulation pulse is greater than a target maximum stimulation pulse characteristic value, and wherein changing the first value of the parameter to the second value of the parameter comprises: decreasing the first value of the parameter to the second value of the parameter, the second value of the parameter at least partially defining the second stimulation pulse.

Example 18: The method of example 17, wherein decreasing the first value of the parameter to the second value of the parameter that at least partially defines the second stimulation pulse comprises: setting the parameter which at least partially defines the second stimulation pulse to a fallback parameter value that at least partially defines the second stimulation pulse, wherein the method further comprises: sensing a third stimulation pulse following the second stimulation pulse; and responsive to determining that a value of a characteristic of the sensed third stimulation pulse does not exceed the target stimulation pulse value, restoring the parameter that at least partially defines a fourth stimulation pulse deliverable by the stimulation generation circuitry to the first value of the parameter.

Example 19: The method of examples 17-18, further comprising: determining, by the processing circuitry, that the value of the characteristic of the sensed first stimulation pulse is less than a target minimum stimulation pulse characteristic value, wherein a target range of stimulation pulse characteristic values extend from the target minimum stimulation pulse characteristic value to the target maximum stimulation pulse characteristic value; and responsive to determining that the value of the characteristic of the sensed first stimulation pulse is less than the target minimum stimulation pulse characteristic value, increasing the first value of the parameter to the second value of the parameter that at least partially defines the second stimulation pulse.

Example 20: The method of examples 16-19, further comprising: delivering, by the stimulation generation circuitry, a plurality of stimulation pulses including the first stimulation pulse and the second stimulation pulse; and detecting, by the sensing circuitry, a plurality of evoked compound action potentials (ECAPs), wherein each ECAP of the plurality of ECAPs is elicited by a respective pulse of the plurality of pulses, and wherein the number of ECAPs of the plurality of ECAPs is lower than a number of stimulation pulses of the plurality of stimulation pulses.

Example 21: The method of examples 16-20, further comprising: generating, by an accelerometer, an accelerometer signal; identifying, by the processing circuitry based on the accelerometer signal, a posture of a set of postures which the patient is occupying; identifying, by the processing circuitry, an amplitude of the first stimulation pulse; and selecting, by the processing circuitry based on the identified posture and the amplitude of the first stimulation pulse, the target stimulation pulse value from a set of target stimulation pulse values, wherein each target stimulation pulse value of the set of target stimulation pulse values corresponds to a respective posture of the set of postures and a respective amplitude of the first stimulation pulse.

Example 22: A medical device comprising: stimulation generation circuitry configured to deliver a first stimulation pulse to a patient; sensing circuitry configured to sense a residual phase of the first stimulation pulse; and processing circuitry configured to: determine that a value of a characteristic of the sensed residual phase of the first stimulation pulse exceeds a target residual phase value; and responsive to determining that the value of the characteristic of the sensed residual phase exceeds the target residual phase value, change a first value of a parameter to a second value of the parameter that at least partially defines a second stimulation pulse deliverable by the stimulation generation circuitry after the residual phase of the first stimulation pulse was sensed.

Example 23: The medical device of example 22, wherein the stimulation generation circuitry is configured to deliver a plurality of stimulation pulses including the first stimulation pulse and the second stimulation pulse, and wherein the sensing circuitry is further configured to: detect a plurality of evoked compound action potentials (ECAPs), wherein each ECAP of the plurality of ECAPs is elicited by a respective pulse of the plurality of pulses, and wherein the number of ECAPs of the plurality of ECAPs is lower than a number of stimulation pulses of the plurality of stimulation pulses.

Example 24: The medical device of example 23, wherein the processing circuitry is further configured to determine whether the plurality of stimulation pulses elicit greater than a threshold ratio of detectable ECAPs per stimulation pulse.

Example 25: The medical device of example 24, wherein to determine whether the plurality of stimulation pulses elicit greater than the threshold ratio of detectable ECAPs per stimulation pulse, the processing circuitry is configured to: identify a set of ECAPs elicited by a sequence of consecutive stimulation pulses of the plurality of stimulation pulses; calculate a ratio of a number of the set of ECAPs to a number of the sequence of consecutive stimulation pulses; and determine whether the ratio is greater than the threshold ratio.

Example 26: The medical device of claims 24-25, wherein the processing circuitry is further configured to: responsive to determining that the plurality of stimulation pulses elicit greater than the threshold ratio of detectible ECAPs: change, based on the value of the characteristic of the sensed residual phase of the first stimulation pulse and a value of a characteristic of an ECAP corresponding to the first stimulation pulse, the value of the parameter that at least partially defines the second stimulation pulse.

Example 27: The medical device of claims 24-26, wherein the processing circuitry is further configured to: responsive to determining that the plurality of stimulation pulses does not elicit greater than the threshold ratio of detectible ECAPs: change, based on the value of the characteristic of the sensed residual phase of the first stimulation pulse and not based on a value of a characteristic of an ECAP corresponding to the first stimulation pulse, the value of the parameter that at least partially defines the second stimulation pulse.

The techniques described in this disclosure may be implemented, at least in part, in hardware, software, firmware, or any combination thereof. For example, various aspects of the techniques may be implemented within one or more microprocessors, DSPs, ASICS, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:
1. A medical device comprising:
   stimulation generation circuitry configured to deliver a plurality of stimulation pulses including a first stimulation pulse and a second stimulation pulse to a patient, the first stimulation pulse at least partially defined by a first value of a parameter;
   sensing circuitry configured to sense, via an electrode combination, the first stimulation pulse delivered to the patient; and
   processing circuitry configured to:
      identify a value of a characteristic of the first stimulation pulse sensed via the sensing circuitry and the electrode combination;
      determine that the value of a characteristic of the sensed first stimulation pulse exceeds a target stimulation pulse value; and
      responsive to determining that the value of the characteristic of the sensed first stimulation pulse exceeds the target stimulation pulse value, change the first value of the parameter to a second value of the parameter that at least partially defines the second stimulation pulse deliverable by the stimulation generation circuitry after the first stimulation pulse was sensed, wherein:
   the sensing circuitry is configured to detect a plurality of evoked compound action potentials (ECAPs), each ECAP of the plurality of ECAPs being elicited by a respective pulse of the plurality of stimulation pulses,
   the number of ECAPs of the plurality of ECAPs is lower than a number of stimulation pulses of the plurality of stimulation pulses, and
   the processing circuitry is configured to determine whether the plurality of stimulation pulses elicit greater than a threshold ratio of detectable ECAPs to stimulation pulses.

2. The medical device of claim 1, wherein to determine that the value of the characteristic of the sensed first stimulation pulse exceeds the target stimulation pulse value, the processing circuitry is configured to:
   determine that the value of the characteristic of the sensed first stimulation pulse is greater than a target maximum stimulation pulse characteristic value, and wherein to change the first value of the parameter to the second value of the parameter, the processing circuitry is configured to:
   decrease the first value of the parameter to the second value of the parameter, the second value of the parameter at least partially defining the second stimulation pulse.

3. The medical device of claim 2, wherein to decrease the first value of the parameter to the second value of the parameter that at least partially defines the second stimulation pulse, the processing circuitry is configured to:
   set the parameter which at least partially defines the second stimulation pulse to a fallback parameter value that at least partially defines the second stimulation pulse,
   wherein the sensing circuitry is further configured to sense a third stimulation pulse following the second stimulation pulse, and
   wherein the processing circuitry is configured to:
      identify a value of a characteristic of the third stimulation pulse sensed via the sensing circuitry;
      responsive to determining that the value of a characteristic of the sensed third stimulation pulse does not exceed the target stimulation pulse value, restore the parameter that at least partially defines a fourth stimulation pulse deliverable by the stimulation generation circuitry to the first value of the parameter.

4. The medical device of claim 2, wherein the processing circuitry is further configured to:
- determine that the value of the characteristic of the sensed first stimulation pulse is less than a target minimum stimulation pulse characteristic value, wherein a target range of stimulation pulse characteristic values extend from the target minimum stimulation pulse characteristic value to the target maximum stimulation pulse characteristic value; and
- responsive to determining that the value of the characteristic of the sensed first stimulation pulse is less than the target minimum stimulation pulse characteristic value, increase the first value of the parameter to the second value of the parameter that at least partially defines the second stimulation pulse.

5. The medical device of claim 1, wherein to determine whether the plurality of stimulation pulses elicit greater than the threshold ratio of detectable ECAPs to stimulation pulses, the processing circuitry is configured to:
- identify a set of ECAPs elicited by a sequence of consecutive stimulation pulses of the plurality of stimulation pulses;
- calculate a ratio of a number of the set of ECAPs to a number of the sequence of consecutive stimulation pulses; and
- determine whether the ratio is greater than the threshold ratio.

6. The medical device of claim 1, wherein the processing circuitry is further configured to:
- responsive to determining that the plurality of stimulation pulses elicit greater than the threshold ratio of detectible ECAPs:
- change, based on the value of the characteristic of the sensed first stimulation pulse and a value of a characteristic of an ECAP corresponding to the first stimulation pulse, the value of the parameter that at least partially defines the second stimulation pulse.

7. The medical device of claim 1, wherein the processing circuitry is further configured to:
- responsive to determining that the plurality of stimulation pulses does not elicit greater than the threshold ratio of detectible ECAPs:
- change, based on the value of the characteristic of the first stimulation pulse and not based on a value of a characteristic of an ECAP corresponding to the first stimulation pulse, the value of the parameter that at least partially defines the second stimulation pulse.

8. The medical device of claim 1, further comprising:
- an accelerometer configured to generate an accelerometer signal, wherein the processing circuitry is further configured to:
- identify, based on the accelerometer signal, a posture of a set of postures which the patient is occupying;
- identify an amplitude of the first stimulation pulse; and
- select, based on the identified posture and the amplitude of the first stimulation pulse, the target stimulation pulse value from a set of target stimulation pulse values, wherein each target stimulation pulse value of the set of target stimulation pulse values corresponds to a respective posture of the set of postures and a respective amplitude of the first stimulation pulse.

9. The medical device of claim 1, wherein the medical device comprises an implantable medical device, and wherein the implantable medical device comprises the stimulation generation circuitry, the sensing circuitry, and the processing circuitry.

10. The medical device of claim 1, wherein the first value of the parameter at least partially defines the first stimulation pulse.

11. The medical device of claim 1, wherein the first stimulation pulse represents a control pulse of a set of control pulses, wherein the second stimulation pulse represents an informed pulse of a set of informed pulses, wherein the first value of the parameter at least partially defines a previous informed pulse of the set of informed pulses.

12. The medical device of claim 1, wherein the stimulation generation circuitry is configured to deliver at least one stimulation pulse between a time in which the stimulation generation circuitry delivers the first stimulation pulse and a time in which the stimulation generation circuitry delivers the second stimulation pulse.

13. The medical device of claim 1, wherein the first stimulation pulse is one of a first set of one or more stimulation pulses, wherein the second stimulation pulse is one of a second set of one or more stimulation pulses, wherein the characteristic of the sensed first stimulation pulse represents a characteristic of the sensed first set of one or more stimulation pulses, and wherein the processing circuitry is configured to calculate the characteristic of the sensed first set of one or more stimulation pulses based on respective characteristic values of each stimulation pulse of the first set of one or more stimulation pulses.

14. A method comprising:
- delivering, by stimulation generation circuitry, a first stimulation pulse to a patient, the first stimulation pulse at least partially defined by a first value of a parameter;
- sensing, by sensing circuitry and via an electrode combination, the first stimulation pulse delivered to the patient;
- identifying, by processing circuitry, a value of a characteristic of the first stimulation pulse sensed via the sensing circuitry and the electrode combination;
- determining, by the processing circuitry, that a value of a characteristic of the sensed first stimulation pulse exceeds a target stimulation pulse value;
- responsive to determining that the value of the characteristic of the sensed first stimulation pulse exceeds the target stimulation pulse value, changing, by the processing circuitry, the first value of the parameter to a second value of the parameter that at least partially defines a second stimulation pulse deliverable by the stimulation generation circuitry after the first stimulation pulse was sensed;
- delivering, by the stimulation generation circuitry, a plurality of stimulation pulses, the plurality of stimulation pulses including the first stimulation pulse and the second stimulation pulse; and
- detecting, by the sensing circuitry, a plurality of evoked compound action potentials (ECAPs), each ECAP of the plurality of ECAPs being elicited by a respective pulse of the plurality of stimulation pulses, wherein the number of ECAPs of the plurality of ECAPs is lower than a number of stimulation pulses of the plurality of stimulation pulses; and
- determining, by the processing circuitry, whether the plurality of stimulation pulses elicit greater than a threshold ratio of detectable ECAPs to stimulation pulses.

15. The method of claim 14, wherein determining that the value of the characteristic of the sensed first stimulation pulse exceeds the target stimulation pulse value comprises:
- determining that the value of the characteristic of the sensed first stimulation pulse is greater than a target maximum stimulation pulse characteristic value, and wherein changing the first value of the parameter to the second value of the parameter comprises:
  decreasing the first value of the parameter to the second value of the parameter, the second value of the parameter at least partially defining the second stimulation pulse.

16. The method of claim 15, wherein decreasing the first value of the parameter to the second value of the parameter that at least partially defines the second stimulation pulse comprises:
  setting the parameter which at least partially defines the second stimulation pulse to a fallback parameter value that at least partially defines the second stimulation pulse, wherein the method further comprises:
  sensing, by the sensing circuitry, a third stimulation pulse following the second stimulation pulse;
  identifying, by the processing circuitry, a value of a characteristic of the third stimulation pulse sensed via the sensing circuitry; and
  responsive to determining that the value of a characteristic of the sensed third stimulation pulse does not exceed the target stimulation pulse value, restoring the parameter that at least partially defines a fourth stimulation pulse deliverable by the stimulation generation circuitry to the first value of the parameter.

17. The method of claim 15, further comprising:
  determining, by the processing circuitry, that the value of the characteristic of the sensed first stimulation pulse is less than a target minimum stimulation pulse characteristic value, wherein a target range of stimulation pulse characteristic values extend from the target minimum stimulation pulse characteristic value to the target maximum stimulation pulse characteristic value; and
  responsive to determining that the value of the characteristic of the sensed first stimulation pulse is less than the target minimum stimulation pulse characteristic value, increasing the first value of the parameter to the second value of the parameter that at least partially defines the second stimulation pulse.

18. The method of claim 14, further comprising:
  generating, by an accelerometer, an accelerometer signal;
  identifying, by the processing circuitry based on the accelerometer signal, a posture of a set of postures which the patient is occupying;
  identifying, by the processing circuitry, an amplitude of the first stimulation pulse; and
  selecting, by the processing circuitry based on the identified posture and the amplitude of the first stimulation pulse, the target stimulation pulse value from a set of target stimulation pulse values, wherein each target stimulation pulse value of the set of target stimulation pulse values corresponds to a respective posture of the set of postures and a respective amplitude of the first stimulation pulse.

19. A medical device comprising:
  stimulation generation circuitry configured to deliver a first stimulation pulse to a patient, the first stimulation pulse at least partially defined by a first value of a parameter, wherein the first stimulation pulse comprises a first phase and a second phase;
  sensing circuitry configured to sense, via an electrode combination, a residual phase of the first stimulation pulse delivered to the patient, the residual phase occurring after the first phase and the second phase; and
  processing circuitry configured to:
    identify a value of a characteristic of the residual phase of the first stimulation pulse sensed via the sensing circuitry and the electrode combination;
    determine that the value of a characteristic of the residual phase of the first stimulation pulse exceeds a target residual phase value; and
    responsive to determining that the value of the characteristic of the sensed residual phase exceeds the target residual phase value, change the first value of the parameter to a second value of the parameter that at least partially defines a second stimulation pulse deliverable by the stimulation generation circuitry after the residual phase of the first stimulation pulse was sensed.

20. The medical device of claim 19, wherein the stimulation generation circuitry is configured to deliver a plurality of stimulation pulses including the first stimulation pulse and the second stimulation pulse, and wherein the sensing circuitry is further configured to:
  detect a plurality of evoked compound action potentials (ECAPs), wherein each ECAP of the plurality of ECAPs is elicited by a respective pulse of the plurality of pulses, and wherein the number of ECAPs of the plurality of ECAPs is lower than a number of stimulation pulses of the plurality of stimulation pulses.

21. The medical device of claim 20, wherein the processing circuitry is further configured to determine whether the plurality of stimulation pulses elicit greater than a threshold ratio of detectable ECAPs to stimulation pulses.

22. The medical device of claim 21, wherein to determine whether the plurality of stimulation pulses elicit greater than the threshold ratio of detectable ECAPs to stimulation pulses, the processing circuitry is configured to:
  identify a set of ECAPs elicited by a sequence of consecutive stimulation pulses of the plurality of stimulation pulses;
  calculate a ratio of a number of the set of ECAPs to a number of the sequence of consecutive stimulation pulses; and
  determine whether the ratio is greater than the threshold ratio.

23. The medical device of claim 21, wherein the processing circuitry is further configured to:
  responsive to determining that the plurality of stimulation pulses elicit greater than the threshold ratio of detectible ECAPs:
  change, based on the value of the characteristic of the sensed residual phase of the first stimulation pulse and a value of a characteristic of an ECAP corresponding to the first stimulation pulse, the value of the parameter that at least partially defines the second stimulation pulse.

24. The medical device of claim 21, wherein the processing circuitry is further configured to:
  responsive to determining that the plurality of stimulation pulses does not elicit greater than the threshold ratio of detectible ECAPs:
  change, based on the value of the characteristic of the sensed residual phase of the first stimulation pulse and not based on a value of a characteristic of an ECAP corresponding to the first stimulation pulse, the value of the parameter that at least partially defines the second stimulation pulse.

25. The medical device of claim 1, wherein the processing circuitry is configured to:

determine that the plurality of stimulation pulses elicit greater than the threshold ratio of detectable ECAPs to stimulation pulses; and responsive to the determination, control electrical stimulation therapy based on one or more characteristics of detectable ECAP signals.

26. The medical device of claim 1, wherein the processing circuitry is configured to:

determine that the plurality of stimulation pulses elicit less than the threshold ratio of detectable ECAPs to stimulation pulses; and responsive to the determination, control electrical stimulation therapy based on one or more characteristics of detected stimulation pulses.

27. The method of claim 14, wherein determining whether the plurality of stimulation pulses elicit greater than the threshold ratio of detectable ECAPs to stimulation pulses comprises:

determining that the plurality of stimulation pulses elicit greater than the threshold ratio of detectable ECAPs to stimulation pulses;

responsive to determining that the plurality of stimulation pulses elicit greater than the threshold ratio, control electrical stimulation therapy based on one or more characteristics of detectable ECAP signals;

determining that the plurality of stimulation pulses elicit less than the threshold ratio of detectable ECAPs to stimulation pulses; and responsive to determining that the plurality of stimulation pulses elicit less than the threshold ratio, control electrical stimulation therapy based on one or more characteristics of detected stimulation pulses.

* * * * *